US011639386B2

(12) United States Patent
Johnson et al.

(10) Patent No.: US 11,639,386 B2
(45) Date of Patent: May 2, 2023

(54) BI-SPECIFIC MONOVALENT DIABODIES THAT ARE CAPABLE OF BINDING CD19 AND CD3, AND USES THEREOF

(71) Applicant: MacroGenics, Inc., Rockville, MD (US)

(72) Inventors: Leslie S. Johnson, Darnestown, MD (US); Ezio Bonvini, Potomac, MD (US); Chia-Ying Kao Lam, San Jose, CA (US); Paul A. Moore, North Potomac, MD (US); Liqin Liu, Germantown, MD (US); Scott Koenig, Rockville, MD (US)

(73) Assignee: MacroGenics, Inc., Rockville, MD (US)

(*) Notice: Subject to any disclaimer, the term of this patent is extended or adjusted under 35 U.S.C. 154(b) by 498 days.

(21) Appl. No.: 16/807,514

(22) Filed: Mar. 3, 2020

(65) Prior Publication Data
US 2020/0216537 A1 Jul. 9, 2020

Related U.S. Application Data

(62) Division of application No. 15/514,334, filed as application No. PCT/US2015/051314 on Sep. 22, 2015, now Pat. No. 10,633,443.

(60) Provisional application No. 62/055,695, filed on Sep. 26, 2014.

(51) Int. Cl.
*C07K 16/28* (2006.01)
*C07K 16/46* (2006.01)
*C07K 16/30* (2006.01)
*A61K 39/395* (2006.01)
*A61K 39/00* (2006.01)

(52) U.S. Cl.
CPC .... *C07K 16/2803* (2013.01); *A61K 39/39558* (2013.01); *C07K 16/2809* (2013.01); *C07K 16/2896* (2013.01); *C07K 16/3061* (2013.01); *C07K 16/468* (2013.01); *A61K 2039/505* (2013.01); *C07K 2317/31* (2013.01); *C07K 2317/33* (2013.01); *C07K 2317/35* (2013.01); *C07K 2317/524* (2013.01); *C07K 2317/526* (2013.01); *C07K 2317/56* (2013.01); *C07K 2317/569* (2013.01); *C07K 2317/626* (2013.01); *C07K 2317/73* (2013.01); *C07K 2317/90* (2013.01); *C07K 2317/92* (2013.01); *C07K 2317/94* (2013.01)

(58) Field of Classification Search
CPC ........ A61K 39/39558; A61K 2039/505; C07K 16/2809; C07K 16/468
USPC .......................................... 424/133.1, 136.1
See application file for complete search history.

(56) References Cited

U.S. PATENT DOCUMENTS

| | | | |
|---|---|---|---|
| 4,526,938 A | 7/1985 | Churchill, Jr. et al. | |
| 4,816,567 A | 3/1989 | Cabilly et al. | |
| 4,980,286 A | 12/1990 | Morgan, Jr. et al. | |
| 5,128,326 A | 7/1992 | Balazs et al. | |
| 5,290,540 A | 3/1994 | Prince et al. | |
| 5,624,821 A | 4/1997 | Winter et al. | |
| 5,679,377 A | 10/1997 | Bernstein et al. | |
| 5,807,715 A | 9/1998 | Morrison et al. | |
| 5,855,913 A | 1/1999 | Hanes et al. | |
| 5,866,692 A | 2/1999 | Shitara et al. | |
| 5,874,064 A | 2/1999 | Edwards et al. | |
| 5,888,533 A | 3/1999 | Dunn | |
| 5,912,015 A | 6/1999 | Bernstein et al. | |
| 5,916,597 A | 6/1999 | Lee et al. | |
| 5,934,272 A | 8/1999 | Lloyd et al. | |
| 5,945,115 A | 8/1999 | Dunn et al. | |
| 5,985,309 A | 11/1999 | Edwards et al. | |
| 5,985,320 A | 11/1999 | Edwards et al. | |
| 5,989,463 A | 11/1999 | Tracy et al. | |
| 6,019,968 A | 2/2000 | Platz et al. | |
| 6,331,415 B1 | 12/2001 | Cabilly et al. | |
| 6,992,234 B2 | 1/2006 | Roopenian | |
| 7,358,416 B2 | 4/2008 | Roopenian | |
| 7,585,952 B2 | 9/2009 | D'Alessio | |
| 7,968,687 B2 | 6/2011 | McDonagh et al. | |
| 9,587,021 B2 | 3/2017 | Huang et al. | |
| 10,150,812 B2 | 12/2018 | Huang et al. | |
| 10,633,440 B2 * | 4/2020 | Bonvini | A61P 11/00 |
| 10,633,443 B2 * | 4/2020 | Johnson | C07K 16/468 |
| 10,647,768 B2 * | 5/2020 | Johnson | A61P 13/08 |
| 11,459,394 B2 * | 10/2022 | Liu | A61K 45/06 |
| 2004/0058400 A1 | 3/2004 | Hollinger et al. | |
| 2004/0220388 A1 | 11/2004 | Mertens et al. | |
| 2009/0060910 A1 | 3/2009 | Johnson et al. | |
| 2010/0173978 A1 | 7/2010 | D'Alessio et al. | |
| 2010/0174053 A1 | 7/2010 | Johnson et al. | |

(Continued)

FOREIGN PATENT DOCUMENTS

| | | |
|---|---|---|
| EP | 2601216 | 12/2008 |
| EP | 2158221 | 3/2010 |

(Continued)

OTHER PUBLICATIONS

Almagro & Franssen, Frontiers in Bioscience, 13:1619-33 (2008).*

(Continued)

*Primary Examiner* — Lynn A Bristol
(74) *Attorney, Agent, or Firm* — Jeffrey I. Auerbach; Auerbach, LLC

(57) ABSTRACT

CD19×CD3 bi-specific monovalent diabodies, and particularly, CD19×CD3 bi-specific monovalent Fc diabodies, are capable of simultaneous binding to CD19 and CD3, and are used in the treatment of hematologic malignancies.

10 Claims, 30 Drawing Sheets

Specification includes a Sequence Listing.

(56) References Cited

U.S. PATENT DOCUMENTS

| | | | |
|---|---|---|---|
| 2011/0206672 | A1 | 8/2011 | Little et al. |
| 2013/0004416 | A1 | 1/2013 | Wu et al. |
| 2013/0295121 | A1 | 11/2013 | Johnson et al. |
| 2014/0099318 | A1 | 4/2014 | Huang et al. |
| 2017/0137519 | A1 | 5/2017 | Huang et al. |
| 2017/0157251 | A1* | 6/2017 | Bonvini ............ A61K 47/6849 |
| 2017/0198045 | A1 | 7/2017 | Johnson et al. |
| 2017/0204176 | A1 | 7/2017 | Bonvini et al. |
| 2017/0247452 | A1* | 8/2017 | Johnson ............ C07K 16/2809 |
| 2018/0371104 | A1 | 12/2018 | Bonvini et al. |
| 2019/0002563 | A1 | 1/2019 | Johnson et al. |
| 2019/0322741 | A1* | 10/2019 | Chen ...................... A61P 35/00 |
| 2020/0023076 | A1* | 1/2020 | Fotin-Mleczek .. C07K 16/1018 |
| 2020/0062854 | A1* | 2/2020 | Liu ..................... C07K 16/2878 |
| 2020/0199223 | A1* | 6/2020 | Bonvini ................. A61P 15/00 |
| 2020/0207850 | A1* | 7/2020 | Johnson ................. A61P 13/10 |
| 2021/0155694 | A1* | 5/2021 | Bonvini ............ C07K 16/3061 |
| 2021/0171630 | A1* | 6/2021 | Diedrich ............ C07K 16/2809 |
| 2021/0246194 | A1* | 8/2021 | Lam .................... C07K 16/468 |

FOREIGN PATENT DOCUMENTS

| | | |
|---|---|---|
| EP | 2376109 | 7/2010 |
| EP | 2714079 | 11/2012 |
| WO | WO 1991/003493 | 3/1991 |
| WO | WO 1991/005548 | 5/1991 |
| WO | WO 1992/019244 | 11/1992 |
| WO | WO 1992/022583 | 12/1992 |
| WO | WO 1996/020698 | 7/1996 |
| WO | WO 1997/032572 | 9/1997 |
| WO | WO 1997/044013 | 11/1997 |
| WO | WO 1998/002463 | 1/1998 |
| WO | WO 1998/031346 | 7/1998 |
| WO | WO 1999/015154 | 4/1999 |
| WO | WO 1999/020253 | 4/1999 |
| WO | WO 1999/066903 | 12/1999 |
| WO | WO 2002/002781 | 1/2002 |
| WO | WO 2003/025018 | 3/2003 |
| WO | WO 2013/119903 | 8/2003 |
| WO | WO 2005/061547 | 7/2005 |
| WO | WO 2006/113665 | 10/2006 |
| WO | WO 2007/075270 | 7/2007 |
| WO | WO 2007/146968 | 12/2007 |
| WO | WO 2008/003103 | 1/2008 |
| WO | WO 2008/003116 | 1/2008 |
| WO | WO 2008/027236 | 3/2008 |
| WO | WO 2008/157379 | 12/2008 |
| WO | WO 2009/132876 | 11/2009 |
| WO | WO 2010/028795 | 3/2010 |
| WO | WO 2010/028796 | 3/2010 |
| WO | WO 2010/028797 | 3/2010 |
| WO | WO 2010/080538 | 7/2010 |
| WO | WO 2010/108127 | 9/2010 |
| WO | WO 2010/136172 | 12/2010 |
| WO | WO 2011/086091 | 7/2011 |
| WO | WO 2011/133886 | 10/2011 |
| WO | WO 2012/018687 | 2/2012 |
| WO | WO 2012/156430 | 11/2012 |
| WO | WO 2012/162067 | 11/2012 |
| WO | WO 2012/162068 | 11/2012 |
| WO | WO 2012/162583 | 11/2012 |
| WO | WO 2013/003652 | 1/2013 |
| WO | WO 2013/006544 | 1/2013 |
| WO | WO 2003/012069 | 2/2013 |
| WO | WO 2013/163427 | 10/2013 |
| WO | WO 2013/174873 | 11/2013 |
| WO | WO 2014/022540 | 2/2014 |
| WO | WO 2014/106015 | 7/2014 |
| WO | WO 2014/110601 | 7/2014 |
| WO | WO 2014/145806 | 9/2014 |
| WO | WO 2015/026894 | 2/2015 |
| WO | WO 2016/122702 | 8/2016 |

OTHER PUBLICATIONS

Edwards et al., J Mol Biol 334:103-118 (2003).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021).*
Lo et al., BMC Genomics vol. 22, Article No. 116 (2021).*
Alt M. et al. (1999) "Novel Tetravalent and Bispeci¢ c IgG-Like Antibody Molecules Combining Single-Chain Diabodies with the Immunoglobulin Q1 Fc or CH3 Region," FEBS Lett. 454:90-94.
Anderson K.C. et al. (1984) "Expression of Human B Cell-Associated Antigens on Leukemias and Lymphomas: A Model of Human B Cell Differentiation," Blood 63:1424-1433.
Apostolovic B. et al. (2008) "pH-Sensitivity of the E3/K3 Heterodimeric Coiled Coil," Biomacromolecules 9:3173-3180.
Arndt K.M. et al. (2001) "Helix-stabilized Fv (hsFv) Antibody Fragments: Substituting the Constant Domains of a Fab Fragment for a Heterodimeric Coiled-coil Domain," J. Mol. Biol. 312:221-228.
Arndt K.M. et al. (2002) "Comparison of In Vivo Selection and Rational Design of Heterodimeric Coiled Coils," Structure 10:1235-1248.
Asano R. et al. (2004) "A Diabody For Cancer Immunotherapy and Its Functional Enhancement by Fusion of Human Fc Domain," Abstract 3P-683, J. Biochem. 76(8):992.
Atwell S. et al. (1997) "Stable Heterodimers from Remodeling the Domain Interface of a Homodimer Using a Phage Display Library," J. Mol. Biol. 270: 26-35.
Baeuerle P.A. et al. (2008) "BiTE: A New Class of Antibodies That Recruit T Cells," Drugs Fut. 33: 137-147.
Baeuerle P.A. et al. (2009) "Bispecific T-Cell Engaging Antibodies for Cancer Therapy," Cancer Res. 69(12):4941-4944.
Baeuerle P.A. et al. (2011) "Bispecific T Cell Engager for Cancer Therapy," In: BISPECIFIC ANTIBODIES, Kontermann, R.E. (Ed.) Springer, Berlin, Heidelberg; pp. 273-287.
Bargou R. et al. (2008) "Tumor Regression in Cancer Patients by Very Low Doses of a T Cell-Engaging Antibody," Science 321(5891):974-977.
Bedzyk W.D. et al. (1989) "Comparison of Variable Region Primary Structures Within an Anti-Fluorescein Idiotype Family," J. Biol. Chem. 264(3): 1565-1569.
Bird R.E. et al. (1988) "Single-Chain Antigen-Binding Proteins," Science 242:423-426.
Boucher C. et al. (2010) "Protein Detection by Western Blot Via Coiled—Coil Interactions," Analytical Biochemistry 399:138-140.
Buchwald H. et al. (1980) "Long-Term, Continuous Intravenous Heparin Administration by An Implantable Infusion Pump in Ambulatory Patients With Recurrent Venous Thrombosis," Surgery 88:507-516.
Cachia P.J. et al. (2004) "Synthetic Peptide Vaccine Development: Measurement of Polyclonal Antibody Affinity and Cross-Reactivity Using a New Peptide Capture and Release System for Surface Plasmon Resonance Spectroscopy," J. Mol. Recognit. 17:540-557.
Campo E. et al. (2011) "The 2008 WHO Classification of Lymphoid Neoplasms and Beyond: Evolving Concepts and Practical Applications," Blood 117(19):5019-5032.
Cao et al. (2003) "Bispecific Antibody Conjugates in Therapeutics," Adv. Drug. Deliv. Rev. 55:171-197.
Castillo J. et al. (2008) "Newer Monoclonal Antibodies for Hematological Malignancies," Exp. Hematol. 36(7):755-768.
Chan C.E.Z. et al. (2009) "The Use of Antibodies in The Treatment of Infectious Diseases," Singapore Med. J. 50(7):663-666.
Cheson B.D. et al. (2008) "Monoclonal Antibody Therapy for B-Cell Non-Hodgkin's Lymphoma," N. Engl. J. Med. 359(6):613-626.
Chetty R. et al. (1994) "CD3: Structure, Function, And Role of Immuno staining In Clinical Practice," J. Pathol. 173(4):303-307.
Czuczman M.S. et al. (2008) "Acquirement of Rituximab Resistance in Lymphoma Cell Lines Is Associated With Both Global CD20

(56) References Cited

OTHER PUBLICATIONS

Gene And Protein Down-Regulation Regulated At The Pretranscriptional And Post-transcriptional Levels," Clin. Cancer Res. 14:1561-1570.

Davis T.A. et al. (1999) "Therapy of B-cell Lymphoma with Anti-CD20 Antibodies Can Result in The Loss Of CD20 Antigen Expression," Clin. Cancer Res. 5:611-615.

De Crescenzo G.D. et al. (2003) "Real-Time Monitoring of the Interactions of Two-Stranded de novo Designed Coiled-Coils: Effect of Chain Length on the Kinetic and Thermodynamic Constants of Binding," Biochemistry 42:1754-1763.

Del Nagro C.J. et al. (2005) "CD19 Function in Central and Peripheral B-Cell Development," Immunologic Res. 31:119-131.

Du et al. (2008) "Differential Cellular Internalization of Anti-CD19 And -CD22 Immuno toxins Results In Different Cytotoxic Activity," Cancer Res. 68:6300-6305.

During M.J. et al. (1989) "Controlled Release of Dopamine from A Polymeric Brain Implant: In Vivo Characterization," Ann. Neurol. 25:351-356.

Fernandez-Rodriquez J. et al. (2012) "Induced Heterodimerization And Purification of Two Target Proteins by A Synthetic Coiled-Coil Tag," Protein Science 21:511-519.

FitzGerald K. et al. (1997) "Improved Tumour Targeting By Disulphide Stabilized Diabodies Expressed In Pichia pastoris," Protein Eng. 10:1221-1225.

Fowler N. et al. (2013) "Developing Novel Strategies to Target B-Cell Malignancies," in Targeted Pathways, B-Cell Lymphoma in 2013 ASCO Educational Book, pp. 366-372.

Frankel et al. (2013) "Targeting T Cells to Tumor Cells Using Bispecific Antibodies," Curr. Opin. Chem. Biol. 17:385-392.

Gabrilovich D. et al. (2003) "Tumor Escape from Immune Response: Mechanisms and Targets of Activity," Curr. Drug Targets 4(7):525-536.

GenBank accession No. M28170 (2 pages).

Ghosh T.S. et al. (2009) "End-To-End and End-To-Middle Interhelical Interactions: New Classes of Interacting Helix Pairs In Protein Structures," Acta Cryst. D65:1032-1041.

Ginaldi et al. (1998) "Levels of Expression of CD19 And CD20 In Chronic B Cell Leukaemias," J. Clin. Pathol. 51:364-369.

Grigoryan, G. et al. (2008) "Structural Specificity in Coiled-Coil Interactions," Curr. Opin. Struc. Biol. 18:477-483.

Grosjean H. et al. (1982) "Preferential Codon Usage in Prokaryotic Genes: The Optimal Codon-Anticodon Interaction Energy and The Selective Codon Usage in Efficiently Expressed Genes" Gene 18(3):199-209.

Gruber, M. et al. (1994) "Efficient Tumor Cell Lysis Mediated by A Bispecific Single Chain Antibody Expressed in Escherichia coli," J. Immunol. 152(11):5368-5374.

Guy, C.S. et al. (2009) "Organization of Proximal Signal Initiation At The TCR:CD3 Complex," Immunol. Rev. 232(1):7-21.

Hammer O. (2012) "CD19 As An Attractive Target For Antibody-Based Therapy," mAbs 4:571-577.

Haraya, K. (2014) "Application of Human FcRn Transgenic Mice As A Pharmacokinetic Screening Tool of Monoclonal Antibody," Xenobiotica 44(12):1127-1134; Published online Jul. 17, 2014.

Hoelzer D. (2013) Targeted Therapy with Monoclonal Antibodies in Acute Lymphoblasitic Leukemia, Curr. Opin. Oncol. 25:701-706.

Holliger P. et al. (1993) "'Diabodies': Small Bivalent and Bispecific Antibody Fragments," Proc. Natl. Acad. Sci. (U.S.A.) 90:6444-6448.

Holliger P. et al. (1996) "Specific Killing of Lymphoma Cells by Cytotoxic T-Cells Mediated By A Bispecific Diabody," Protein Eng. 9:299-305.

Holliger P. et al. (1999) "Carcinoembryonic Antigen (CEA)-Specific T-Cell Activation In Colon Carcinoma Induced By Anti-CD3 x Anti-CEA Bispecific Diabodies And B7 x Anti-CEA Bispecific Fusion Proteins," Cancer Res. 59:2909-2916.

Howard M.A. et al. (1989) "Intracerebral Drug Delivery in Rats with Lesion-Induced Memory Deficits," J. Neurosurg, 71(1):105-112.

International Search Report PCT/US2015/051314 (WO 2016/048938) (4 pages).

Johansson M.U. et al. (2002) "Structure, Specificity, And Mode of Interaction for Bacterial Albumin-Binding Modules," J. Biol. Chem. 277(10):8114-8120.

Johnson, S. et al. (2010) "Effector Cell Recruitment with Novel Fv-Based Dual-Affinity Re-Targeting Protein Leads To Potent Tumor Cytolysis And in vivo B-Cell Depletion," J. Mol. Biol. 399(3):436-449.

Joliot A. et al. (1991) "Antennapedia Homeobox Peptide Regulates Neural Morphogenesis," Proc. Natl. Acad. Sci. (U.S.A.) 88:1864-1868.

Kipriyanov, et al. (1998) "Bispecific CD3 x CD19 Diabody for T Cell-Mediated Lysis of Malignant Human B Cells," Int. J. Cancer 77(5):763-772.

Kipriyanov, et al. (2002) "Synergistic Antitumor Effect of Bispecific CD19 x CD3 and CD19 x CD16 Diabodies in a Preclinical Model of Non-Hodgkin's Lymphoma," J. Immunol. 169:137-144.

Kohler, G. et al. (1975) "Continuous Cultures of Fused Cells Secreting Antibody of Predefined Specificity," Nature 256:495-497.

Kuhns, M.S. et al. (2006) "Deconstructing the Form and Function of the TCR/CD3 Complex," Immunity, Feb. 2006;24(2):133-139.

Langer R. (1990) "New Methods Of Drug Delivery," Science 249:1527-1533.

Lech-Maranda et al. (2012) Novel and emerging drugs for acute lymphoblastic leukemia, Current Cancer Drug Targets 12:505-521.

Levy R.J. et al. (1985) "Inhibition of Calcification of Bioprosthetic Heart Valves By Local Controlled-Release Diphosphonate," Science 228:190-192.

Litowski J.R. et al. (2002) "Designing Heterodimeric Two-Stranded α-Helical Coiled-Coils: The Effects of Hydrophobicity And a-Helical Propensity on Protein Folding, Stability, And Specificity," J. Biol. Chem. 277:37272-37279.

Liu, et al. (Blood; 2014; 124(21)) Meeting Info.: $56^{th}$ Annual Meeting of the American-Society-of-Hematoloy. San Francisco, CA, USA. Dec. 6-9, 2014. Amer. Soc. Hematol. (Abstract; Meeting Abstract); pp. 1-3).

Liu, et al. (2017) "MGD011 CD19 x CD3 Dual-Affinity Retargeting Bi-specific Molecule Incorporating Extended Circulating Half-Life for the Treatment of B-Cell Malignancies," Clin. Cancer Res. 23(6):1506-1518.

Loken M.R. et al. (1987) "Flow Cytometric Analysis of Human Bone Marrow. II. Normal B Lymphocyte Development," Blood 70:1316-1324.

Lu, D. et al. (2005) "A Fully Human Recombinant IgG-Like Bispecific Antibody to Both the Epidermal Growth Factor Receptor and the Insulin-Like Growth Factor Receptor for Enhanced Antitumor Activity," J. Biol. Chem. 280(20):19665-19672.

Ma D. et al. (2002) "Radioimmunotherapy for Model B Cell Malignancies Using 90Y-Labeled Anti-CD19 And Anti-CD20 Monoclonal Antibodies," Leukemia 16:60-66.

Maloney, D.G. et al. (1997) "IDEC-C2B8 (Rituximab) Anti-CD20 Monoclonal Antibody Therapy in Patients With Relapsed Low-Grade Non-Hodgkin's Lymphoma," Blood 90(6):2188-2195.

Marvin J.S et al. (2005) "Recombinant Approaches to IgG-Like Bispecific Antibodies," Acta Pharmacol. Sin. 26:649-658.

Mei H.E. et al. (2012) "Rationale of Anti-CD19 Immunotherapy: An Option to Target Autoreactive Plasma Cells in Autoimmunity," Arthritis Res. Ther. 14(Suppl. 5):S1.

Merriam-Webster On-line Definition for "monovalent" (pp. 1-10) (Jan. 4, 2019).

Moore P.A. et al. (2011) "Application of Dual Affinity Retargeting Molecules to Achieve Optimal Redirected T-Cell Killing of B-Cell Lymphoma," Blood 117(17):4542-4551.

Mordenti, J. et al. (1991) "Interspecies Scaling of Clearance and Volume of Distribution Data for Five Therapeutic Proteins," Pharm. Res. 8(11):1351-1359.

Nadler L.M. et al. (1983) "B4, A Human B Lymphocyte-Associated Antigen Expressed on Normal, Mitogen-Activated, And Malignant B Lymphocytes," J. Immunol. 131:244-250.

Nagorsen D. et al. (2012) "Blinatumomab: A Historical Perspective," Pharmacol. Ther. 136(3):334-342.

(56) References Cited

OTHER PUBLICATIONS

Ning S. et al. (1996) "*Intratumor al Radioimmunotheraphy of A Human Colon Cancer Xenograft Using A Sustained-Release Gel*," Radiother. Oncol. 39:179-189.

Olafsen T. et al. (2004) "*Covalent Disulfide-Linked Anti-CEA Diabody Allows Site-Specific Conjugation and Radiolabeling for Tumor Targeting Applications*," Protein Eng. Des. Sel. 17(1):21-27.

Olejniczak S.H. et al. (2008) "*Acquired Resistance to Rituximab is Associated with Chemotherapy Resistance Resulting from Decreased Bax and Bak Expression*," Clin Cancer Res. 14:1550-1560.

Press O.W. et al. (1994) "*Retention of B-Cell-Specific Monoclonal Antibodies by Human Lymphoma Cells*," Blood 83:1390-1397.

Proetzel G. et al. (2014) "*Humanized FcRn mouse models for evaluating pharmacokinetics of human IgG antibodies*," Methods 65(1):148-153.

Raufi A. et al. (2013) "*Targeting CD19 in B-cell lymphoma: emerging role of SAR3419*," Cancer Management Res 3:225-233.

Ridgway J.B.B. et al. (1996) "*'Knobs-Into-Holes' Engineering of Antibody CH3 Domains for Heavy Chain Heterodimerization*," Protein Engr. 9:617-621.

Roopenian, D.C. et al. (2010) "*Human FcRn Transgenic Mice for Pharmacokinetic Evaluation of Therapeutic Antibodies*," Mouse Models for Drug Discovery, Methods in Molecular Biology (Methods and Protocols) 602:93-104.

Sato S. et al. (1995) "*The CD19 Signal Transduction Molecule Is a Response Regulator of B-Lymphocyte Differentiation*," Proc. Natl. Acad. Sci. (U.S.A.) 92:11558-11562.

Saudek C.D. et al. (1989) "*A Preliminary Trial of The Programmable Implantable Medication System for Insulin Delivery*," N. Engl. J. Med. 321:574-579.

Smith M.R. (2003) "*Rituximab (Monoclonal Anti-CD20 Antibody): Mechanisms of Action And Resistance*," Oncogene. 22:7359-68.

Smith-Garvin, J.E. et al. (2009) "*T Cell Activation*," Annu. Rev. Immunol. 27:591-619.

Song Y.K. et al. (1995) "*Antibody Mediated Lung Targeting of Long-Circulating Emulsions*," PDA J. Pharm. Sci. Technol. 50:372-397.

Staerz U.D. et al. (1985) "*Hybrid Antibodies Can Target Sites for Attack by T Cells*," Nature 314:628-631.

Stamenkovic I. et al. (1988) "*CD19, The Earliest Differentiation Antigen of The B Cell Lineage, Bears Three Extracellular Immunoglobulin-Like Domains and An Epstein-Barr Virus-Related Cytoplasmic Tail*," J. Exper. Med. 168(3):1205-1210.

Stein C. et al. (2012) "*Clinical Chemistry of Human FcRn Transgenic Mice*," Mamm. Genome 23(3-4):259-269.

Steinkruger J.D. et al. (2012) "*The d'--d--' Vertical Triad is Less Discriminating Than the a'--a--a' Vertical Triad in the Antiparallel Coiled-coil Dimer Motif*," J. Amer. Chem. Soc. 134(5):2626-2633.

Stock W. et al. (2013) "*Dose Intensification of Daunorubicin and Cytarabine During Treatment of Adult Acute Lymphoblastic Leukemia: Results of Cancer and Leukemia Group B Study 19802*," Cancer. Jan. 1, 2013;119(1):90-98.

Straussman R. et al. (2007) "*Kinking the Coiled Coil—Negatively Charged Residues at the Coiled-coil Interface*," J. Molec. Biol. 366:1232-1242.

Sun, Z. J. et al. (2001) "Mechanisms Contributing To T Cell Receptor Signaling And Assembly Revealed By The Solution Structure Of An Ectodomain Fragment Of The CD3ε:γ Heterodimer," Cell 105(7):913-923.

Supplementary European Search Report (Application EP15 84 4698; dated Mar. 2, 2018; 5 pages).

Szatrowski T.P. et al. (2003) "*Lineage Specific Treatment of Adult Patients With Acute Lymphoblastic Leukemia In First Remission With Anti-B4-Blocked Ricin Or High-Dose Cytarabine: Cancer And Leukemia Group B Study 9311*," Cancer 97:1471-1480.

Takemura, S. et al. (2000) "*Construction of A Diabody (Small Recombinant Bispecific Antibody) Using A Refolding System*," Protein Eng. 13(8):583-588.

Tedder, T.F. (2009) "*CD19: A Promising B Cell Target for Rheumatoid Arthritis*," Nat. Rev. Rheumatol. 5:572-577.

Tedder, T.F. et al. (1989) "*Isolation of cDNAs Encoding The CD19 Antigen of Human And Mouse B Lymphocytes. A New Member of The Immunoglobulin Superfamily*," J. Immunol. 143(2):712-717.

Thomas, D.A. et al. (2010) "*Chemoimmunotherapy With a Modified Hyper-CVAD And Rituximab Regimen Improves Outcome in De Novo Philadelphia Chromosome-Negative Precursor B-Lineage Acute Lymphoblastic Leukemia*," J. Clin. Oncol. 28(24):3880-3889.

Thomas, S. et al. (2010) "*Molecular Immunology Lessons from Therapeutic T-Cell Receptor Gene Transfer*," Immunology 129(2):170-177.

Topp, M.S. et al. (2011) "*Targeted Therapy with the T-Cell-Engaging Antibody Blinatumomab of Chemotherapy-Refractory Minimal Residual Disease In B-Lineage Acute Lymphoblastic Leukemia Patients Results in High Response Rate and Prolonged Leukemia-Free Survival*," J. Clin. Oncol. 29(18):2493-2498.

Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362.

Veri, M.C. et al. (2010) "*Therapeutic Control of B Cell Activation Via Recruitment of Fcγ Receptor IIb (CD32B) Inhibitory Function with A Novel Bispecific Antibody Scaffold*," Arthritis Rheum. 62(7):1933-1943.

Wang K. et al. (2012) "*CD19: A Biomarker for B Cell Development, Lymphoma Diagnosis and Therapy*," Exp. Hematol. and Oncol. 1:36.

Wilson, K. et al. (2010) "*Flow Minimal Residual Disease Monitoring Of Candidate Leukemic Stem Cells Defined By The Immunophenotype, CD34+CD38lowCD19+ In B-Lineage Childhood Acute Lymphoblastic Leukemia*," Haematologica 95(4):679-683.

Woolfson D.N. (2005) "*The Design of Coiled-Coil Structures and Assemblies*," Adv. Prot. Chem. 70:79-112.

Written Opinion of the International Searching Authority PCT/US2015/051314 (WO 2016/048938) (10 pages).

Wu G.Y. et al. (1987) "*Receptor-Mediated In Vitro Gene Transformation by A Soluble DNA Carrier System*," J. Biol. Chem. 262:4429-4432.

Wu, A. et al. (2001) "*Multimerization of a Chimeric Anti-CD20 Single Chain Fv-Fv Fusion Protein is Mediated Through Variable Domain Exchange*," Protein Eng. 14(2):1025-1033.

Wucherpfennig, K.W. et al. (2010) "*Structural Biology of the T-Cell Receptor: Insights into Receptor Assembly, Ligand Recognition, and Initiation of Signaling*," Cold Spring Harb. Perspect. Biol. 2(4):a005140; pp. 1-14.

Xie Z. et al. (2005) "*A New Format of Bispecific Antibody: Highly Efficient Heterodimerization, Expression and Tumor Cell Lysis*," J. Immunol. Methods 296:95-101.

Zeng, Y. et al. (2008) "*A Ligand-Pseudoreceptor System Based On de novo Designed Peptides for The Generation of Adenoviral Vectors With Altered Tropism*," J. Gene Med. 10:355-367.

Zhou, L.J. et al. (1991) "*Structure and Domain Organization of The CD19 Antigen of Human, Mouse, and Guinea Pig B Lymphocytes. Conservation of The Extensive Cytoplasmic Domain*," J. Immunol. 147(4):1424-1432.

Zhukovsky E.A. et al. (2013) "*A CD19/CD3 Bispecific Tandab, AFM11, Recruits T Cells to Potently and Safely Kill CD19+ Tumor Cells*," J Clin Oncol 31, 2013 (suppl; abstr 3068).

\* cited by examiner

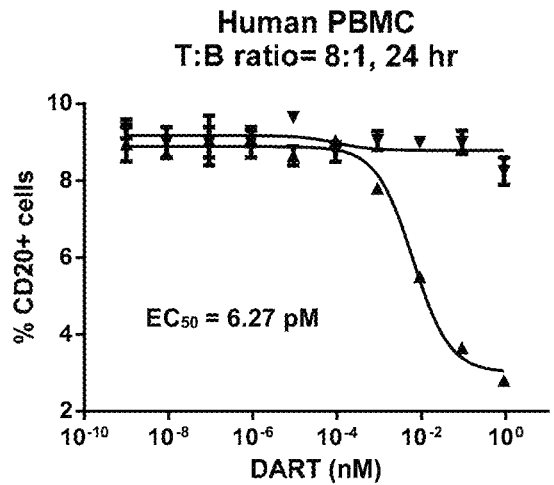
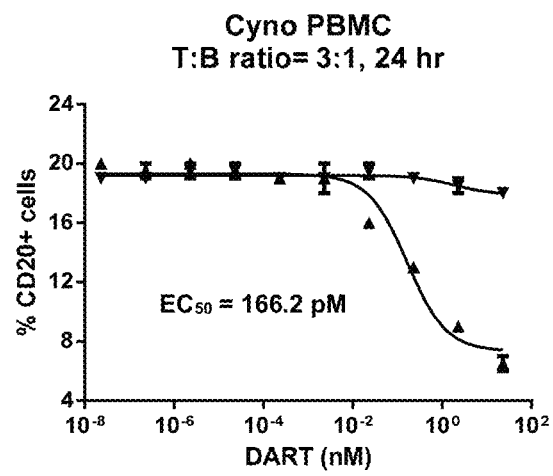
Figure 9A    Figure 9B
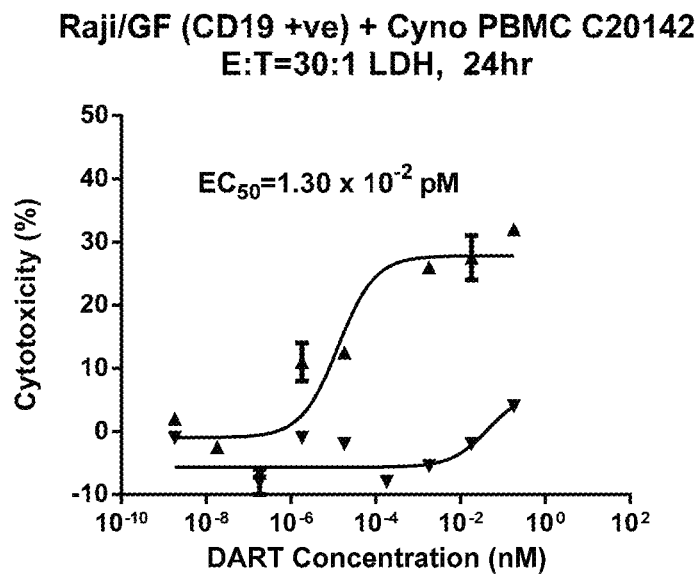
Figure 10

Granzyme B

Perforin

SEQUENCE LISTING

```
<160> NUMBER OF SEQ ID NOS: 48

<210> SEQ ID NO 1
<211> LENGTH: 8
<212> TYPE: PRT
<213> ORGANISM: Artificial Sequence
<220> FEATURE:
<223> OTHER INFORMATION: Intervening Spacer Peptide (Linker 1)

<400> SEQUENCE: 1

Gly Gly Gly Ser Gly Gly Gly Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Linker 2

<400> SEQUENCE: 2

Ala Ser Thr Lys Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Cysteine-Containing Linker

<400> SEQUENCE: 3
```

```
Gly Gly Cys Gly Gly Gly
1               5

<210> SEQ ID NO 4
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: IgG1 Hinge Domain

<400> SEQUENCE: 4

Asp Lys Thr His Thr Cys Pro Pro Cys Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Spacer-Linker 3

<400> SEQUENCE: 5

Gly Gly Gly Asp Lys Thr His Thr Cys Pro Pro Cys Pro
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 6

Gly Val Glu Pro Lys Ser Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Heterodimer-Promoting Domain

<400> SEQUENCE: 7

Val Glu Pro Lys Ser Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Heterodimer-Promoting Domain

<400> SEQUENCE: 8

Gly Phe Asn Arg Gly Glu Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Heterodimer-Promoting Domain
```

```
<400> SEQUENCE: 9

Phe Asn Arg Gly Glu Cys
1               5

<210> SEQ ID NO 10
<211> LENGTH: 28
<212> TYPE: PRT
<213> ORGANISM: Artificial Sequence
<220> FEATURE:
<223> OTHER INFORMATION: E-coil Heterodimer-Promoting Domain

<400> SEQUENCE: 10

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: K-coil Heterodimer-Promoting Domain

<400> SEQUENCE: 11

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 12
<211> LENGTH: 28
<212> TYPE: PRT
<213> ORGANISM: Artificial Sequence
<220> FEATURE:
<223> OTHER INFORMATION: Cysteine-Containing E-coil Heterodimer-
      Promoting Domain

<400> SEQUENCE: 12

Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 13
<211> LENGTH: 28
<212> TYPE: PRT
<213> ORGANISM: Artificial Sequence
<220> FEATURE:
<223> OTHER INFORMATION: Cysteine-Containing K-coil Heterodimer-
      Promoting Domain

<400> SEQUENCE: 13

Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 14
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
```

<223> OTHER INFORMATION: CH2-CH3 Domain of Human IgG1

<400> SEQUENCE: 14

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 15
<211> LENGTH: 217
<212> TYPE: PRT
<213> ORGANISM: Artificial Sequence
<220> FEATURE:
<223> OTHER INFORMATION: "Knob-Bearing" CH2-CH3 Domain

<400> SEQUENCE: 15

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125
```

```
Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 16
<211> LENGTH: 217
<212> TYPE: PRT
<213> ORGANISM: Artificial Sequence
<220> FEATURE:
<223> OTHER INFORMATION: "Hole-Bearing" CH2-CH3 Domain

<400> SEQUENCE: 16

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Lys
    210                 215
```

<210> SEQ ID NO 17
<211> LENGTH: 106
<212> TYPE: PRT
<213> ORGANISM: Artificial Sequence
<220> FEATURE:
<223> OTHER INFORMATION: Variable Light Chain of Anti-CD19 Antibody

<400> SEQUENCE: 17

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
                20                  25                  30

His Trp Tyr Gln Gln Lys Pro Gly Gln Ala Pro Arg Leu Leu Ile Tyr
            35                  40                  45

Asp Ala Ser Asn Arg Ala Ser Gly Val Pro Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys
            100                 105

<210> SEQ ID NO 18
<211> LENGTH: 10
<212> TYPE: PRT
<213> ORGANISM: Artificial Sequence
<220> FEATURE:
<223> OTHER INFORMATION: CDR1 of Variable Light Chain of Anti-CD19
      Antibody

<400> SEQUENCE: 18

Arg Ala Ser Gln Ser Val Ser Tyr Met His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDR2 of Variable Light Chain of Anti-CD19
      Antibody

<400> SEQUENCE: 19

Asp Ala Ser Asn Arg Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: CDR3 of Variable Light Chain of Anti-CD19
      Antibody

<400> SEQUENCE: 20

Phe Gln Gly Ser Val Tyr Pro Phe Thr
1               5

<210> SEQ ID NO 21
<211> LENGTH: 120
<212> TYPE: PRT
<213> ORGANISM: Artificial Sequence
<220> FEATURE:
<223> OTHER INFORMATION: Variable Heavy Chain of Anti-CD19 Antibody

<400> SEQUENCE: 21

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser

```
                20                  25                  30
Gly Met Gly Val Gly Trp Ile Arg Gln Pro Pro Gly Lys Ala Leu Glu
            35                  40                  45

Trp Leu Ala His Ile Trp Trp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Phe Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Thr Val Thr Val Ser Ser
            115                 120

<210> SEQ ID NO 22
<211> LENGTH: 7
<212> TYPE: PRT
<213> ORGANISM: Artificial Sequence
<220> FEATURE:
<223> OTHER INFORMATION: CDR1 of Variable Heavy Chain of Anti-CD19
      Antibody

<400> SEQUENCE: 22

Thr Ser Gly Met Gly Val Gly
1               5

<210> SEQ ID NO 23
<211> LENGTH: 16
<212> TYPE: PRT
<213> ORGANISM: Artificial Sequence
<220> FEATURE:
<223> OTHER INFORMATION: CDR2 of Variable Heavy Chain of Anti-CD19
      Antibody

<400> SEQUENCE: 23

His Ile Trp Trp Asp Asp Lys Arg Tyr Asn Pro Ala Leu Lys Ser
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: CDR3 of Variable Heavy Chain of Anti-CD19
      Antibody

<400> SEQUENCE: 24

Met Glu Leu Trp Ser Tyr Tyr Phe Asp Tyr
1               5                   10

<210> SEQ ID NO 25
<211> LENGTH: 110
<212> TYPE: PRT
<213> ORGANISM: Artificial Sequence
<220> FEATURE:
<223> OTHER INFORMATION: Variable Light Chain of Anti-CD3 Antibody

<400> SEQUENCE: 25

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
```

```
                    35                  40                  45
Leu Ile Gly Gly Thr Asn Lys Arg Ala Pro Trp Thr Pro Ala Arg Phe
                50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly
            100                 105                 110

<210> SEQ ID NO 26
<211> LENGTH: 14
<212> TYPE: PRT
<213> ORGANISM: Artificial Sequence
<220> FEATURE:
<223> OTHER INFORMATION: CDR1 of Variable Light Chain of Anti-CD3
      Antibody

<400> SEQUENCE: 26

Arg Ser Ser Thr Gly Ala Val Thr Thr Ser Asn Tyr Ala Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: CDR2 of Variable Light Chain of Anti-CD3
      Antibody

<400> SEQUENCE: 27

Gly Thr Asn Lys Arg Ala Pro
1               5

<210> SEQ ID NO 28
<211> LENGTH: 9
<212> TYPE: PRT
<213> ORGANISM: Artificial Sequence
<220> FEATURE:
<223> OTHER INFORMATION: CDR3 of Variable Light Chain of Anti-CD3
      Antibody

<400> SEQUENCE: 28

Ala Leu Trp Tyr Ser Asn Leu Trp Val
1               5

<210> SEQ ID NO 29
<211> LENGTH: 125
<212> TYPE: PRT
<213> ORGANISM: Artificial Sequence
<220> FEATURE:
<223> OTHER INFORMATION: Variable Heavy Chain of Anti-CD3 Antibody

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Gly Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ser Lys Asn Ser
```

```
                65                  70                  75                  80
Leu Tyr Leu Gln Met Asn Ser Leu Lys Thr Glu Asp Thr Ala Val Tyr
                    85                  90                  95

Tyr Cys Val Arg His Gly Asn Phe Gly Asn Ser Tyr Val Ser Trp Phe
                   100                 105                 110

Ala Tyr Trp Gly Gln Gly Thr Leu Val Thr Val Ser Ser
        115                 120                 125
```

<210> SEQ ID NO 30
<211> LENGTH: 5
<212> TYPE: PRT
<213> ORGANISM: Artificial Sequence
<220> FEATURE:
<223> OTHER INFORMATION: CDR1 of Variable Heavy Chain of Anti-CD3
      Antibody

<400> SEQUENCE: 30

```
Thr Tyr Ala Met Asn
1               5
```

<210> SEQ ID NO 31
<211> LENGTH: 19
<212> TYPE: PRT
<213> ORGANISM: Artificial Sequence
<220> FEATURE:
<223> OTHER INFORMATION: CDR2 of Variable Heavy Chain of Anti-CD3
      Antibody

<400> SEQUENCE: 31

```
Arg Ile Arg Ser Lys Tyr Asn Asn Tyr Ala Thr Tyr Tyr Ala Asp Ser
1               5                   10                  15

Val Lys Gly
```

<210> SEQ ID NO 32
<211> LENGTH: 14
<212> TYPE: PRT
<213> ORGANISM: Artificial Sequence
<220> FEATURE:
<223> OTHER INFORMATION: CDR3 of Variable Heavy Chain of Anti-CD3
      Antibody

<400> SEQUENCE: 32

```
His Gly Asn Phe Gly Asn Ser Tyr Val Ser Trp Phe Ala Tyr
1               5                   10
```

<210> SEQ ID NO 33
<211> LENGTH: 4
<212> TYPE: PRT
<213> ORGANISM: Artificial Sequence
<220> FEATURE:
<223> OTHER INFORMATION: Linker 4

<400> SEQUENCE: 33

```
Gly Gly Gly Ser
1
```

<210> SEQ ID NO 34
<211> LENGTH: 46
<212> TYPE: PRT
<213> ORGANISM: Artificial Sequence
<220> FEATURE:
<223> OTHER INFORMATION: Albumin-Binding Domain (ABD)

<400> SEQUENCE: 34

```
Leu Ala Glu Ala Lys Val Leu Ala Asn Arg Glu Leu Asp Lys Tyr Gly
```

```
                1               5                   10                  15
            Val Ser Asp Tyr Tyr Lys Asn Leu Ile Asp Asn Ala Lys Ser Ala Glu
                            20                  25                  30
            Gly Val Lys Ala Leu Ile Asp Glu Ile Leu Ala Ala Leu Pro
                            35                  40                  45

<210> SEQ ID NO 35
<211> LENGTH: 502
<212> TYPE: PRT
<213> ORGANISM: Artificial Sequence
<220> FEATURE:
<223> OTHER INFORMATION: First Polypeptide Chain of DART-A

<400> SEQUENCE: 35

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
                20                  25                  30

His Trp Tyr Gln Gln Lys Pro Gly Gln Ala Pro Arg Leu Leu Ile Tyr
            35                  40                  45

Asp Ala Ser Asn Arg Ala Ser Gly Val Pro Ser Arg Phe Ser Gly Ser
        50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Gln Leu Val Glu Ser Gly Gly Gly Leu Val Gln Pro
        115                 120                 125

Gly Gly Ser Leu Arg Leu Ser Cys Ala Ala Ser Gly Phe Thr Phe Ser
130                 135                 140

Thr Tyr Ala Met Asn Trp Val Arg Gln Ala Pro Gly Lys Gly Leu Glu
145                 150                 155                 160

Trp Val Gly Arg Ile Arg Ser Lys Tyr Asn Asn Tyr Ala Thr Tyr Tyr
                165                 170                 175

Ala Asp Ser Val Lys Gly Arg Phe Thr Ile Ser Arg Asp Asp Ser Lys
            180                 185                 190

Asn Ser Leu Tyr Leu Gln Met Asn Ser Leu Lys Thr Glu Asp Thr Ala
        195                 200                 205

Val Tyr Tyr Cys Val Arg His Gly Asn Phe Gly Asn Ser Tyr Val Ser
    210                 215                 220

Trp Phe Ala Tyr Trp Gly Gln Gly Thr Leu Val Thr Val Ser Ser Ala
225                 230                 235                 240

Ser Thr Lys Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Gly Gly Gly Asp Lys Thr His Thr Cys Pro Pro Cys Pro Ala Pro Glu
        275                 280                 285

Ala Ala Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
```

325                 330                 335
Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Ala Leu Pro
            370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Glu Glu Met Thr Lys Asn
                405                 410                 415

Gln Val Ser Leu Trp Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
            450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys
            500

<210> SEQ ID NO 36
<211> LENGTH: 1506
<212> TYPE: DNA
<213> ORGANISM: Artificial Sequence
<220> FEATURE:
<223> OTHER INFORMATION: Polynucleotide Encoding DART-A (SEQ ID NO:35)

<400> SEQUENCE: 36
gagaatgtgc tcacacagtc ccctgcaact ctgagcgtaa ctccagggga gaaggccacc      60
atcacgtgta gagcctccca gagtgtgagc tacatgcact ggtatcagca gaaacctgga     120
caagctccca ggttgctgat ctatgacgcg agcaaccggg ctagtggcgt tccatcccgg     180
ttttctggct caggatctgg cactgaccac accctcacca tatccagcct tgaagccgaa     240
gatgccgcaa cctactactg ctttcagggg agtgtgtatc ccttcacatt cggtcagggt     300
acaaagctgg agattaaggg tggaggatcc ggcggcggag gcgaggtgca gctggtggag     360 tctggggag gcttggtcca gcctggaggg tccctgagac tctcctgtgc agcctctgga     420
ttcaccttca gcacatacgc tatgaattgg gtccgccagg ctccagggaa ggggctggag     480
tgggttggaa ggatcaggtc caagtacaac aattatgcaa cctactatgc cgactctgtg     540
aagggtagat tcaccatctc aagagatgat tcaaagaact cactgtatct gcaaatgaac     600
agcctgaaaa ccgaggacac ggccgtgtat tactgtgtga cacggtaa ctcggcaat      660 tcttacgtgt cttggtttgc ttattgggga caggggacac tggtgactgt gtcttccgcc     720
tccaccaagg gcgaagtggc cgcatgtgag aaagaggttg ctgctttgga aaggaggtc     780 gctgcacttg aaaaggaggt cgcagccctg gagaaaggcg cggggacaa aactcacaca     840 tgcccaccgt gcccagcacc tgaagccgcg ggggaccgt cagtcttcct cttccccca     900 aaacccaagg acaccctcat gatctcccgg acccctgagg tcacatgcgt ggtggtggac    960
gtgagccacg aagaccctga ggtcaagttc aactggtacg tggacggcgt ggaggtgcat    1020

```
aatgccaaga caaagccgcg ggaggagcag tacaacagca cgtaccgtgt ggtcagcgtc    1080
ctcaccgtcc tgcaccagga ctggctgaat ggcaaggagt acaagtgcaa ggtctccaac    1140
aaagccctcc cagcccccat cgagaaaacc atctccaaag ccaaagggca gccccgagaa    1200
ccacaggtgt acaccctgcc cccatcccgg gaggagatga ccaagaacca ggtcagcctg    1260
tggtgcctgg tcaaaggctt ctatcccagc gacatcgccg tggagtggga gagcaatggg    1320
cagccggaga acaactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggtaaa                                                               1506
```

<210> SEQ ID NO 37
<211> LENGTH: 271
<212> TYPE: PRT
<213> ORGANISM: Artificial Sequence
<220> FEATURE:
<223> OTHER INFORMATION: Second Polypeptide Chain of DART-A

<400> SEQUENCE: 37

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Gln Val Thr Leu Arg Glu Ser Gly Pro Ala
        115                 120                 125

Leu Val Lys Pro Thr Gln Thr Leu Thr Leu Thr Cys Thr Phe Ser Gly
    130                 135                 140

Phe Ser Leu Ser Thr Ser Gly Met Gly Val Gly Trp Ile Arg Gln Pro
145                 150                 155                 160

Pro Gly Lys Ala Leu Glu Trp Leu Ala His Ile Trp Trp Asp Asp Asp
                165                 170                 175

Lys Arg Tyr Asn Pro Ala Leu Lys Ser Arg Leu Thr Ile Ser Lys Asp
            180                 185                 190

Thr Ser Lys Asn Gln Val Phe Leu Thr Met Thr Asn Met Asp Pro Val
        195                 200                 205

Asp Thr Ala Thr Tyr Tyr Cys Ala Arg Met Glu Leu Trp Ser Tyr Tyr
    210                 215                 220

Phe Asp Tyr Trp Gly Gln Gly Thr Thr Val Thr Val Ser Ser Ala Ser
225                 230                 235                 240

Thr Lys Gly Lys Val Ala Ala Cys Lys Glu Lys Val Ala Ala Leu Lys
                245                 250                 255

Glu Lys Val Ala Ala Leu Lys Glu Lys Val Ala Ala Leu Lys Glu
            260                 265                 270
```

<210> SEQ ID NO 38
<211> LENGTH: 813
<212> TYPE: DNA
<213> ORGANISM: Artificial Sequence
<220> FEATURE:
<223> OTHER INFORMATION: Polynucleotide Encoding Second Polypeptide
      Chain of DART-A (SEQ ID NO:37)

<400> SEQUENCE: 38

```
caggctgtgg tgactcagga gccttcactg accgtgtccc caggcggaac tgtgaccctg      60
acatgcagat ccagcacagg cgcagtgacc acatctaact acgccaattg ggtgcagcag     120
aagccaggac aggcaccaag gggcctgatc gggggtacaa acaaaagggc tccctggacc     180
cctgcacggt tttctggaag tctgctgggc ggaaaggccg ctctgactat taccggggca     240
caggccgagg acgaagccga ttactattgt gctctgtggt atagcaatct gtgggtgttc     300
gggggtggca caaaactgac tgtgctggga ggggtggat ccggcggagg tggacaggtg     360
acactgaggg aatctggtcc agctctggtg aaacccactc agacgctcac tctcacttgc     420
acctttagtg ggttctcact gtccacatct ggcatgggag taggctggat tcgacagcca     480
cctgggaaag ccttggagtg gcttgcccac atctggtggg atgacgacaa gcggtataat     540
cccgcactga agagcagact gaccatcagc aaggatacat ccaagaacca ggtgtttctg     600
accatgacca catggaccc tgtcgataca gccaccctact attgtgctcg catggagttg     660
tggtcctact acttcgacta ttggggacaa ggcacaaccg tgactgtctc atccgcctcc     720
accaagggca agtggccgc atgtaaggag aaagttgctg ctttgaaaga gaaggtcgcc     780
gcacttaagg aaaaggtcgc agccctgaaa gag                                   813
```

<210> SEQ ID NO 39
<211> LENGTH: 227
<212> TYPE: PRT
<213> ORGANISM: Artificial Sequence
<220> FEATURE:
<223> OTHER INFORMATION: Third Polypeptide Chain of DART-A

<400> SEQUENCE: 39

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
            165                 170                 175

Val Leu Asp Ser Asp Gly Ser Phe Phe Leu Val Ser Lys Leu Thr Val
        180                 185                 190

Asp Lys Ser Arg Trp Gln Gln Gly Asn Val Phe Ser Cys Ser Val Met
    195                 200                 205

His Glu Ala Leu His Asn Arg Tyr Thr Gln Lys Ser Leu Ser Leu Ser
210                 215                 220

Pro Gly Lys
225

<210> SEQ ID NO 40
<211> LENGTH: 681
<212> TYPE: DNA
<213> ORGANISM: Artificial Sequence
<220> FEATURE:
<223> OTHER INFORMATION: Polynucleotide Encoding Third Polypeptide Chain
      of DART-A

<400> SEQUENCE: 40
gacaaaactc acacatgccc accgtgccca gcacctgaag ccgcggggg accgtcagtc      60 ttcctcttcc cccaaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcgggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggagga gatgaccaag    420
aaccaggtca gcctgagttg cgcagtcaaa ggcttctatc ccagcgacat cgccgtggag    480
tgggagagca atgggcagcc ggagaacaac tacaagacca cgcctcccgt gctggactcc    540
gacggctcct tcttcctcgt cagcaagctc accgtggaca agagcaggtg gcagcagggg    600
aacgtcttct catgctccgt gatgcatgag gctctgcaca accgctacac gcagaagagc    660
ctctccctgt ctccgggtaa a                                              681

<210> SEQ ID NO 41
<211> LENGTH: 112
<212> TYPE: PRT
<213> ORGANISM: Artificial Sequence
<220> FEATURE:
<223> OTHER INFORMATION: Variable Light Chain Domain of Anti-Fluorescein
      Antibody 4-4-20

<400> SEQUENCE: 41

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95
```

```
Thr His Val Pro Trp Thr Phe Gly Gly Gly Thr Lys Leu Glu Ile Lys
            100                 105                 110
```

<210> SEQ ID NO 42
<211> LENGTH: 118
<212> TYPE: PRT
<213> ORGANISM: Artificial Sequence
<220> FEATURE:
<223> OTHER INFORMATION: Variable Heavy Chain Domain Of Anti-Fluorescein
      Antibody 4-4-20

<400> SEQUENCE: 42

```
Glu Val Lys Leu Asp Glu Thr Gly Gly Gly Leu Val Gln Pro Gly Arg
1               5                   10                  15

Pro Met Lys Leu Ser Cys Val Ala Ser Gly Phe Thr Phe Ser Asp Tyr
            20                  25                  30

Trp Met Asn Trp Val Arg Gln Ser Pro Glu Lys Gly Leu Glu Trp Val
        35                  40                  45

Ala Gln Ile Arg Asn Lys Pro Tyr Asn Tyr Glu Thr Tyr Tyr Ser Asp
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
            100                 105                 110

Ser Val Thr Val Ser Ser
        115
```

<210> SEQ ID NO 43
<211> LENGTH: 508
<212> TYPE: PRT
<213> ORGANISM: Artificial Sequence
<220> FEATURE:
<223> OTHER INFORMATION: First Polypeptide Chain of Control DART 1

<400> SEQUENCE: 43

```
Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Ser Gly Gly Gly Gly Glu Val Gln Leu Val Glu Ser Gly
        115                 120                 125

Gly Gly Leu Val Gln Pro Gly Ser Leu Arg Leu Ser Cys Ala Ala
    130                 135                 140

Ser Gly Phe Thr Phe Ser Thr Tyr Ala Met Asn Trp Val Arg Gln Ala
145                 150                 155                 160

Pro Gly Lys Gly Leu Glu Trp Val Gly Arg Ile Arg Ser Lys Tyr Asn
```

```
                    165                 170                 175
Asn Tyr Ala Thr Tyr Ala Asp Ser Val Lys Gly Arg Phe Thr Ile
                180                 185                 190

Ser Arg Asp Asp Ser Lys Asn Ser Leu Tyr Leu Gln Met Asn Ser Leu
            195                 200                 205

Lys Thr Glu Asp Thr Ala Val Tyr Tyr Cys Val Arg His Gly Asn Phe
        210                 215                 220

Gly Asn Ser Tyr Val Ser Trp Phe Ala Tyr Trp Gly Gln Gly Thr Leu
225                 230                 235                 240

Val Thr Val Ser Ser Ala Ser Thr Lys Gly Glu Val Ala Ala Cys Glu
                245                 250                 255

Lys Glu Val Ala Ala Leu Glu Lys Glu Val Ala Ala Leu Glu Lys Glu
                260                 265                 270

Val Ala Ala Leu Glu Lys Gly Gly Gly Asp Lys Thr His Thr Cys Pro
                275                 280                 285

Pro Cys Pro Ala Pro Glu Ala Ala Gly Gly Pro Ser Val Phe Leu Phe
            290                 295                 300

Pro Pro Lys Pro Lys Asp Thr Leu Met Ile Ser Arg Thr Pro Glu Val
305                 310                 315                 320

Thr Cys Val Val Val Asp Val Ser His Glu Asp Pro Glu Val Lys Phe
                325                 330                 335

Asn Trp Tyr Val Asp Gly Val Glu Val His Asn Ala Lys Thr Lys Pro
            340                 345                 350

Arg Glu Glu Gln Tyr Asn Ser Thr Tyr Arg Val Val Ser Val Leu Thr
        355                 360                 365

Val Leu His Gln Asp Trp Leu Asn Gly Lys Glu Tyr Lys Cys Lys Val
    370                 375                 380

Ser Asn Lys Ala Leu Pro Ala Pro Ile Glu Lys Thr Ile Ser Lys Ala
385                 390                 395                 400

Lys Gly Gln Pro Arg Glu Pro Gln Val Tyr Thr Leu Pro Pro Ser Arg
                405                 410                 415

Glu Glu Met Thr Lys Asn Gln Val Ser Leu Trp Cys Leu Val Lys Gly
            420                 425                 430

Phe Tyr Pro Ser Asp Ile Ala Val Glu Trp Glu Ser Asn Gly Gln Pro
        435                 440                 445

Glu Asn Asn Tyr Lys Thr Thr Pro Pro Val Leu Asp Ser Asp Gly Ser
    450                 455                 460

Phe Phe Leu Tyr Ser Lys Leu Thr Val Asp Lys Ser Arg Trp Gln Gln
465                 470                 475                 480

Gly Asn Val Phe Ser Cys Ser Val Met His Glu Ala Leu His Asn His
                485                 490                 495

Tyr Thr Gln Lys Ser Leu Ser Leu Ser Pro Gly Lys
            500                 505

<210> SEQ ID NO 44
<211> LENGTH: 269
<212> TYPE: PRT
<213> ORGANISM: Artificial Sequence
<220> FEATURE:
<223> OTHER INFORMATION: Second Polypeptide Chain of Control DART 1

<400> SEQUENCE: 44

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
```

```
                    20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Trp Thr Pro Ala Arg Phe
        50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Ala Ser Thr Lys
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 45
<211> LENGTH: 495
<212> TYPE: PRT
<213> ORGANISM: Artificial Sequence
<220> FEATURE:
<223> OTHER INFORMATION: Frst Polypeptide Chain of Control DART 2

<400> SEQUENCE: 45

Glu Asn Val Leu Thr Gln Ser Pro Ala Thr Leu Ser Val Thr Pro Gly
1               5                   10                  15

Glu Lys Ala Thr Ile Thr Cys Arg Ala Ser Gln Ser Val Ser Tyr Met
            20                  25                  30

His Trp Tyr Gln Gln Lys Pro Gly Gln Ala Pro Arg Leu Leu Ile Tyr
        35                  40                  45

Asp Ala Ser Asn Arg Ala Ser Gly Val Pro Ser Arg Phe Ser Gly Ser
    50                  55                  60

Gly Ser Gly Thr Asp His Thr Leu Thr Ile Ser Ser Leu Glu Ala Glu
65                  70                  75                  80

Asp Ala Ala Thr Tyr Tyr Cys Phe Gln Gly Ser Val Tyr Pro Phe Thr
                85                  90                  95

Phe Gly Gln Gly Thr Lys Leu Glu Ile Lys Gly Gly Gly Ser Gly Gly
            100                 105                 110

Gly Gly Glu Val Lys Leu Asp Glu Thr Gly Gly Gly Leu Val Gln Pro
```

```
            115                 120                 125
Gly Arg Pro Met Lys Leu Ser Cys Val Ala Ser Gly Phe Thr Phe Ser
130                 135                 140

Asp Tyr Trp Met Asn Trp Val Arg Gln Ser Pro Glu Lys Gly Leu Glu
145                 150                 155                 160

Trp Val Ala Gln Ile Arg Asn Lys Pro Tyr Asn Tyr Glu Thr Tyr Tyr
                165                 170                 175

Ser Asp Ser Val Lys Gly Arg Phe Thr Ile Ser Arg Asp Asp Ser Lys
            180                 185                 190

Ser Ser Val Tyr Leu Gln Met Asn Asn Leu Arg Val Glu Asp Met Gly
        195                 200                 205

Ile Tyr Tyr Cys Thr Gly Ser Tyr Tyr Gly Met Asp Tyr Trp Gly Gln
    210                 215                 220

Gly Thr Ser Val Thr Val Ser Ser Ala Ser Thr Lys Gly Glu Val Ala
225                 230                 235                 240

Ala Cys Glu Lys Glu Val Ala Ala Leu Glu Lys Glu Val Ala Ala Leu
                245                 250                 255

Glu Lys Glu Val Ala Ala Leu Glu Lys Gly Gly Gly Asp Lys Thr His
            260                 265                 270

Thr Cys Pro Pro Cys Pro Ala Pro Glu Ala Ala Gly Gly Pro Ser Val
        275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Glu Glu Met Thr Lys Asn Gln Val Ser Leu Trp Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495

<210> SEQ ID NO 46
<211> LENGTH: 269
<212> TYPE: PRT
<213> ORGANISM: Artificial Sequence
<220> FEATURE:
<223> OTHER INFORMATION: Second Polypeptide Chain of Control DART 2
```

<400> SEQUENCE: 46

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu Gly Gly Gly
            100                 105                 110

Gly Ser Gly Gly Gly Gly Glu Val Lys Leu Asp Glu Thr Gly Gly Gly
        115                 120                 125

Leu Val Gln Pro Gly Arg Pro Met Lys Leu Ser Cys Val Ala Ser Gly
    130                 135                 140

Phe Thr Phe Ser Asp Tyr Trp Met Asn Trp Val Arg Gln Ser Pro Glu
145                 150                 155                 160

Lys Gly Leu Glu Trp Val Ala Gln Ile Arg Asn Lys Pro Tyr Asn Tyr
                165                 170                 175

Glu Thr Tyr Tyr Ser Asp Ser Val Lys Gly Arg Phe Thr Ile Ser Arg
            180                 185                 190

Asp Asp Ser Lys Ser Ser Val Tyr Leu Gln Met Asn Asn Leu Arg Val
        195                 200                 205

Glu Asp Met Gly Ile Tyr Tyr Cys Thr Gly Ser Tyr Tyr Gly Met Asp
    210                 215                 220

Tyr Trp Gly Gln Gly Thr Ser Val Thr Val Ser Ser Ala Ser Thr Lys
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265
```

<210> SEQ ID NO 47
<211> LENGTH: 5
<212> TYPE: PRT
<213> ORGANISM: Artificial Sequence
<220> FEATURE:
<223> OTHER INFORMATION: Intervening Spacer Peptide (Linker 4)

<400> SEQUENCE: 47

```
Ala Pro Ser Ser Ser
1               5
```

<210> SEQ ID NO 48
<211> LENGTH: 8
<212> TYPE: PRT
<213> ORGANISM: Artificial Sequence
<220> FEATURE:
<223> OTHER INFORMATION: Intervening Spacer Peptide (Linker 4)

<400> SEQUENCE: 48

```
Ala Pro Ser Ser Ser Pro Met Glu
1               5
```

BI-SPECIFIC MONOVALENT DIABODIES THAT ARE CAPABLE OF BINDING CD19 AND CD3, AND USES THEREOF

CROSS-REFERENCE TO RELATED APPLICATIONS

This application is a divisional of U.S. patent application Ser. No. 15/514,334 (filed Mar. 24, 2017), which application is a § 371 National Stage Application of PCT/US2015/051314 (filed Sep. 22, 2015), which application claims priority to U.S. Provisional Patent Application Ser. No. 62/055,695 (filed Sep. 26, 2014), which applications are incorporated herein by reference in their entireties.

REFERENCE TO SEQUENCE LISTING

This application includes one or more Sequence Listings pursuant to 37 C.F.R. 1.821 et seq., which are disclosed in computer-readable media (file name: 1301_0116PCT_Sequence_Listing_ST25.txt, created on Sep. 18, 2015, and having a size of 47,329 bytes), which file is herein incorporated by reference in its entirety.

FIELD OF THE INVENTION

The present invention is directed to bi-specific monovalent diabodies that comprise two polypeptide chains and which possess one binding site specific for an epitope of CD19 and one binding site specific for an epitope of CD3 (i.e., a "CD19×CD3 bi-specific monovalent diabody"). Most preferably, such CD19×CD3 bi-specific monovalent diabodies are composed of three polypeptide chains and possess one binding site specific for an epitope of CD19 and one binding site specific for an epitope of CD3 and additionally comprise an immunoglobulin Fc Domain (i.e., a "CD19×CD3 bi-specific monovalent Fc diabody"). The bi-specific monovalent diabodies and bi-specific monovalent Fc diabodies of the present invention are capable of simultaneous binding to CD19 and CD3. The invention is directed to pharmaceutical compositions that contain such bi-specific monovalent diabodies or such bi-specific monovalent Fc diabodies. The invention is additionally directed to methods for the use of such diabodies in the treatment of disease, in particular hematologic malignancies.

BACKGROUND OF THE INVENTION

A. CD19

CD19 (B lymphocyte surface antigen B4, Genbank accession number M28170) is a 95 kDa type I transmembrane glycoprotein of the immunoglobulin superfamily (Stamenkovic, I. et al. (1988) "*CD19, The Earliest Differentiation Antigen Of The B Cell Lineage, Bears Three Extracellular Immunoglobulin-Like Domains And An Epstein-Barr Virus-Related Cytoplasmic Tail*," J. Exper. Med. 168(3):1205-1210; Tedder, T. F. et al. (1989) "*Isolation Of cDNAs Encoding The CD19 Antigen Of Human And Mouse B Lymphocytes. A New Member Of The Immunoglobulin Superfamily*," J. Immunol. 143(2):712-717; Zhou, L. J. et al. (1991) "*Structure And Domain Organization Of The CD19 Antigen Of Human, Mouse, And Guinea Pig B Lymphocytes. Conservation Of The Extensive Cytoplasmic Domain*," J. Immunol. 147(4):1424-1432). CD19 is expressed on follicular dendritic cells and on all B cells from early pre-B cells at the time of heavy chain rearrangement up to the plasma cell stage, when CD19 expression is down regulated. CD19 is not expressed on hematopoietic stem cells or on B cells before the pro-B cell stage (Sato et al. (1995) "*The CD19 Signal Transduction Molecule Is A Response Regulator Of B-Lymphocyte Differentiation*," Proc. Natl. Acad. Sci. (U.S.A.) 92:11558-62; Loken et al. (1987) "*Flow Cytometric Analysis of Human Bone Marrow. II. Normal B Lymphocyte Development*," Blood, 70:1316-1324; Wang et al. (2012) "*CD19: A Biomarker For B Cell Development, Lymphoma Diagnosis And Therapy*," Exp. Hematol. and Oncol. 1:36).

CD19 is a component of the B cell-receptor (BCR) complex, and is a positive regulator of B cell signaling that modulates the threshold for B cell activation and humoral immunity. CD19 interacts with CD21 (CR2, C3d fragment receptor) and CD81 through two extracellular C2-type Ig-like domains, forming together with CD225 the BCR complex. The intracellular domain of CD19 is involved in intracellular signaling cascades, primarily but not exclusively regulating signals downstream of the BCR and CD22 (Mei et al. (2012) "*Rationale of Anti-CD19 Immunotherapy: An Option To Target Autoreactive Plasma Cells In Autoimmunity*," Arthritis Res and Ther. 14(Suppl. 5):S1; Wang et al. (2012) "*CD19: A Biomarker For B Cell Development, Lymphoma Diagnosis And Therapy*," Exp. Hematol. and Oncol. 1:36); Del Nagro et al. (2005) "*CD19 Function in Central and Peripheral B-Cell Development*," Immunologic Res. 31:119-131).

Several properties of CD19 suggest its possible potential as a target for immunotherapy. CD19 is one of the most ubiquitously expressed antigens in the B cell lineage and is expressed on >95% of B cell malignancies, including acute lymphoblastic leukemia (ALL), chronic lymphocytic leukemia (CLL), and non-Hodgkin's Lymphoma (NHL) (Wilson, K. et al. (2010) "*Flow Minimal Residual Disease Monitoring Of Candidate Leukemic Stem Cells Defined By The Immunophenotype, CD34+CD38lowCD9+ In B-Lineage Childhood Acute Lymphoblastic Leukemia*," Haematologica 95(4):679-683; Maloney, D. G. et al. (1997) "*IDEC-C2B8 (Rituximab) Anti-CD20 Monoclonal Antibody Therapy In Patients With Relapsed Low-Grade Non-Hodgkin's Lymphoma*," Blood 90(6):2188-2195; Vose, J. M. (1998) "*Current Approaches To The Management Of Non-Hodgkin's Lymphoma*," Semin. Oncol. 25(4):483-491; Nagorsen, D. et al. (2012) "*Blinatumomab: A Historical Perspective*," Pharmacol. Ther. 136(3):334-342; Topp, M. S. et al. (2011) "*Targeted Therapy With The T-Cell-Engaging Antibody Blinatumomab Of Chemotherapy-Refractory Minimal Residual Disease In B-Lineage Acute Lymphoblastic Leukemia Patients Results In High Response Rate And Prolonged Leukemia-Free Survival*," J. Clin Oncol. 2011 Jun. 20; 29(18):2493-2498; Nadler, et al. (1983) "*B4, A Human B Lymphocyte-Associated Antigen Expressed On Normal, Mitogen-Activated, And Malignant B Lymphocytes.*" J. Immunol.; 131:244-250; Ginaldi et al. (1998) "*Levels Of Expression Of CD19 And CD20 In Chronic B Cell Leukaemias*," J. Clin. Pathol. 51:364-369; Anderson et al. (1984) "*Expression of Human B Cell-Associated Antigens on Leukemias and Lymphomas: A Model of Human B Cell Differentiation*," Blood 63:1424-1433). CD19 is expressed on few if any other cell types and is also not expressed on terminally differentiated plasma cells, which thus may be spared by CD19-directed therapies. CD19 is not shed into the circulation, and can rapidly internalize (Ma et al. (2002) "*Radioimmunotherapy For Model B Cell Malignancies Using 90Y-Labeled Anti-CD19 And Anti-CD20 Monoclonal Antibodies*," Leukemia 16:60-66; Raufi et al. (2013) "*Targeting CD19 in B-cell lymphoma: emerging role of SAR3419," Cancer Management Res 3:225-233).

Notably, CD19 expression is maintained on B cell lymphomas that become resistant to anti-CD20 therapy (Davis et al. (1999) "*Therapy of B-cell Lymphoma With Anti-CD20 Antibodies Can Result In The Loss Of CD20 Antigen Expression.*" Clin Cancer Res, 5:611-615, 1999). CD19 has also been suggested as a target to treat autoimmune diseases (Tedder (2009) "*CD19: A Promising B Cell Target For Rheumatoid Arthritis,*" Nat. Rev. Rheumatol. 5:572-577).

B cell malignancies represent a heterogeneous group of disorders with widely varying characteristics and clinical behavior. Historically, most patients with symptomatic disease received a combination of non-cross-reactive genotoxic agents with the intent of achieving a durable remission and, in some cases, a cure. Although effective, many traditional regimens are also associated with considerable acute and long-term toxicities (see, e.g., Stock, W. et al. (2013) "*Dose Intensification Of Daunorubicin And Cytarabine During Treatment Of Adult Acute Lymphoblastic Leukemia: Results Of Cancer And Leukemia Group B Study 19802,*" Cancer. 2013 Jan. 1; 119(1):90-98). The anti-CD20 monoclonal antibody rituximab is used for the treatment of many B cell disorders, where it may be employed in combination with "standard of care" agents or employed as a single agent (Fowler et al. (2013) "*Developing Novel Strategies to Target B-Cell Malignancies,*" Targeted Pathways, B-Cell Lymphoma in ASCO Educational Book, pp. 366-372; Bargou, R. et al. (2008) "*Tumor Regression In Cancer Patients By Very Low Doses Of A T Cell-Engaging Antibody,*" Science 321 (5891):974-977; Thomas, D. A. et al. (2010) "*Chemoimmunotherapy With A Modified Hyper-CVAD And Rituximab Regimen Improves Outcome In De Novo Philadelphia Chromosome-Negative Precursor B-Lineage Acute Lymphoblastic Leukemia,*" J. Clin. Oncol. 28(24):3880-3889). Despite encouraging clinical results, retreatment of patients with indolent lymphomas with single agent rituximab has been associated with a response rate of only 40%, suggesting that resistance may occur in malignant B cells as a response to prolonged exposure to rituximab (Smith (2003) "*Rituximab (Monoclonal Anti-CD20 Antibody): Mechanisms Of Action And Resistance.*" Oncogene. 22:7359-68; Davis et al. (1999) "*Therapy of B-cell Lymphoma With Anti-CD20 Antibodies Can Result In The Loss Of CD20 Antigen Expression,*" Clin Cancer Res, 5:611-615, 1999; Gabrilovich, D. et al. (2003) "*Tumor Escape From Immune Response: Mechanisms And Targets Of Activity,*" Curr. Drug Targets 4(7):525-536). Rituximab-resistant cell lines generated in vitro have been reported to display cross-resistance against multiple chemotherapeutic agents (Czuczman et al. (2008) "*Acquirement Of Rituximab Resistance In Lymphoma Cell Lines Is Associated With Both Global CD20 Gene And Protein Down-Regulation Regulated At The Pretranscriptional And Post-transcriptional Levels,*" Clin Cancer Res. 14:1561-1570; Olejniczak et al. (2008) "*Acquired Resistance To Rituximab Is Associated With Chemotherapy Resistance Resulting From Decreased Bax And Bak Expression,*" Clin Cancer Res. 14:1550-1560).

Additional B cell lymphoma surface antigens targeted by therapeutic antibodies include CD19 (Hoelzer (2013) "*Targeted Therapy With Monoclonal Antibodies In Acute Lymphoblasitic Leukemia,* Curr. Opin. Oncol. 25:701-706; Hammer (2012) "*CD19 As An Attractive Target For Antibody-Based Therapy,*" mAbs 4:571-577). However, despite the potent anti-lymphoma activities associated with complex internalization and intracellular release of free drug were reported for various anti-CD19 antibodies bi-specific antibodies having an anti-CD19 binding portion or antibody drug conjugates (ADCs) the anti-tumor effects of these anti-CD19 antibodies or ADCs were variable, suggesting that antibody specific properties, such as epitope binding, the ability to induce CD19 oligomerization or differences in intracellular signaling affect their potencies (Du et al. (2008) "*Differential Cellular Internalization Of Anti-CD19 And-CD22 Immunotoxins Results In Different Cytotoxic Activity,*" Cancer Res. 68:6300-6305; Press et al., (1994) "*Retention Of B-Cell-Specific Monoclonal Antibodies By Human Lymphoma Cells. Blood,*" 83:1390-1397; Szatrowski et al. (2003) "*Lineage Specific Treatment Of Adult Patients With Acute Lymphoblastic Leukemia In First Remission With Anti-B4-Blocked Ricin Or High-Dose Cytarabine: Cancer And Leukemia Group B Study 9311,*" Cancer 97:1471-1480; Frankel et al. (2013) "*Targeting T Cells To Tumor Cells Using Bispecific Antibodies,*" Curr. Opin. Chem. Biol. 17:385-392).

Thus, despite improvements in survival for many, the majority of patients suffering from B cell malignancies continue to relapse following standard chemoimmunotherapy and more than 15,000 patients still die annually in the United States from B cell cancers. Accordingly, treatments with new non-cross-resistant compounds are needed to further improve patient survival.

B. CD3

CD3 is a T cell co-receptor composed of four distinct chains (Wucherpfennig, K. W. et al. (2010) "*Structural Biology Of The T-Cell Receptor: Insights Into Receptor Assembly, Ligand Recognition, And Initiation Of Signaling,*" Cold Spring Harb. Perspect. Biol. 2(4):a005140; pages 1-14; Chetty, R. et al. (1994) "*CD3: Structure, Function, And Role Of Immunostaining In Clinical Practice,*" J. Pathol. 173(4): 303-307; Guy, C. S. et al. (2009) "*Organization Of Proximal Signal Initiation At The TCR:CD3 Complex,*" Immunol. Rev. 232(1):7-21).

In mammals, the complex contains a CD3γ chain, a CD3δ chain, and two CD3ε chains. These chains associate with a molecule known as the T cell receptor (TCR) in order to generate an activation signal in T lymphocytes (Smith-Garvin, J. E. et al. (2009) "*T Cell Activation,*" Annu. Rev. Immunol. 27:591-619). In the absence of CD3, TCRs do not assemble properly and are degraded (Thomas, S. et al. (2010) "*Molecular Immunology Lessons From Therapeutic T-Cell Receptor Gene Transfer,*" Immunology 129(2):170-177). CD3 is found bound to the membranes of all mature T cells, and in virtually no other cell type (see, Janeway, C. A. et al. (2005) In: IMMUNOBIOLOGY: THE IMMUNE SYSTEM IN HEALTH AND DISEASE," 6th ed. Garland Science Publishing, NY, pp. 214-216; Sun, Z. J. et al. (2001) "*Mechanisms Contributing To T Cell Receptor Signaling And Assembly Revealed By The Solution Structure Of An Ectodomain Fragment Of The CD3ε:γ Heterodimer,*" Cell 105(7):913-923; Kuhns, M. S. et al. (2006) "*Deconstructing The Form And Function Of The TCR/CD3 Complex,*" Immunity. 2006 February; 24(2):133-139).

The invariant CD3ε signaling component of the T cell receptor (TCR) complex on T cells, has been used as a target to force the formation of an immunological synapse between T cells and tumor cells. Co-engagement of CD3 and the tumor antigen activates the T cells, triggering lysis of tumor cells expressing the tumor antigen (Baeuerle et al. (2011) "Bispecific T Cell Engager For Cancer Therapy," In: BISPECIFIC ANTIBODIES, Kontermann, R. E. (Ed.) Springer-Verlag; 2011:273-287). This approach allows bi-specific antibodies to interact globally with the T cell compartment with high specificity for tumor cells and is widely applicable to a broad array of cell-surface tumor antigens.

C. Antibodies and Other Binding Molecules

Antibodies are immunoglobulin molecules capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity.

The ability of an intact, unmodified antibody (e.g., an IgG) to bind an epitope of an antigen depends upon the presence of Variable Domains on the immunoglobulin light and heavy chains (i.e., the VL and VH Domains, respectively). Interaction of an antibody light chain and an antibody heavy chain and, in particular, interaction of its VL and VH Domains forms one of the epitope binding sites of the antibody. In contrast, the scFv construct comprises a VL and VH Domain of an antibody contained in a single polypeptide chain wherein the Domains are separated by a flexible linker of sufficient length to allow self-assembly of the two Domains into a functional epitope binding site. Where self-assembly of the VL and VH Domains is rendered impossible due to a linker of insufficient length (less than about 12 amino acid residues), two of the scFv constructs interact with one another other to form a bivalent molecule in which the VL of one chain associates with the VH of the other (reviewed in Marvin et al. (2005) "*Recombinant Approaches To IgG-Like Bispecific Antibodies*," Acta Pharmacol. Sin. 26:649-658).

In addition to their known uses in diagnostics, antibodies have been shown to be useful as therapeutic agents. The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Nearly 200 antibody-based drugs have been approved for use or are under development.

Natural antibodies are capable of binding to only one epitope species (i.e., mono-specific), although they can bind multiple copies of that species (i.e., exhibiting bi-valency or multi-valency). A wide variety of recombinant bi-specific antibody formats have been developed (see, e.g., PCT Publication Nos. WO 2008/003116, WO 2009/132876, WO 2008/003103, WO 2007/146968), most of which use linker peptides either to fuse the antibody core (IgA, IgD, IgE, IgG or IgM) to a further binding protein (e.g. scFv) or to fuse e.g. two Fab fragments or scFv. Typically, such approaches involve compromises and trade-offs. For example, PCT Publications Nos. WO 2013/174873, WO 2011/133886 and WO 2010/136172 disclose that the use of linkers may cause problems in therapeutic settings, and teaches a tri-specific antibody in which the CL and CH1 Domains are switched from their respective natural positions and the VL and VH Domains have been diversified (WO 2008/027236; WO 2010/108127) to allow them to bind to more than one antigen. Thus, the molecules disclosed in these documents trade binding specificity for the ability to bind additional antigen species. PCT Publications Nos. WO 2013/163427 and WO 2013/119903 disclose modifying the CH2 Domain to contain a fusion protein adduct comprising a binding domain. The document notes that the CH2 Domain likely plays only a minimal role in mediating effector function. PCT Publications Nos. WO 2010/028797, WO2010028796 and WO 2010/028795 disclose recombinant antibodies whose Fc Regions have been replaced with additional VL and VH Domains, so as to form tri-valent binding molecules. PCT Publications Nos. WO 2003/025018 and WO2003012069 disclose recombinant diabodies whose individual chains contain scFv domains. PCT Publications No. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publications Nos. WO 2014/022540, WO 2013/003652, WO 2012/162583, WO 2012/156430, WO 2011/086091, WO 2007/075270, WO 1998/002463, WO 1992/022583 and WO 1991/003493 disclose adding additional Binding Domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another). Thus, the molecules disclosed in these documents trade native antibody structure for the ability to bind additional antigen species.

The art has additionally noted the capability to produce diabodies that differ from such natural antibodies in being capable of binding two or more different epitope species (i.e., exhibiting bi-specificity or multispecificity in addition to bi-valency or multi-valency) (see, e.g., Holliger et al. (1993) "'*Diabodies*': *Small Bivalent And Bispecific Antibody Fragments*," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672; WO 02/02781 (Mertens et al.); Olafsen, T. et al. (2004) "*Covalent Disulfide-Linked Anti-CEA Diabody Allows Site-Specific Conjugation And Radiolabeling For Tumor Targeting Applications*," Protein Eng Des Sel. 17(1):21-27; Wu, A. et al. (2001) "*Multimerization Of A Chimeric Anti-CD20 Single Chain Fv-Fv Fusion Protein Is Mediated Through Variable Domain Exchange*," Protein Engineering 14(2):1025-1033; Asano et al. (2004) "*A Diabody For Cancer Immunotherapy And Its Functional Enhancement By Fusion Of Human Fc Domain*," Abstract 3P-683, J. Biochem. 76(8):992; Takemura, S. et al. (2000) "*Construction Of A Diabody (Small Recombinant Bispecific Antibody) Using A Refolding System*," Protein Eng. 13(8):583-588; Baeuerle, P. A. et al. (2009) "*Bispecific T-Cell Engaging Antibodies For Cancer Therapy*," Cancer Res. 69(12):4941-4944).

The design of a diabody is based on the single chain variable region fragments (scFv). Such molecules are made by linking light and/or heavy chain variable regions by using a short linking peptide. Bird et al. (1988) ("*Single-Chain Antigen-Binding Proteins*," Science 242:423-426) describes example of linking peptides which bridge approximately 3.5 nm between the carboxy terminus of one variable region and the amino terminus of the other variable region. Linkers of other sequences have been designed and used (Bird et al. (1988) "*Single-Chain Antigen-Binding Proteins*," Science 242:423-426). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

U.S. Pat. No. 7,585,952 and United States Patent Publication No. 2010-0173978 concern scFv molecules that are immunospecific for ErbB2. Bi-specific T cell engagers ("BiTEs"), a type of scFv molecule has been described (WO 05/061547; Baeuerle, P et al. (2008) "*BiTE: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977). Such molecules are composed of a single polypeptide chain molecule having two antigen-binding domains, one of which immunospecifically binds to a CD3 epitope and the second of which immunospecifically binds to an antigen present on the surface of a target cell.

Bi-specific molecules that target both CD19 and CD3 have been described. Blinatumomab, a bi-specific scFv-CD19×CD3 BiTE is in clinical trials and is reported to have an affinity for CD3 of ~100 nM, and an affinity for CD19 of ~1 nM. Blinatumomab exhibits an $EC_{50}$ for target cell lysis in vitro of ~10-100 pg/ml (Frankel et al. (2013) "*Targeting T Cells To Tumor Cells Using Bispecific Antibodies*," Curr. Opin. Chem. Biol. 17:385-392). A bi-specific CD19×CD3 dual affinity retargeting (DART) has also been developed (Moore et al. (2011) "*Application Of Dual Affinity Retargeting Molecules To Achieve Optimal Redirected T-Cell Killing Of B-Cell Lymphoma*," Blood 117(17):4542-4551). Compared with the bi-specific scFv-CD19×CD3 BiTE, this molecule exhibited similar binding affinities but had a lower $EC_{50}$ for target cell lysis in vitro of ~0.5 to 5 pg/ml and showed consistently higher levels of maximum lysis AFM11, a CD19×CD3 a bi-specific Tandab has also been described. AFM11 is reported to have an $EC_{50}$ for target cell lysis in vitro of ~0.5 to 5 pg/ml (Zhukovsky et al. (2013) "*A CD19/CD3 Bispecific Tandab, AFM11, Recruits T Cells To Potently and Safely Kill CD19+ Tumor Cells*," J Clin Oncol 31, 2013 (suppl; abstr 3068)). None of these constructs include an Fc domain.

Notwithstanding such success, the production of stable, functional heterodimeric, non-mono-specific diabodies can be further optimized by the careful consideration and placement of cysteine residues in one or more of the employed polypeptide chains. Such optimized diabodies can be produced in higher yield and with greater activity than non-optimized diabodies. The present invention is thus directed to the problem of providing polypeptides that are particularly designed and optimized to form heterodimeric diabodies. The invention solves this problem through the provision of exemplary, optimized CD19×CD3 diabodies.

SUMMARY OF THE INVENTION

The present invention is directed to bi-specific monovalent diabodies that comprise two polypeptide chains and which possess one binding site specific for an epitope of CD19 and one binding site specific for an epitope of CD3 (i.e., a "CD19×CD3 bi-specific monovalent diabody"). Most preferably, such CD19×CD3 bi-specific monovalent diabodies are composed of three polypeptide chains and possess one binding site specific for an epitope of CD19 and one binding site specific for an epitope of CD3 and additionally comprise an immunoglobulin Fc Domain (i.e., a "CD19× CD3 bi-specific monovalent Fc diabody"). The bi-specific monovalent diabodies and bi-specific monovalent Fc diabodies of the present invention are capable of simultaneous binding to CD19 and CD3. The invention is directed to pharmaceutical compositions that contain such bi-specific monovalent diabodies or such bi-specific monovalent Fc diabodies. The invention is additionally directed to methods for the use of such diabodies in the treatment of disease, in particular hematologic malignancies.

The CD19×CD3 bi-specific monovalent diabodies and bi-specific monovalent Fc diabodies of the invention thus comprise at least two different polypeptide chains. The polypeptide chains of such diabodies associate with one another in a heterodimeric manner to form one binding site specific for an epitope of CD19 and one binding site specific for an epitope of CD3. A CD19×CD3 bi-specific monovalent diabody or bi-specific monovalent Fc diabody of the present invention is thus monovalent in that it is capable of binding to only one copy of an epitope of CD19 and to only one copy of an epitope of CD3, but bi-specific in that a single diabody is able to bind simultaneously to the epitope of CD19 and to the epitope of CD3. Each of the polypeptide chains of the diabodies is covalently bonded to another polypeptide chain of the diabody, for example by disulfide bonding of cysteine residues located within such polypeptide chains, so as to form a covalently bonded complex. In particular embodiments, the diabodies of the present invention further have an immunoglobulin Fc Domain and/or an Albumin-Binding Domain to extend half-life in vivo.

In detail, the invention provides a CD19×CD3 bi-specific monovalent Fc diabody capable of specific binding to CD19 and to CD3, wherein the diabody comprises a first, a second and a third polypeptide chain, wherein the polypeptide chains form a covalently bonded complex, and wherein:

I. the first polypeptide chain comprises, in the N-terminal to C-terminal direction:
  A. a Domain IA, comprising
    (1) a sub-Domain (IA1), which comprises a VL Domain capable of binding to either CD19 ($VL_{CD19}$) or CD3 ($VL_{CD3}$); and
    (2) a sub-Domain (IA2), which comprises a VH Domain capable of binding to either CD19 ($VH_{CD19}$) or CD3 ($VH_{CD3}$);
    wherein the sub-Domains IA1 and IA2 are separated from one another by a polypeptide linker, and are either
      (a) $VL_{CD19}$ and $VH_{CD3}$; or
      (b) $VL_{CD3}$ and $VH_{CD19}$;
  B. a Domain IB, comprising a charged Heterodimer-Promoting Domain, wherein the Domain IB is separated from the Domain 1A by a polypeptide linker;
  C. a Domain IC, comprising a CH2-CH3 Domain of an antibody; and
II. the second polypeptide chain comprises, in the N-terminal to C-terminal direction:
  A. a Domain IIA, comprising
    (1) a sub-Domain (IIA1), which comprises a VL Domain capable of binding to either CD19 ($VL_{CD19}$) or CD3 ($VL_{CD3}$); and
    (2) a sub-Domain (IIA2), which comprises a VH Domain capable of binding to either CD19 ($VH_{CD19}$) or CD3 ($VH_{CD3}$);

wherein the sub-Domains IIA1 and IIA2 are separated from one another by a polypeptide linker, and are:
(a) $VL_{CD19}$ and $VH_{CD3}$, if the sub-Domains IA1 and IA2 are $VL_{CD3}$ and $VH_{CD19}$; or
(b) $VL_{CD3}$ and $VH_{CD19}$, if the sub-Domains IA1 and IA2 are $VL_{CD19}$ and $VH_{CD3}$;

B. a Domain IIB, comprising a charged Heterodimer-Promoting Domain, wherein the Domain IIB is separated from the Domain IIA by a polypeptide linker, and wherein the charged Heterodimer-Promoting Domain of the Domain IB and the charged Heterodimer-Promoting Domain of the Domain IIB have opposite charges; and III. the third polypeptide chain comprises, in the N-terminal to C-terminal direction a Domain IIIC that comprises a CH2-CH3 Domain of an antibody;

wherein the $VL_{CD19}$ and the $VH_{CD19}$ domains form a CD19 binding domain, and the $VL_{CD3}$ and $VH_{CD3}$ domains form a CD3 binding domain; and the CH2-CH3 Domains of the first and third polypeptide chains form an Fc domain capable of binding to an Fc receptor, thereby forming the CD19×CD3 bi-specific monovalent diabody.

The invention additionally provides the embodiment of the above-indicated CD19×CD3 bi-specific monovalent Fc diabody, wherein:
(A) the Domains IB and IIB each comprise a cysteine residue that covalently bonds the first polypeptide chain to the second polypeptide chain via a disulfide bond; and
(B) the Domains IC and IIIC each comprise a cysteine residue that covalently bonds the first polypeptide chain to the third polypeptide chain via a disulfide bond.

The invention additionally provides the embodiment of any of the above-indicated CD19×CD3 bi-specific monovalent Fc diabodies, wherein the $VL_{CD19}$ has the amino acid sequence of SEQ ID NO:17 and the $VH_{CD19}$ has the amino acid sequence of SEQ ID NO:21.

The invention additionally provides the embodiment of any of the above-indicated CD19×CD3 bi-specific monovalent Fc diabodies, wherein the $VL_{CD3}$ has the amino acid sequence of SEQ ID NO:25 and the $VH_{CD3}$ has the amino acid sequence of SEQ ID NO:29.

The invention additionally provides the embodiment of any of the above-indicated CD19×CD3 bi-specific monovalent Fc diabodies, wherein the CH2-CH3 Domain of the Domain IC has the amino acid sequence of SEQ ID NO:15 and the CH2-CH3 Domain of the Domain IIIC has the amino acid sequence of SEQ ID NO:16.

The invention additionally provides the embodiment of any of the above-indicated CD19×CD3 bi-specific monovalent Fc diabodies, wherein
(A) the charged Heterodimer-Promoting Domain of the Domain IB has the amino acid sequence of SEQ ID NO:10 and the charged Heterodimer-Promoting Domain of the Domain IIB has the amino acid sequence of SEQ ID NO:11; or
(B) the charged Heterodimer-Promoting Domain of the Domain IB has the amino acid sequence of SEQ ID NO:12 and the charged Heterodimer-Promoting Domain of the Domain IIB has the amino acid sequence of SEQ ID NO:13.

The invention additionally provides the embodiment of any of the above-indicated CD19×CD3 bi-specific monovalent Fc diabodies, wherein:
(A) the first polypeptide chain has the amino acid sequence of SEQ ID NO:35;
(B) the second polypeptide chain has the amino acid sequence of SEQ ID NO:37; and
(C) the third polypeptide chain has the amino acid sequence of SEQ ID NO:39.

The invention additionally provides the embodiment of any of the above-indicated CD19×CD3 bi-specific monovalent Fc diabodies, which is capable of cross-reacting with both human and primate CD19 and CD3.

The invention additionally provides any of the above-described CD19×CD3 bi-specific monovalent Fc diabodies for use as a pharmaceutical.

The invention additionally provides any of the above-described CD19×CD3 bi-specific monovalent Fc diabodies for use in the treatment of a disease or condition associated with or characterized by the expression of CD19, or in a method of treating a disease or condition characterized by the expression of CD19, particularly wherein the disease or condition associated with or characterized by the expression of CD19 is cancer, and more particularly, wherein the cancer is selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

The invention additionally provides a covalently associated polypeptide complex, wherein the polypeptide complex comprises a first polypeptide chain and a second polypeptide chain, wherein:
(A) the first polypeptide chain comprises a polypeptide having the amino acid sequence of SEQ ID NO:2 linked to a Heterodimer-Promoting Domain having the amino acid sequence of SEQ ID NO:12; and
(B) the second polypeptide chain comprises a polypeptide having the amino acid sequence of SEQ ID NO:2 linked to a Heterodimer-Promoting Domain having the amino acid sequence of SEQ ID NO:13;
wherein the Heterodimer-Promoting Domains of the first polypeptide chain and the Heterodimer-Promoting Domains of the second polypeptide chain are covalently bonded to one another via a disulfide bond.

The invention additionally provides a pharmaceutical composition comprising any of the above-described CD19×CD3 bi-specific monovalent Fc diabodies and a physiologically acceptable carrier. The invention additionally concerns the use of such a pharmaceutical composition in the treatment of a disease or condition associated with or characterized by the expression of CD19, particularly wherein the disease or condition associated with or characterized by the expression of CD19 is cancer, and more particularly, wherein the cancer is selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

The CD19×CD3 bi-specific monovalent diabodies and CD19×CD3 bi-specific monovalent Fc diabodies of the present invention are preferably capable of exhibiting similar binding affinity to soluble human and cynomolgus monkey CD3 and a 10-fold difference in binding to CD19, as analyzed by BIACORE® (surface plasmon resonance (SPR) technology for analyzing and characterizing molecular interactions in terms of binding and kinetics), or as analyzed by flow cytometry using a CD4+ and CD8+ gated T cell population and a CD20+ gated B cell population.

The CD19×CD3 bi-specific monovalent diabodies and CD19×CD3 bi-specific monovalent Fc diabodies of the present invention are preferably capable of mediating redirected killing of target tumor cells using human T cells in an assay employing any of 3 target B lymphoma cell lines, Raji/GF (Burkitt's lymphoma), HBL-2 (mantle cell lymphoma), or Jeko-1 (mantle cell lymphoma), and using purified human primary T cells as effector cells. In such an assay, target tumor cell killing is measured using a lactate dehydrogenase (LDH) release assay in which the enzymatic activity of LDH released from cells upon cell death is quantitatively measured, or by a luciferase assay in which luciferase relative light unit (RLU) is the read-out to indicate relative viability of Raji/GF target cells, which have been engineered to express both the green fluorescent protein (GFP) and luciferase reporter genes. The observed EC50 of such redirected killing is about 5 pM or less, about 3 pM or less, about 1 pM or less, about 0.5 pM or less, about 0.3 pM or less, about 0.2 pM or less, about 0.1 pM or less, about 0.05 pM or less, about 0.04 pM or less, about 0.03 pM or less, about 0.02 pM or less or about 0.01 pM or less.

The CD19×CD3 bi-specific monovalent diabodies and CD19×CD3 bi-specific monovalent Fc diabodies of the present invention are preferably capable of mediating cytoxicity in human and cynomolgus monkey peripheral blood mononuclear cells (PBMCs) so as to cause a dose-dependent CD20+ B cell depletion in both such cell systems at an Effector cell to T cell ratio of 2:1, 3:1, 4:1, 5:1, 6:1, 7:1, 8:1 or 9:1. The observed EC50 of human CD20+ B cell depletion is about 7 pM or less, about 5 pM or less, about 3 pM or less, about 1 pM or less, about 0.5 pM or less, about 0.3 pM or less, about 0.2 pM or less, about 0.1 pM or less, about 0.05 pM or less, about 0.04 pM or less, about 0.03 pM or less, about 0.02 pM or less or about 0.01 pM or less. The observed EC50 of cynomolgus CD20+ B cell depletion is about 1000 pM or less, about 900 pM or less, about 800 pM or less, about 500 pM or less, about 300 pM or less, about 100 pM or less, about 50 pM or less, about 20 pM or less, about 10 pM or less, about 5 pM or less, about 2 pM or less, or about 1 pM or less, such that the ratio of autologous human B cell depletion to cynomolgus monkey B cell depletion is about 500:1 or less, about 300:1 or less, about 100:1 or less, about 50:1 or less, about 20:1 or less or about 10:1 or less.

The CD19×CD3 bi-specific monovalent diabodies and CD19×CD3 bi-specific monovalent Fc diabodies of the present invention are preferably capable of mediating the release of cytokines (e.g., IFN-γ, TNF-α, IL-2, IL-4, IL-6, and IL-10 and especially IFN-γ and TNF-α) by human and cynomolgus monkey PBMCs. Such release is about 5000 pg/mL or less, about 4000 pg/mL or less, about 3000 pg/mL or less, about 2000 pg/mL or less, about 1000 pg/mL or less, about 500 pg/mL or less, about 2000 pg/mL or less, or about 100 pg/mL or less. The mean EC50 of such cytokine release from human PBMCs is about 100 pM or less, about 90 pM or less, about 80 pM or less, about 50 pM or less, about 30 pM or less, about 20 pM or less, about 10 pM or less, or about 5 pM or less. The mean EC50 of such cytokine release from cynomolgus monkey PBMCs is about 3000 pM or less, about 2000 pM or less, about 1000 pM or less, about 500 pM or less, about 300 pM or less, about 200 pM or less, about 100 pM or less, or about 50 pM or less.

The CD19×CD3 bi-specific monovalent diabodies and CD19×CD3 bi-specific monovalent Fc diabodies of the present invention are preferably capable of mediating the inhibition of human B cell lymphoma tumor growth in a co-mix xenograft in which such molecules are introduced into NOD/SCID mice along with HBL-2 (a human mantle cell lymphoma) or Raji (Burkitt's lymphoma) tumor cells and activated human T cells at a ratio of 1:5. Preferably, such diabodies are capable of inhibiting tumor growth when provided at a concentration of greater than 100 µg/ml, at a concentration of about 100 µg/kg, at a concentration of about 80 µg/kg, at a concentration of about 50 µg/kg, at a concentration of about 20 µg/kg, at a concentration of about 10 µg/kg, at a concentration of about 5 µg/kg, at a concentration of about 2 µg/kg, at a concentration of about 1 µg/kg, at a concentration of about 0.5 µg/kg, at a concentration about 0.2 µg/kg, at a concentration of about 0.1 µg/kg, at a concentration of about 0.05 µg/kg, at a concentration of about 0.02 µg/kg, at a concentration of about 0.01 µg/kg, or at a concentration of about 0.005 µg/kg, or at a concentration less than 0.005 µg/kg.

The CD19×CD3 bi-specific monovalent diabodies and CD19×CD3 bi-specific monovalent Fc diabodies of the present invention are preferably capable of exhibiting anti-tumor activity in an HBL-2 (human mantle cell lymphoma) xenograft model in female NSG B2m−/− mice, implanted with HBL-2 tumor cells intradermally (ID) on Day 0 followed by intraperitoneal (IP) injection of PBMCs on Day 4 and administration of diabody on Day 17, so as to cause a decrease in tumor volume of about 10%, about 20%, about 40%, about 60%, about 80%, about 90% or more than 90%.

The CD19×CD3 bi-specific monovalent diabodies and CD19×CD3 bi-specific monovalent Fc diabodies of the present invention are preferably capable of exhibiting prolonged half-lives upon introduction into a recipient human or non-human animal. Such half-lives can be measured by introducing the diabody into a human FcRn transgenic mouse (U.S. Pat. Nos. 6,992,234 and 7,358,416; Haraya, K. (2014) "*Application Of Human FcRn Transgenic Mice As A Pharmacokinetic Screening Tool Of Monoclonal Antibody,*" Xenobiotica 2014 Jul. 17:1-8; Proetzel, G. et al. (2014) "*Humanized FcRn mouse models for evaluating pharmacokinetics of human IgG antibodies,*" Methods 65(1):148-153; Stein, C. et al. (2012) "*Clinical Chemistry Of Human FcRn Transgenic Mice,*" Mamm. Genome 23(3-4):259-269; Roopenian, D. C. et al. (2010) "*Human FcRn Transgenic Mice For Pharmacokinetic Evaluation Of Therapeutic Antibodies,*" Methods Molec. Biol. 602:93-104). The measurement is conducted using a B6.Cg-Fcgrt$^{tm1Dcr}$ (CAG-FCGRT)276Dcr/DcrJ mouse (Stock Number 004919), available from the Jackson Laboratories, Bar Harbor, Me., US.

For the avoidance of any doubt, the diabodies of the invention may exhibit one, two, three, more than three or all of the functional attributes described herein. Thus the diabodies of the invention may exhibit any combination of the functional attributes described herein.

The diabodies of the present invention may be for use as a pharmaceutical. Preferably, the diabodies are for use in the treatment of a disease or condition associated with or characterized by the expression of CD19. The invention also relates to the use of diabodies of the invention in the manufacture of a pharmaceutical composition, preferably for the treatment of a disease or condition associated with or characterized by the expression of CD19 as further defined herein.

The disease or condition associated with or characterized by the expression of CD19 may be a B cell malignancy (Campo, E. et al. (2011) "*The* 2008 *WHO Classification Of Lymphoid Neoplasms And Beyond: Evolving Concepts And Practical Applications*," Blood 117(19):5019-5032). For example, the cancer may be selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma.

The invention additionally provides a pharmaceutical composition comprising any of the above-described diabodies and a physiologically acceptable carrier.

The invention particularly pertains to such a pharmaceutical composition wherein the treated disease or condition is refractory to treatment with rituximab.

The invention additionally provides a use of the above-described pharmaceutical composition in the treatment of a disease or condition associated with or characterized by the expression of CD19.

The invention is particularly directed to the embodiment of such use, wherein the disease or condition associated with or characterized by the expression of CD19 is a B cell malignancy (especially a cancer selected from the group consisting of: acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma).

Terms such as "about" should be taken to mean within 10%, more preferably within 5%, of the specified value, unless the context requires otherwise.

BRIEF DESCRIPTION OF THE DRAWINGS

FIG. 6E shows the killing of Raji/GF cells as determined using a luciferase assay (RLU) to measure relative viable cells. EC50 values for DART-A are shown on each graph for 1 representative experiment. DART-A: ▲; Control DART 1: ▼.

FIGS. 9A-9B show CD19×CD3 bi-specific molecule (DART-A)-mediated autologous B cell depletion in human or cynomolgus monkey PBMCs. Dose-response curves are presented for DART (DART-A or Control DART 1)-mediated autologous B cell depletion. FIG. 9A: percent of human CD20+ cells after PBMC treatment with various doses of DART-A or Control DART 1. FIG. 9B: percent of cynomolgus monkey CD20+ cells after PBMC treatment with various doses of DART-A or Control DART 1. EC50 values for DART-A are shown on each graph. The percent of CD3+ cells was analyzed in parallel and used as an internal reference control—no changes were observed at any concentration tested. DART-A: ▲; Control DART 1: ▼.

FIG. 10 show CD19×CD3 bi-specific molecule (DART-A)-mediated redirected killing of target cells with cynomolgus monkey PBMCs at E:T=30:1. DART-A: ▲; Control DART 1: ▼.

FIG. 11A: γ-interferon (IFNγ) release; FIG. 11B: tumor necrosis factor-α (TNF-α) release; FIG. 11C: Interleukin 2 (IL-2) release. DART-A: ▲; Control DART 1: ▼.

FIG. 19A: Female NSG B2m−/− mice (n=8 per group) were implanted intradermally (ID) with HBL-2 tumor cells ($5\times10^6$) on Day 0. On Day 4, mice were implanted with PBMCs ($5\times10^7$) intraperitoneally (IP). The mice were then treated intravenously (IV) with vehicle, Control DART 1, or the CD19×CD3 bi-specific DART-A as indicated (see Rx arrows). Tumor volume is shown as a group mean±SEM. FIG. 19B: Female NSG B2m−/− mice (n=8 per group) were implanted intradermally (ID) with HBL-2 tumor cells ($5\times10^6$) on Day 0. On Day 4, mice were implanted with PBMCs ($5\times10^7$) intraperitoneally (IP). The mice were then treated intravenously (IV) with vehicle, Control DART 1 or the CD19×CD3 bi-specific DART-A as indicated (see Rx arrows). Tumor volume is shown as a group mean±SEM.

DETAILED DESCRIPTION OF THE INVENTION

Figure 1:
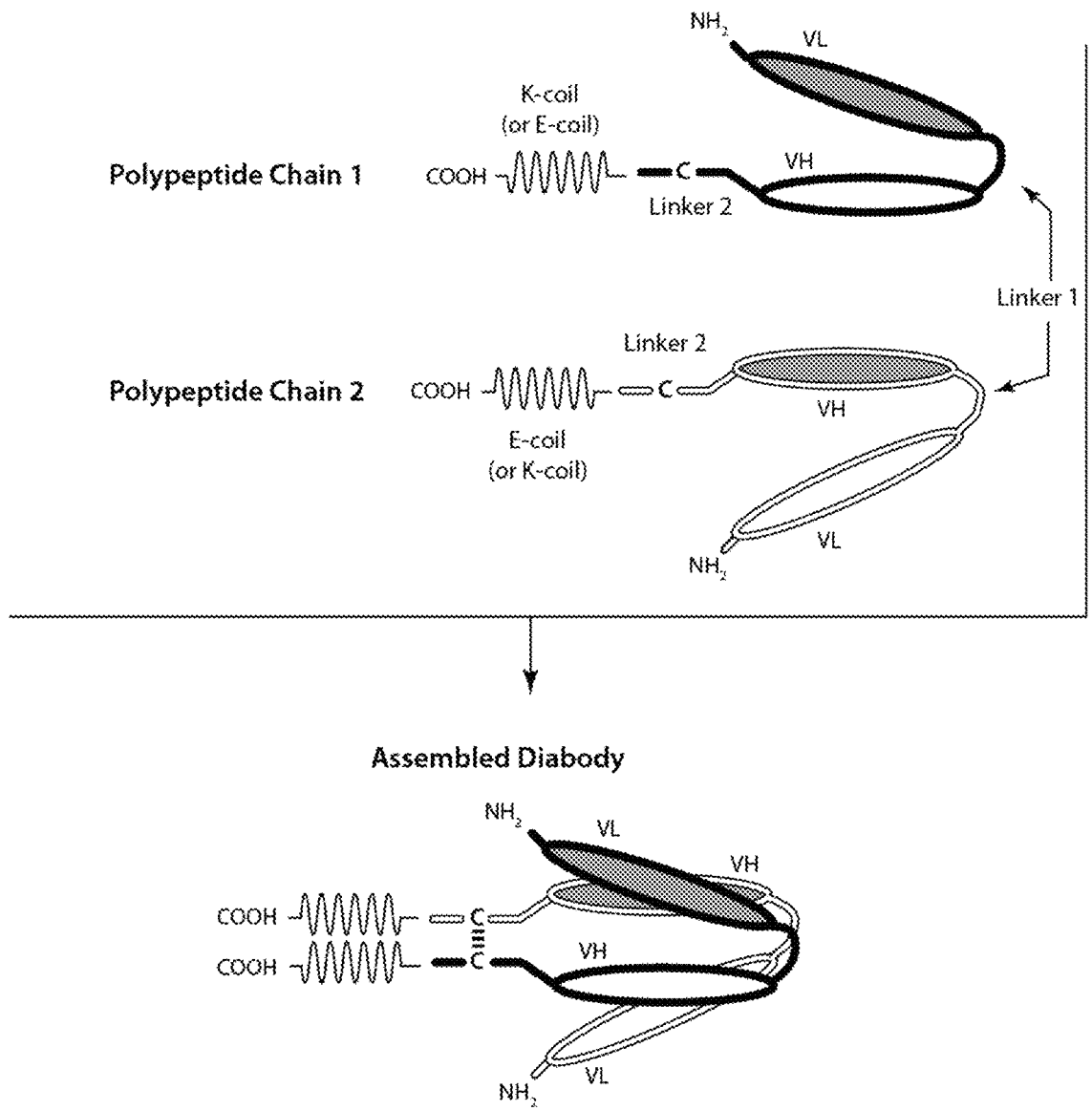
FIG. 1 illustrates the structure of a covalently associated bi-specific monovalent diabody composed of two polypeptide chains.

The present invention is directed to bi-specific monovalent diabodies that comprise two polypeptide chains and which possess one binding site specific for an epitope of CD19 and one binding site specific for an epitope of CD3 (i.e., a "CD19×CD3 bi-specific monovalent diabody"). Most preferably, such CD19×CD3 bi-specific monovalent diabodies are composed of three polypeptide chains and possess one binding site specific for an epitope of CD19 and one binding site specific for an epitope of CD3 and additionally comprise an immunoglobulin Fc Domain (i.e., a "CD19× CD3 bi-specific monovalent Fc diabody"). The bi-specific monovalent diabodies and bi-specific monovalent Fc diabodies of the present invention are capable of simultaneous binding to CD19 and CD3. The invention is directed to pharmaceutical compositions that contain such bi-specific monovalent diabodies or such bi-specific monovalent Fc diabodies. The invention is additionally directed to methods for the use of such diabodies in the treatment of disease, in particular hematologic malignancies.

A. Antibodies and Other Binding Molecules

1. Antibodies

As used herein, the term "Antibodies" encompasses not only intact polyclonal or monoclonal antibodies, but also mutants thereof, naturally occurring variants, fusion proteins comprising an antibody portion with an antigen recognition site of the required specificity, humanized antibodies, and chimeric antibodies, and any other modified configuration of the immunoglobulin molecule that comprises an antigen recognition site of the required specificity. Throughout this application, the numbering of amino acid residues of the light and heavy chains of antibodies is according to the EU index as in Kabat et al. (1992) SEQUENCES OF PROTEINS OF IMMUNOLOGICAL INTEREST, National Institutes of Health Publication No. 91-3242. As used herein, an "antigen-binding fragment of an antibody" is a portion of an antibody that possesses an at least one antigen recognition site. As used herein, the term encompasses fragments (such as Fab, Fab', F(ab')$_2$ Fv), and single chain (scFv).

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$ Fv), single chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi. In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi weekly, or weekly, or may be administered in such a way as to maintain viability in the animal (e.g., in a tissue recombinant). Alternatively, existing monoclonal antibodies and any other equivalent antibodies that are immunospecific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the bi-specific molecules of the invention as well as a chimeric antibody, a humanized antibody, or a caninized antibody, to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable Domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807, 715; 5,866,692; and 6,331,415.

2. Bi-Specific Antibodies, Multi-Specific Diabodies and DART™ Diabodies

The provision of non-mono-specific "diabodies" provides a significant advantage over antibodies: the capacity to co-ligate and co-localize cells that express different epitopes. Bivalent diabodies thus have wide-ranging applications including therapy and immunodiagnosis. Bi-valency allows for great flexibility in the design and engineering of the diabody in various applications, providing enhanced avidity to multimeric antigens, the cross-linking of differing antigens, and directed targeting to specific cell types relying on the presence of both target antigens. Due to their increased valency, low dissociation rates and rapid clearance from the circulation (for diabodies of small size, at or below ~50 kDa), diabody molecules known in the art have also shown particular use in the field of tumor imaging (Fitzgerald et al. (1997) "*Improved Tumour Targeting By Disulphide Stabilized Diabodies Expressed In Pichia pastoris*," Protein Eng. 10:1221). Of particular importance is the co-ligating of differing cells, for example, the cross-linking of cytotoxic T cells to tumor cells (Staerz et al. (1985) "*Hybrid Antibodies Can Target Sites For Attack By T Cells*," Nature 314:628- 631, and Holliger et al. (1996) "*Specific Killing Of Lymphoma Cells By Cytotoxic T-Cells Mediated By A Bispecific Diabody*," Protein Eng. 9:299-305).

Diabody epitope binding domains may also be directed to a surface determinant of a B cell, such as CD19, CD20, CD22, CD30, CD37, CD40, and CD74 (Moore, P. A. et al. (2011) "*Application Of Dual Affinity Retargeting Molecules To Achieve Optimal Redirected T-Cell Killing Of B-Cell Lymphoma*," Blood 117(17):4542-4551; Cheson, B. D. et al. (2008) "*Monoclonal Antibody Therapy For B-Cell Non-Hodgkin's Lymphoma*," N. Engl. J. Med. 359(6):613-626; Castillo, J. et al. (2008) "Newer monoclonal antibodies for hematological malignancies," Exp. Hematol. 36(7):755- 768. In many studies, diabody binding to effector cell determinants, e.g., Fcγ receptors (FcγR), was also found to activate the effector cell (Holliger et al. (1996) "*Specific Killing Of Lymphoma Cells By Cytotoxic T-Cells Mediated By A Bispecific Diabody*," Protein Eng. 9:299-305; Holliger et al. (1999) "*Carcinoembryonic Antigen (CEA)-Specific T-Cell Activation In Colon Carcinoma Induced By Anti-CD3×Anti-CEA Bispecific Diabodies And B7×Anti-CEA Bispecific Fusion Proteins*," Cancer Res. 59:2909-2916; WO 2006/113665; WO 2008/157379; WO 2010/080538; WO 2012/018687; WO 2012/162068). Normally, effector cell activation is triggered by the binding of an antigen bound antibody to an effector cell via Fc-FcγR interaction; thus, in this regard, diabody molecules may exhibit Ig-like functionality independent of whether they comprise an Fc Domain (e.g., as assayed in any effector function assay known in the art or exemplified herein (e.g., ADCC assay)). By cross-linking tumor and effector cells, the diabody not only brings the effector cell within the proximity of the tumor cells but leads to effective tumor killing (see e.g., Cao et al. (2003) "*Bispecific Antibody Conjugates In Therapeutics*," Adv. Drug. Deliv. Rev. 55:171-197).

However, the above advantages come at a salient cost. The formation of such non-mono-specific diabodies requires the successful assembly of two or more distinct and different polypeptides (i.e., such formation requires that the diabodies be formed through the heterodimerization of different polypeptide chain species). This fact is in contrast to mono-specific diabodies, which are formed through the homodimerization of identical polypeptide chains. Because at least two dissimilar polypeptides (i.e., two polypeptide species) must be provided in order to form a non-mono-specific diabody, and because homodimerization of such polypeptides leads to inactive molecules (Takemura, S. et al. (2000) "*Construction Of A Diabody (Small Recombinant Bispecific Antibody) Using A Refolding System*," Protein Eng. 13(8): 583-588), the production of such polypeptides must be accomplished in such a way as to prevent covalent bonding between polypeptides of the same species (i.e., so as to prevent homodimerization) (Takemura, S. et al. (2000) "*Construction Of A Diabody (Small Recombinant Bispecific Antibody) Using A Refolding System*," Protein Eng. 13(8): 583-588). The art has therefore taught the non-covalent association of such polypeptides (see, e.g., Olafsen et al. (2004) "*Covalent Disulfide-Linked Anti-CEA Diabody Allows Site-Specific Conjugation And Radiolabeling For Tumor Targeting Applications*," Prot. Engr. Des. Sel. 17:21- 27; Asano et al. (2004) "*A Diabody For Cancer Immunotherapy And Its Functional Enhancement By Fusion Of Human Fc Domain*," Abstract 3P-683, J. Biochem. 76(8): 992; Takemura, S. et al. (2000) "*Construction Of A Diabody (Small Recombinant Bispecific Antibody) Using A Refolding System*," Protein Eng. 13(8):583-588; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

However, the art has recognized that bi-specific diabodies composed of non-covalently associated polypeptides are unstable and readily dissociate into non-functional monomers (see, e.g., Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20):19665-19672).

In the face of this challenge, the art has succeeded in developing stable, covalently bonded heterodimeric non-mono-specific diabodies, termed DARTs™ (see, e.g., United States Patent Publications No. 2013-0295121; 2010- 0174053 and 2009-0060910; European Patent Publication No. EP 2714079; EP 2601216; EP 2376109; EP 2158221 and PCT Publications No. WO 2012/162068; WO 2012/ 018687; WO 2010/080538; and Moore, P. A. et al. (2011) "*Application Of Dual Affinity Retargeting Molecules To Achieve Optimal Redirected T-Cell Killing Of B-Cell Lymphoma*," Blood 117(17):4542-4551; Veri, M. C. et al. (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Johnson, S. et al. (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449). Such diabodies comprise two or more covalently complexed polypeptides and involve engineering one or more cysteine residues into each of the employed polypeptide species. For example, the addition of a cysteine residue to the c-terminus of such constructs has been shown to allow disulfide bonding between the polypeptide chains, stabilizing the resulting heterodimer without interfering with the binding characteristics of the bivalent molecule.

Each of the two polypeptides of the simplest DART™ comprises three Domains (FIG. 1). The first polypeptide comprises: (i) a Domain that comprises a binding region of a light chain variable Domain of the a first immunoglobulin (VL1), (ii) a second Domain that comprises a binding region of a heavy chain variable Domain of a second immunoglobulin (VH2), and (iii) a third Domain that serves to promote heterodimerization with the second polypeptide and to covalently bond the first polypeptide to the second polypeptide of the diabody. The second polypeptide contains a complementary first Domain (a VL2 Domain), a complementary second Domain (a VH1 Domain) and a third Domain that complexes with the third Domain of the first polypeptide chain in order to promote heterodimerization and covalent bonding with the first polypeptide chain. Such molecules are stable, potent and have the ability to simultaneously bind two or more antigens. They are able to promote redirected T cell mediated killing of cells expressing target antigens.

Figure 2A:
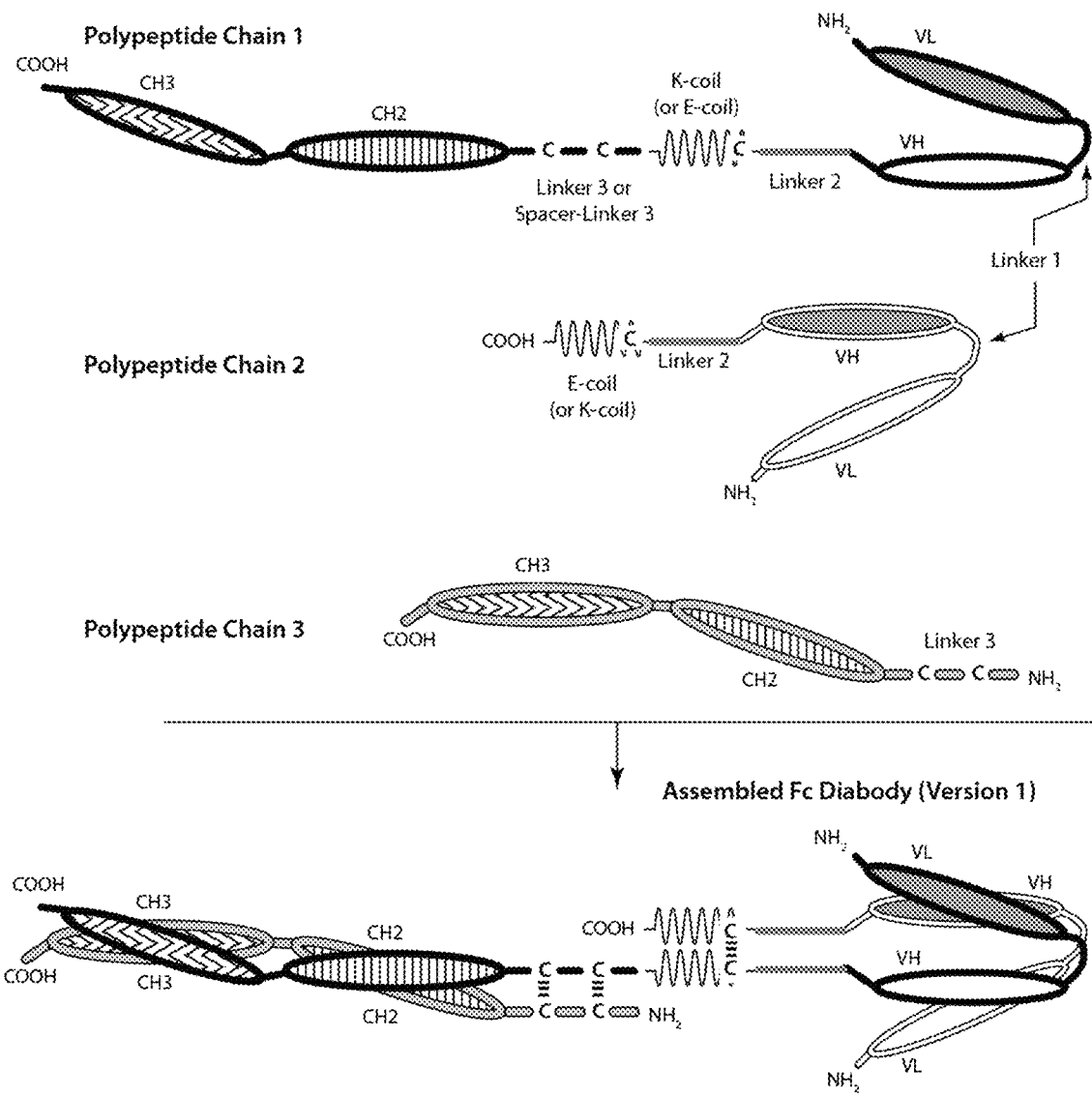
FIGS. 2A and 2B illustrate the structures of two versions of the first, second and third polypeptide chains of a three chain CD19×CD3 bi-specific monovalent Fc diabody of the present invention (Version 1, FIG. 2A; Version 2, FIG. 2B).
Figure 2B:
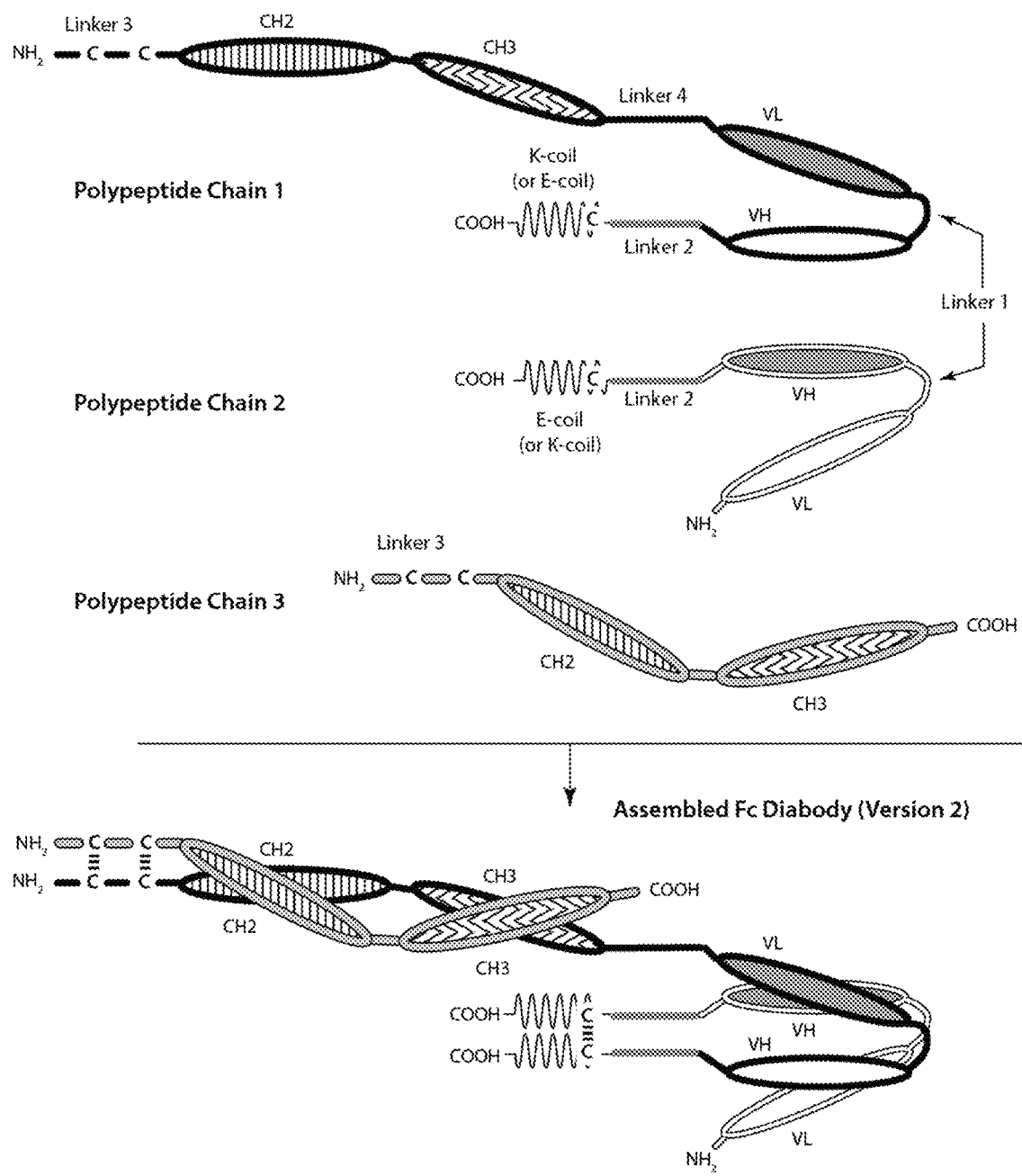

In one embodiment, the third Domains of the first and second polypeptides each contain a cysteine residue, which serves to bind the polypeptides together via a disulfide bond. The third Domain of one or both of the polypeptides may additionally possesses the sequence of a CH2-CH3 Domain, such that complexing of the diabody polypeptides forms an Fc Domain that is capable of binding to the Fc receptor of cells (such as B lymphocytes, dendritic cells, natural killer cells, macrophages, neutrophils, eosinophils, basophils and mast cells) (FIGS. 2A-2B). Many variations of such molecules have been described (see, e.g., United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538). These Fc-bearing DARTs may comprise three polypeptide chains. The first polypeptide of such a diabody contains three Domains: (i) a VL1-containing Domain, (ii) a VH2-containing Domain, (iii) a Domain that promotes heterodimerization and covalent bonding with the diabody's first polypeptide chain and (iv) a Domain containing a CH2-CH3 sequence. The second polypeptide of such DART™ contains: (i) a VL2-containing Domain, (ii) a VH1-containing Domain and (iii) a Domain that promotes heterodimerization and covalent bonding with the diabody's first polypeptide chain. The third polypeptide of such DART™ comprises a CH2-CH3 sequence. Thus, the first and second polypeptide chains of such DART™ associate together to form a VL1/VH1 binding site that is capable of binding to the epitope, as well as a VL2/VH2 binding site that is capable of binding to the second epitope. The first and second polypeptides are bonded to one another through a disulfide bond involving cysteine residues in their respective third Domains. Notably, the first and third polypeptide chains complex with one another to form an Fc Domain that is stabilized via a disulfide bond. Such diabodies have enhanced potency. Such Fc-bearing DARTs™ may have either of two orientations (Table 1):

TABLE 1

| First Orientation | 3$^{rd}$ Chain | NH$_2$—CH2—CH3—COOH |
|---|---|---|
| | 1$^{st}$ Chain | NH$_2$-VL1-VH2-Heterodimer-Promoting Domain-CH2-CH3-COOH |
| | 2$^{nd}$ Chain | NH$_2$-VL2-VH1-Heterodimer-Promoting Domain-COOH |

TABLE 1-continued

| Second Orientation | 3$^{rd}$ Chain | NH$_2$—CH2—CH3—COOH |
|---|---|---|
| | 1$^{st}$ Chain | NH$_2$-CH2-CH3-VL1-VH2-Heterodimer-Promoting Domain-COOH |
| | 2$^{nd}$ Chain | NH$_2$-VL2-VH1-Heterodimer-Promoting Domain-COOH |

B. Preferred CD19×CD3 Bi-Specific Monovalent Diabodies of the Present Invention

The present invention is particularly directed to CD19×CD3 bi-specific monovalent diabodies that are capable of simultaneous binding to CD19 and CD3, and to the uses of such molecules in the treatment of hematologic malignancies. Although non-optimized CD19×CD3 bi-specific monovalent diabodies are fully functional, analogous to the improvements obtained in gene expression through codon optimization (see, e.g., Grosjean, H. et al. (1982) "*Preferential Codon Usage In Prokaryotic Genes: The Optimal Codon-Anticodon Interaction Energy And The Selective Codon Usage In Efficiently Expressed Genes*" Gene 18(3): 199-209), it is possible to further enhance the stability and/or function of CD19×CD3 bi-specific monovalent diabodies by modifying or refining their sequences.

The preferred CD19×CD3 bi-specific monovalent diabodies of the present invention are CD19×CD3 bi-specific monovalent Fc diabodies that are composed of three polypeptide chains which associate with one another to form one binding site specific for an epitope of CD19 and one binding site specific for an epitope of CD3 (see, FIG. 2A-2B), so as to be capable of simultaneously binding to CD19 and to CD3. Thus, such diabodies bind to a "first antigen," which may be either CD3 or CD19, and a "second antigen," which is CD19 when the first epitope is CD3, and is CD3 when the first epitope is CD19.

Preferably, as shown in FIG. 2A, the first of such three polypeptide chains will contain, in the N-terminal to C-terminal direction, an N-terminus, the Antigen-Binding Domain of a Light Chain Variable Domain (VL) of a "first" antigen (either CD3 or CD19), the Antigen-Binding Domain of a Heavy Chain Variable Domain (VH) of a second antigen (CD19, if the first antigen was CD3; CD3, if the first antigen was CD19), a Heterodimer-Promoting Domain, and a C-terminus. An intervening linker peptide (Linker 1) separates the Antigen-Binding Domain of the Light Chain Variable Domain from the Antigen-Binding Domain of the Heavy Chain Variable Domain. Preferably, the Antigen-Binding Domain of the Heavy Chain Variable Domain is linked to the Heterodimer-Promoting Domain by an intervening linker peptide (Linker 2). In the case of a CD19×CD3 bi-specific monovalent Fc diabody, the C-terminus of the Heterodimer-Promoting Domain is linked to the CH2-CH3 domains of an Fc region ("Fc Domain") by an intervening linker peptide (Linker 3) or by an intervening spacer-linker peptide (Spacer-Linker 3). Most preferably, the first of the three polypeptide chains will thus contain, in the N-terminal to C-terminal direction: VL$_{First\ Antigen}$-Linker 1-VH$_{Second\ Antigen}$-Linker 2-Heterodimer-Promoting Domain—Spacer-Linker 3-Fc Domain.

Alternatively, as shown in FIG. 2B, the first of such three polypeptide chains will contain, in the N-terminal to C-terminal direction, an N-terminus, Linker 3, the CH2-CH3 domains of an Fc region ("Fc Domain"), an intervening spacer peptide (Linker 4), having, for example the amino acid sequence: APSSS (SEQ ID NO:47) or the amino acid sequence APSSSPME (SEQ ID NO:48), the Antigen-Binding Domain of a Light Chain Variable Domain (VL) of the first antigen (either CD3 or CD19), the Antigen-Binding Domain of a Heavy Chain Variable Domain (VH) of the second antigen (CD19, if the first antigen was CD3; CD3, if the first antigen was CD19), a Heterodimer-Promoting Domain, and a C-terminus. An intervening linker peptide (Linker 1) separates the Antigen-Binding Domain of the Light Chain Variable Domain from the Antigen-Binding Domain of the Heavy Chain Variable Domain. Preferably, the Antigen-Binding Domain of the Heavy Chain Variable Domain is linked to the Heterodimer-Promoting Domain by an intervening linker peptide (Linker 2). Most preferably, the first of the three polypeptide chains will thus contain, in the N-terminal to C-terminal direction: Linker 3-Fc Domain-Linker 4-VL$_{First\ Antigen}$-Linker 1-VH$_{Second\ Antigen}$-Linker 2-Heterodimer-Promoting Domain.

Preferably, the second of such three polypeptide chains will contain, in the N-terminal to C-terminal direction, an N-terminus, the Antigen-Binding Domain of a Light Chain Variable Domain (VL) of the second antigen, the Antigen-Binding Domain of a Heavy Chain Variable Domain (VH) of the first antigen, a Heterodimer-Promoting Domain and a C-terminus. An intervening linker peptide (Linker 1) separates the Antigen-Binding Domain of the Light Chain Variable Domain from the Antigen-Binding Domain of the Heavy Chain Variable Domain. Preferably, the Antigen-Binding Domain of the Heavy Chain Variable Domain is linked to the Heterodimer-Promoting Domain by an intervening linker peptide (Linker 2). Most preferably, the second of the three polypeptide chains will thus contain, in the N-terminal to C-terminal direction: VL$_{Second\ Antigen}$-Linker 1-VH$_{First\ Antigen}$-Linker 2-Heterodimer-Promoting Domain.

Preferably, the third of such three polypeptide chains will contain the linker peptide (Linker 3) and the CH2-CH3 domains of an Fc region ("Fc Domain").

The Antigen-Binding Domain of the Light Chain Variable Domain of the first polypeptide chain interacts with the Antigen-Binding Domain of the Heavy Chain Variable Domain of the second polypeptide chain in order to form a functional antigen-binding site that is specific for the first antigen (i.e., either CD19 or CD3). Likewise, the Antigen-Binding Domain of the Light Chain Variable Domain of the second polypeptide chain interacts with the Antigen-Binding Domain of the Heavy Chain Variable Domain of the first polypeptide chain in order to form a second functional antigen-binding site that is specific for the second antigen (i.e., either CD3 or CD19, depending upon the identity of the first antigen). Thus, the selection of the Antigen-Binding Domain of the Light Chain Variable Domain and the Antigen-Binding Domain of the Heavy Chain Variable Domain of the first and second polypeptide chains are coordinated, such that the two polypeptide chains collectively comprise Antigen-Binding Domains of light and Heavy Chain Variable Domains capable of binding to CD19 and CD3.

1. Preferred Linkers

Most preferably, the length of Linker 1, which separates such VL and VH domains of a polypeptide chain is selected to substantially or completely prevent such VL and VH domains from binding to one another. Thus the VL and VH domains of the first polypeptide chain are substantially or completely incapable of binding to one another. Likewise, the VL and VH domains of the second polypeptide chain are substantially or completely incapable of binding to one another. A preferred intervening spacer peptide (Linker 1) has the sequence (SEQ ID NO:1): GGGSGGGG.

The purpose of Linker 2 is to separate the VH Domain of a polypeptide chain from the Heterodimer-Promoting Domain of that polypeptide chain. Any of a variety of linkers can be used for the purpose of Linker 2. A preferred sequence for such Linker 2 has the amino acid sequence: ASTKG (SEQ ID NO:2), which is derived from the IgG CH1 domain, or GGCGGG (SEQ ID NO:3), which possesses a cysteine residue that may be used to covalently bond the first and second polypeptide chains to one another via a disulfide bond. Since the Linker 2, ASTKG (SEQ ID NO:2) does not possess such a cysteine, the use of such Linker 2 is preferably associated with the use of a cysteine-containing Heterodimer-Promoting Domain, such as the E-coil of SEQ ID NO:12 or the K-coil of SEQ ID NO:13 (see below).

The purpose of Linker 3 is to separate the Heterodimer-Promoting Domain of a polypeptide chain from the Fc Domain of that polypeptide chain. Any of a variety of linkers can be used for the purpose of Linker 3. A preferred sequence for such Linker 3 has the amino acid sequence: DKTHTCPPCP (SEQ ID NO:4). A preferred sequence for Spacer-Linker 3 has the amino acid sequence: GGGDKTH-TCPPCP (SEQ ID NO:5).

2. Preferred Heterodimer-Promoting Domains

The formation of heterodimers of the first and second polypeptide chains can be driven by the inclusion of Heterodimer-Promoting Domains. Such domains include GVE-PKSC (SEQ ID NO:6) or VEPKSC (SEQ ID NO:7) on one polypeptide chain and GFNRGEC (SEQ ID NO:8) or FNRGEC (SEQ ID NO:9) on the other polypeptide chain (US2007/0004909).

More preferably, however, the Heterodimer-Promoting Domains of the present invention are formed from one, two, three or four tandemly repeated coil domains of opposing charge that comprise a sequence of at least six, at least seven or at least eight charged amino acid residues (Apostolovic, B. et al. (2008) "*pH-Sensitivity of the E3/K3 Heterodimeric Coiled Coil*," Biomacromolecules 9:3173-3180; Arndt, K. M. et al. (2001) "*Helix-stabilized Fv (hsFv) Antibody Fragments: Substituting the Constant Domains of a Fab Fragment for a Heterodimeric Coiled-coil Domain*," J. Molec. Biol. 312:221-228; Arndt, K. M. et al. (2002) "*Comparison of In Vivo Selection and Rational Design of Heterodimeric Coiled Coils*," Structure 10:1235-1248; Boucher, C. et al. (2010) "*Protein Detection By Western Blot Via Coiled-Coil Interactions*," Analytical Biochemistry 399:138-140; Cachia, P. J. et al. (2004) "*Synthetic Peptide Vaccine Development: Measurement Of Polyclonal Antibody Affinity And Cross-Reactivity Using A New Peptide Capture And Release System For Surface Plasmon Resonance Spectroscopy*," J. Mol. Recognit. 17:540-557; De Crescenzo, G. D. et al. (2003) "*Real-Time Monitoring of the Interactions of Two-Stranded de novo Designed Coiled-Coils: Effect of Chain Length on the Kinetic and Thermodynamic Constants of Binding*," Biochemistry 42:1754-1763; Fernandez-Rodriquez, J. et al. (2012) "*Induced Heterodimerization And Purification Of Two Target Proteins By A Synthetic Coiled-Coil Tag*," Protein Science 21:511-519; Ghosh, T. S. et al. (2009) "*End-To-End And End-To-Middle Interhelical Interactions: New Classes Of Interacting Helix Pairs In Protein Structures*," Acta Crystallographica D65:1032-1041; Grigoryan, G. et al. (2008) "*Structural Specificity In Coiled-Coil Interactions*," Curr. Opin. Struc. Biol. 18:477-483; Litowski, J. R. et al. (2002) "*Designing Heterodimeric Two-Stranded α-Helical Coiled-Coils: The Effects Of Hydrophobicity And α-Helical Propensity On Protein Folding, Stability, And Specificity*," J. Biol. Chem. 277:37272-37279; Steinkruger, J. D. et al. (2012) "*The d'--d--d' Vertical Triad is Less Discriminating Than the a'--a--a' Vertical Triad in the Antiparallel Coiled-coil Dimer Motif*" J. Amer. Chem. Soc. 134(5):2626-2633; Straussman, R. et al. (2007) "*Kinking the Coiled Coil—Negatively Charged Residues at the Coiled-coil Interface*," J. Molec. Biol. 366:1232-1242;

Tripet, B. et al. (2002) "*Kinetic Analysis of the Interactions between Troponin C and the C-terminal Troponin I Regulatory Region and Validation of a New Peptide Delivery/Capture System used for Surface Plasmon Resonance*," J. Molec. Biol. 323:345-362; Woolfson, D. N. (2005) "*The Design Of Coiled-Coil Structures And Assemblies*," Adv. Prot. Chem. 70:79-112; Zeng, Y. et al. (2008) "*A Ligand-Pseudoreceptor System Based On de novo Designed Peptides For The Generation Of Adenoviral Vectors With Altered Tropism*," J. Gene Med. 10:355-367).

Such repeated coil domains may be exact repeats or may have substitutions. For example, the Heterodimer-Promoting Domain of the first polypeptide chain may comprise a sequence of eight negatively charged amino acid residues and the Heterodimer-Promoting Domain of the second polypeptide chain may comprise a sequence of eight positively charged amino acid residues (or vice versa). It is immaterial which coil is provided to the first or second polypeptide chains, provided that a coil of opposite charge is used for the other polypeptide chain. However, a preferred CD19×CD3 bi-specific monovalent diabody of the present invention has a first polypeptide chain having a negatively charged coil. The positively charged amino acid may be lysine, arginine, histidine, etc. and/or the negatively charged amino acid may be glutamic acid, aspartic acid, etc. The positively charged amino acid is preferably lysine and/or the negatively charged amino acid is preferably glutamic acid. It is possible for only a single Heterodimer-Promoting Domain to be employed (since such domain will inhibit homodimerization and thereby promote heterodimerization), however, it is preferred for both the first and second polypeptide chains of the diabodies of the present invention to contain Heterodimer-Promoting Domains.

In a preferred embodiment, one of the Heterodimer-Promoting Domains will comprise four tandem "E-coil" helical domains (SEQ ID NO:10: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:11: KVAALKE-KVAALKE-KVAALKE-KVAALKE), whose lysine residues will form a positive charge at pH 7. The presence of such charged domains promotes association between the first and second polypeptides, and thus fosters heterodimerization. Especially preferred is a Heterodimer-Promoting Domain in which one of the four tandem "E-coil" helical domains of SEQ ID NO:10 has been modified to contain a cysteine residue: EVAACEK-EVAALEK-EVAALEK-EVAALEK (SEQ ID NO:12). Likewise, especially preferred is a Heterodimer-Promoting Domain in which one of the four tandem "K-coil" helical domains of SEQ ID NO:11 has been modified to contain a cysteine residue: KVAACKE-KVAALKE-KVAALKE-KVAALKE (SEQ ID NO:13).

3. Covalent Bonding of the Polypeptide Chains

The CD19×CD3 bi-specific monovalent diabodies of the present invention are engineered so that their first and second polypeptide chains covalently bond to one another via one or more cysteine residues positioned along their length. Such cysteine residues may be introduced into the intervening linker that separates the VL and VH domains of the polypeptides. Alternatively, Linker 2 may contain a cysteine residue. Additionally or alternatively, Linker 3 may contain a cysteine residue, as in SEQ ID NO:4 or SEQ ID NO:5. Most preferably, one or more coil domains of the Heterodimer-Promoting Domain will be substituted to contain a cysteine residue as in SEQ ID NO:12 or SEQ ID NO:13.

In particular embodiments, the CD19×CD3 bi-specific monovalent diabodies of the present invention may further have an Albumin-Binding Domain to extend half-life in vivo.

4. Preferred Fc Domains

The Fc Domain of the CD19×CD3 bi-specific monovalent Fc diabodies of the present invention may be either a complete Fc region (e.g., a complete IgG Fc region) or only a fragment of a complete Fc region. Although the Fc Domain of the bi-specific monovalent Fc diabodies of the present invention may possess the ability to bind to one or more Fc receptors (e.g., FcγR(s)), more preferably such Fc Domain will cause reduced binding to FcγRIA (CD64), FcγRIIA (CD32A), FcγRIIB (CD32B), FcγRIIIA (CD16a) or FcγRIIIB (CD16b) (relative to the binding exhibited by a wild-type Fc region) or will substantially eliminate the ability of such Fc Domain to bind to such receptor(s). The Fc Domain of the bi-specific monovalent Fc diabodies of the present invention may include some or all of the CH2 Domain and/or some or all of the CH3 Domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bi-specific monovalent Fc diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 Domain linked to a CH2 Domain, etc.).

In a preferred embodiment the first and third polypeptide chains of the CD19×CD3 bi-specific monovalent Fc diabodies of the present invention each comprise CH2-CH3 domains that complex together to form an immunoglobulin (IgG) Fc Domain. The amino acid sequence of the CH2-CH3 domain of human IgG1 is (SEQ ID NO:14):

```
APELLGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGK
```

Thus the CH2 and/or CH3 Domains of the first and third polypeptide chains may both be composed of SEQ ID NO:14, or a variant thereof.

In particular, it is preferred for the CH2-CH3 domains of the first and third polypeptide chains of the CD19×CD3 bi-specific monovalent Fc diabodies of the present invention to exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO:14). Fc variants and mutant forms capable of mediating such altered binding are well known in the art and include amino acid substitutions at positions 234 and 235, a substitution at position 265 or a substitution at position 297 (see, for example, U.S. Pat. No. 5,624,821, herein incorporated by reference). In a preferred embodiment the CH2-CH3 Domain of the first and/or third polypeptide chains of the CD19×CD3 bi-specific monovalent Fc diabodies of the present invention include a substitution at position 234 with alanine and 235 with alanine.

The CH2 and/or CH3 Domains of the first and third polypeptide chains need not be identical in sequence, and advantageously are modified to foster complexing between the two polypeptide chains. For example, an amino acid substitution (preferably a substitution with an amino acid comprising a bulky side group forming a 'knob', e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the bi-specific monovalent Fc diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety). Preferably the 'knob' is engineered into the CH2-CH3 Domains of the first polypeptide chain and the 'hole' is engineered into the CH2-CH3 Domains of the third polypeptide chain. Thus, the 'knob' will help in preventing the first polypeptide chain from homodimerizing via its CH2 and/or CH3 Domains. As the third polypeptide chain preferably contains the 'hole' substitution it will heterodimerize with the first polypeptide chain as well as homodimerize with itself. A preferred knob is created by modifying a native IgG Fc Domain to contain the modification T366W. A preferred hole is created by modifying a native IgG Fc Domain to contain the modification T366S, L368A and Y407V. To aid in purifying the third polypeptide chain homodimer from the final bi-specific monovalent Fc diabody comprising the first, second and third polypeptide chains, the protein A binding site of the CH2 and CH3 Domains of the third polypeptide chain is preferably mutated by amino acid substitution at position 435 (H435R). Thus, the third polypeptide chain homodimer will not bind to protein A, whereas the bi-specific monovalent Fc diabody will retain its ability to bind protein A via the protein A binding site on the first polypeptide chain.

A preferred sequence for the CH2 and CH3 Domains of the first polypeptide chain of the CD19×CD3 bi-specific monovalent Fc diabodies of the present invention will have the "knob-bearing" sequence (SEQ ID NO:15):

```
APE_AA_GGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGK
```

A preferred sequence for the CH2 and CH3 Domains of the third polypeptide chain of the CD19×CD3 bi-specific monovalent Fc diabodies of the present invention will have the "hole-bearing" sequence (SEQ ID NO:16):

```
APE_AA_GGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGK
```

As will be noted, the CH2-CH3 Domains of SEQ ID NO:15 and SEQ ID NO:16 include a substitution at position 234 with alanine and 235 with alanine, and thus form an Fc Domain exhibit decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO: 14).

It is preferred that the first polypeptide chain will have a "knob-bearing" CH2-CH3 sequence, such as that of SEQ ID NO:15. However, as will be recognized, a "hole-bearing" CH2-CH3 Domain (e.g., SEQ ID NO:16) could be employed in the first polypeptide chain, in which case, a "knob-bearing" CH2-CH3 Domain (e.g., SEQ ID NO:15) would be employed in the third polypeptide chain.

5. Preferred CD19 Variable Domains

The Antigen-Binding Domain of the Light Chain Variable Domain of any anti-CD19 antibody may be used in accordance with the present invention. Preferably, however, such $VL_{CD19}$ Domain will have the amino acid sequence (SEQ ID NO:17):

```
ENVLTQSPAT LSVTPGEKAT ITCRASQSVS YMHWYQQKPG

QAPRLLIYDA SNRASGVPSR FSGSGSGTDH TLTISSLEAE

DAATYYCFQG SVYPFTFGQG TKLEIK
``` wherein the underlined sequences are, respectively, CDR1, CDR2, and CDR3, thereof:

$VL_{CD19}$ CDR1:

(SEQ ID NO: 18)
RASQSVSYMH $VL_{CD19}$ CDR2:

(SEQ ID NO: 19)
DASNRAS $VL_{CD19}$ CDR3:

(SEQ ID NO: 20)
FQGSVYPFT

Likewise, the Antigen-Binding Domain of the Heavy Chain Variable Domain of any anti-CD19 antibody may be used in accordance with the present invention. Preferably, however, such VH$_{CD19}$ Domain will have the amino acid sequence (SEQ ID NO:21):

```
                                           (SEQ ID NO: 22)
QVTLRESGPA LVKPTQTLTL TCTFSGFSLS TSGMGVGWIR

QPPGKALEWL AHIWWDDDKR YNPALKSRLT ISKDTSKNQV

FLTMTNMDPV DTATYYCARM ELWSYYFDYW GQGTTVTVSS
``` wherein the underlined sequences are, respectively, CDR1, CDR2, and CDR3, thereof:

```
VH_CD19 CDR1:
                                           (SEQ ID NO: 22)
TSGMGVG

VH_CD19 CDR2:
                                           (SEQ ID NO: 23)
HIWWDDDKRYNPALKS

VH_CD19 CDR3:
                                           (SEQ ID NO: 24)
MELWSYYFDY
```

6. Preferred CD3 Variable Domains

The Antigen-Binding Domain of the Light Chain Variable Domain of any anti-CD3 antibody may be used in accordance with the present invention. Preferably, however, such VL$_{CD3}$ Domain will have the amino acid sequence (SEQ ID NO:25):

```
QAVVTQEPSL TVSPGGTVTL TCRSSTGAVT TSNYANWVQQ

KPGQAPRGLI GGTNKRAPWT PARFSGSLLG GKAALTITGA

QAEDEADYYC ALWYSNLWVF GGGTKLTVLG
``` wherein the underlined sequences are, respectively, CDR1, CDR2, and CDR3, thereof:

```
VL_CD3 CDR1:
                                           (SEQ ID NO: 26)
RSSTGAVTTSNYAN

VL_CD3 CDR2:
                                           (SEQ ID NO: 27)
GTNKRAP

VL_CD3 CDR3:
                                           (SEQ ID NO: 28)
ALWYSNLWV
```

Likewise, the Antigen-Binding Domain of the Heavy Chain Variable Domain of any anti-CD3 antibody may be used in accordance with the present invention. Preferably, however, such VH$_{CD3}$ Domain will have the amino acid sequence (SEQ ID NO:29):

```
EVQLVESGGG LVQPGGSLRL SCAASGFTFS TYAMNWVRQA

PGKGLEWVGR IRSKYNNYAT YYADSVKGRF TISRDDSKNS

LYLQMNSLKT EDTAVYYCVR HGNFGNSYVS WFAYWGQGTL

VTVSS
``` wherein the underlined sequences are, respectively, CDR1, CDR2, and CDR3, thereof:

```
VH_CD3 CDR1:
                                           (SEQ ID NO: 30)
TYAMN

VH_CD3 CDR2:
                                           (SEQ ID NO: 31)
RIRSKYNNYATYYADSVKG

VH_CD3 CDR3:
                                           (SEQ ID NO: 32)
HGNFGNSYVSWFAY
```

7. Optional Albumin-Binding Domain

As disclosed in WO 2012/018687, in order to further improve the in vivo pharmacokinetic properties of the CD19×CD3 bi-specific monovalent diabodies and CD19× CD3 bi-specific monovalent diabodies Fc diabodies of the present invention, such diabodies may be modified to contain a polypeptide portion of a serum-binding protein at one or more of the termini of the diabody. Most preferably, such polypeptide portion of a serum-binding protein will be installed at the C-terminus of the diabody. A particularly preferred polypeptide portion of a serum-binding protein for this purpose is the Albumin-Binding Domain (ABD) from streptococcal protein G. The Albumin-Binding Domain 3 (ABD3) of protein G of Streptococcus strain G148 is particularly preferred.

The Albumin-Binding Domain 3 (ABD3) of protein G of Streptococcus strain G148 consists of 46 amino acid residues forming a stable three-helix bundle and has broad albumin-binding specificity (Johansson, M. U. et al. (2002) "Structure, Specificity, And Mode Of Interaction For Bacterial Albumin-Binding Modules," J. Biol. Chem. 277(10): 8114-8120). Albumin is the most abundant protein in plasma and has a half-life of 19 days in humans. Albumin possesses several small molecule binding sites that permit it to non-covalently bind to other proteins and thereby extend their serum half-lives.

Thus, the second polypeptide chain of such a CD19×CD3 bi-specific monovalent diabody or bi-specific monovalent Fc diabody having an Albumin-Binding Domain contains a linker (Linker 4), which separates the E-coil (or K-coil) of such polypeptide chain from the Albumin-Binding Domain. A preferred sequence for such Linker 4 is SEQ ID NO:33: GGGS. A preferred Albumin-Binding Domain (ABD) has the sequence (SEQ ID NO:34):

```
LAEAKVLANRELDKYGVSDYYKNLIDNAKSAEGVKALIDEILAALP.
```

C. Illustrative CD19×CD3 Bi-Specific Monovalent Fc Diabody, "DART-A"

The invention provides an illustrative CD19×CD3 bi-specific monovalent Fc diabody capable of simultaneously and specifically binding to CD19 and to CD3. This illustrative diabody is denoted as "DART-A." The diabodies of the present invention were found to exhibit enhanced functional activity relative to other CD19×CD3 diabodies.

As indicated above, the CD19×CD3 bi-specific monovalent Fc diabodies of the present invention comprise three polypeptide chains. The first polypeptide chain of DART-A comprises, in the N-terminal to C-terminal direction, an N-terminus, a VL domain of a monoclonal antibody capable of binding to CD19 (VL$_{CD19}$) (SEQ ID NO:17), an intervening linker peptide (Linker 1; GGGSGGGG (SEQ ID NO:1)), a VH domain of a monoclonal antibody capable of binding to CD3 (VH$_{CD3}$) (SEQ ID NO:29), an intervening linker peptide (Linker 2; ASTKG (SEQ ID NO:2)), a Heterodimer-Promoting (E-coil) Domain (EVAACEK-EVAALEK-EVAALEK-EVAALEK (SEQ ID NO:12)), an intervening linker peptide (Spacer-Linker 3; GGGDKTHTCPPCP (SEQ ID NO:5)), a polypeptide that contains the "knob-bearing" CH2 and CH3 Domains (Fc Domain sequence, SEQ ID NO:15) and a C-terminus.

Thus, the first polypeptide chain of DART-A is composed of: SEQ ID NO:17-SEQ ID NO:1-SEQ ID NO:29-SEQ ID NO:2-SEQ ID NO:12-SEQ ID NO:5-SEQ ID NO:15.

The amino acid sequence of the first polypeptide of DART-A is (SEQ ID NO:35):

ENVLTQSPATLSVTPGEKATITCRASQSVSYMHWYQQKPGQAPRLLIYDA

SNRASGVPSRFSGSGSGTDHTLTISSLEAEDAATYYCFQGSVYPFTFGQG

TKLEIKGGGSGGGGEVQLVESGGGLVQPGGSLRLSCAASGFTFSTYAMNW

VRQAPGKGLEWVGRIRSKYNNYATYYADSVKGRFTISRDDSKNSLYLQMN

SLKTEDTAVYYCVRHGNFGNSYVSWFAYWGQGTLVTVSSASTKGEVAACE

KEVAALEKEVAALEKEVAALEKGGGDKTHTCPPCPAPEAAGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLWCLVKGFYPSDIAVEWESNGQPENNYKTTP

PVLDSDGSFFLYSKLTVDKSRWQQGNVFSCSVMHEALHNHYTQKSLSLSP

GK

A preferred polynucleotide encoding such a polypeptide is (SEQ ID NO:36):

gagaatgtgctcacacagtccctgcaactctgagcgtaactccagggga gaaggccaccatcacgtgtagagcctcccagagtgtgagctacatgcact ggtatcagcagaaacctggacaagctcccaggttgctgatctatgacgcg agcaaccgggctagtggcgttccatcccggttttctggctcaggatctgg cactgaccacaccctcaccatatccagccttgaagccgaagatgccgcaa cctactactgctttcaggggagtgtgtatcccttcacattcggtcaggt acaaagctggagattaagggtggaggatccggcggcggaggcgaggtgca gctggtggagtctgggggaggcttggtccagcctggagggtccctgagac tctcctgtgcagcctctggattcaccttcagcacatacgctatgaattgg gtccgccaggctccagggaaggggctggagtgggttggaaggatcaggtc caagtacaacaattatgcaacctactatgccgactctgtgaagggtagat tcaccatctcaagagattgattcaaagaactcactgtatctgcaaatgaac agcctgaaaaccgaggacacggccgtgtattactgtgtgagacacggtaa cttcggcaattcttacgtgtcttggtttgcttattggggacaggggacac tggtgactgtgtcttccgcctccaccaagggcgaagtggccgcatgtgag aaagaggttgctgctttggagaaggaggtcgctgcacttgaaaaggagt cgcagccctggagaaaggcggcggggacaaaactcacacatgcccaccgt gcccagcacctgaagccgcgggggaccgtcagtcttcctcttccccca aaacccaaggacaccctcatgatctcccggacccctgaggtcacatgcgt ggtggtggacgtgagccacgaagaccctgaggtcaagttcaactggtacg tggacggcgtggaggtgcataatgccaagacaaagccgcggaggagcag tacaacagcacgtaccgtgtggtcagcgtcctcaccgtcctgcaccagga ctggctgaatggcaaggagtacaagtgcaaggtctccaacaaagccctcc cagcccccatcgagaaaaccatctccaaagccaaagggcagccccgagaa ccacaggtgtacaccctgccccatcccgggaggagatgaccaagaacca ggtcagcctgtggtgcctggtcaaaggcttctatcccagcgacatcgccg tggagtgggagagcaatgggcagccggagaacaactacaagaccacgcct cccgtgctggactccgacggctccttcttcctctacagcaagctcaccgt ggacaagagcaggtggcagcaggggaacgtcttctcatgctccgtgatgc atgaggctctgcacaaccactacacgcagaagagcctctccctgtctccg ggtaaa The second polypeptide chain of DART-A comprises, in the N-terminal to C-terminal direction, an N-terminus, a VL domain of a monoclonal antibody capable of binding to CD3 (VL$_{CD3}$) (SEQ ID NO:25), an intervening linker peptide (Linker 1; GGGSGGGG (SEQ ID NO:1)), a VH domain of a monoclonal antibody capable of binding to CD19 (VH$_{CD19}$) (SEQ ID NO:21), an intervening linker peptide (Linker 2; ASTKG (SEQ ID NO:2)), a Heterodimer-Promoting (K-coil) Domain (KVAACKE-KVAALKE-KVAALKE-KVAALKE (SEQ ID NO:13) and a C-terminus.

Thus, the second polypeptide of DART-A is composed of: SEQ ID NO:25-SEQ ID NO:1-SEQ ID NO:21-SEQ ID NO:2-SEQ ID NO:13.

The amino acid sequence of the second polypeptide of DART-A is (SEQ ID NO:37):

QAVVTQEPSLTVSPGGIVTLICRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGQVTLRESGPALVKPTQTLTLICTFSGFSLSTS

GMGVGWIRQPPGKALEWLAHIWWDDDKRYNPALKSRLTISKDTSKNQVFL

TMTNMDPVDTATYYCARMELWSYYFDYWGQGTIVIVSSASTKGKVAACKE

KVAALKEKVAALKEKVAALKE

A preferred polynucleotide encoding such a polypeptide has the sequence (SEQ ID NO:38):

caggctgtggtgactcaggagccttcactgaccgtgtcccaggcggaac tgtgaccctgacatgcagatccagcacaggcgcagtgaccacatctaact acgccaattgggtgcagcagaagccaggacaggcaccaaggggcctgatc gggggtacaaacaaaagggctccctggaccctgcacggttttctggaag tctgctgggcgaaaggccgctctgactattaccggggcacaggccgagg acgaagccgattactattgtgctctgtggtatagcaatctgtgggtgttc ggggtggcacaaaactgactgtgctggggggtggatccggcggagg tggacaggtgacactgagggaatctggtccagctctggtgaaacccactc agacgctcactctcacttgcacctttagtgggttctcactgtccacatct -continued
```
ggcatgggagtaggctggattcgacagccacctgggaaagccttggagtg gcttgcccacatctggtgggatgacgacaagcggtataatcccgcactga agagcagactgaccatcagcaaggatacatccaagaaccaggtgtttctg accatgaccaacatggaccctgtcgatacagccacctactattgtgctcg catggagttgtggtcctactacttcgactattggggacaaggcacaaccg tgactgtctcatccgcctccaccaagggcaaagtggccgcatgtaaggag aaagttgctgctttgaaagagaaggtcgccgcacttaaggaaaaggtcgc agccctgaaagag
```

The third polypeptide chain of DART-A comprises, in the N-terminal to C-terminal direction, an N-terminus, a peptide (Linker 3; DKTHTCPPCP (SEQ ID NO:4)), a polypeptide that contains the "hole-bearing" CH2 and CH3 Domains (Fc Domain sequence, SEQ ID NO:16) and a C-terminus.

Thus, the third polypeptide of DART-A is composed of: SEQ ID NO:4-SEQ ID NO:16.

The amino acid sequence of the third polypeptide of DART-A is (SEQ ID NO:39):

```
DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLSCAVK

GFYPSDIAVEWESNGQPENNYKTTPPVLDSDGSFFLVSKLTVDKSRWQQG

NVFSCSVMHEALHNRYTQKSLSLSPGK
```

A preferred polynucleotide that encodes such a polypeptide has the sequence (SEQ ID NO:40):

```
gacaaaactcacacatgcccaccgtgcccagcacctgaagccgcgggggg accgtcagtcttcctcttccccccaaaacccaaggacaccctcatgatct cccggacccctgaggtcacatgcgtggtggtggacgtgagccacgaagac cctgaggtcaagttcaactggtacgtggacggcgtggaggtgcataatgc caagacaaagccgcgggaggagcagtacaacagcacgtaccgtgtggtca gcgtcctcaccgtcctgcaccaggactggctgaatggcaaggagtacaag tgcaaggtctccaacaaagccctcccagcccccatcgagaaaaccatctc caaagccaaagggcagccccgagaaccacaggtgtacaccctgcccccat cccgggaggagatgaccaagaaccaggtcagcctgagttgcgcagtcaaa ggcttctatcccagcgacatcgccgtggagtgggagagcaatgggcagcc ggagaacaactacaagaccacgcctcccgtgctggactccgacggctcct tcttcctcgtcagcaagctcaccgtggacaagagcaggtggcagcagggg aacgtcttctcatgctccgtgatgcatgaggctctgcacaaccgctacac gcagaagagcctctccctgtctccgggtaaa
```

D. Control DARTS

In order to more meaningfully demonstrate the properties of the CD19×CD3 bi-specific monovalent diabodies of the present invention, two Control DARTS were constructed. The first control DART ("Control DART 1") is capable of binding to fluorescein and CD3. The second control DART ("Control DART 2") is capable of binding to fluorescein and CD19.

The anti-fluorescein antibody used to form Control DART 1 and 2 was antibody 4-4-20 (Gruber, M. et al. (1994) "*Efficient Tumor Cell Lysis Mediated By A Bispecific Single Chain Antibody Expressed In Escherichia coli*," J. Immunol. 152(11):5368-5374; Bedzyk, W. D. et al. (1989) "*Comparison Of Variable Region Primary Structures Within An Anti-Fluorescein Idiotype Family*," J. Biol. Chem. 264(3): 1565-1569) were used in control diabodies. The amino acid sequences of the variable light and variable heavy Domains of anti-fluorescein antibody 4-4-20 are as follows:

Amino Acid Sequence of the Variable Light Chain Domain of Anti-Fluorescein Antibody 4-4-20 (SEQ ID NO:41):

```
DVVMTQTPFS LPVSLGDQAS ISCRSSQSLV HSNGNTYLRW

YLQKPGQSPK VLIYKVSNRF SGVPDRFSGS GSGTDFTLKI

SRVEAEDLGV YFCSQSTHVP WTFGGGTKLE IK
```

Amino Acid Sequence of the Variable Heavy Chain Domain of Anti-Fluorescein Antibody 4-4-20 (SEQ ID NO:42):

```
EVKLDETGGG LVQPGRPMKL SCVASGFTFS DYWMNWVRQS

PEKGLEWVAQ IRNKPYNYET YYSDSVKGRF TISRDDSKSS

VYLQMNNLRV EDMGIYYCTG SYYGMDYWGQ GTSVTVSS
```

1. Control DART 1 (Fluorescein×CD3)

The first polypeptide chain of Control DART 1 comprises, in the N-terminal to C-terminal direction, an N-terminus, a VL domain of a monoclonal antibody capable of binding to fluorescein (VL$_{4-4-20}$) (SEQ ID NO:41), an intervening linker peptide (Linker 1; GGGSGGGG (SEQ ID NO:1)), a VH domain of a monoclonal antibody capable of binding to CD3 (VH$_{CD3}$) (SEQ ID NO:29), an intervening linker peptide (Linker 2; GGCGGG (SEQ ID NO:3)), a Heterodimer-Promoting (E-coil) Domain (EVAALEK-EVAALEK-EVAALEK-EVAALEK (SEQ ID NO:10)), an intervening linker peptide (Spacer-Linker 3; GGGDKTHTCPPCP (SEQ ID NO:5)), a polypeptide that contains the "knob-bearing" CH2 and CH3 Domains (Fc Domain sequence, SEQ ID NO:15) and a C-terminus.

Thus, the first polypeptide chain of Control DART 1 is composed of: SEQ ID NO:41-SEQ ID NO:1-SEQ ID NO:29-SEQ ID NO:3-SEQ ID NO:10-SEQ ID NO:5-SEQ ID NO:15.

The amino acid sequence of the first polypeptide chain of Control DART 1 is (SEQ ID NO:43):

```
DVVMTQTPFSLPVSLGDQASISCRSSQSLVHSNGNTYLRWYLQKPGQSPK

VLIYKVSNRFSGVPDRFSGSGSGTDFTLKISRVEAEDLGVYFCSQSTHVP

WTFGGGTKLEIKGGGSGGGGEVQLVESGGGLVQPGGSLRLSCAASGFTFS

TYAMNWVRQAPGKGLEWVGRIRSKYNNYATYYADSVKGRFTISRDDSKNS

LYLQMNSLKTEDTAVYYCVRHGNFGNSYVSWFAYWGQGTLVTVSSASTKG

EVAACEKEVAALEKEVAALEKEVAALEKGGGDKTHTCPPCPAPEAAGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA
```

-continued

KGQPREPQVYTLPPSREEMTKNQVSLWCLVKGFYPSDIAVEWESNGQPEN

NYKTTPPVLDSDGSFFLYSKLTVDKSRWQQGNVFSCSVMHEALHNHYTQK

SLSLSPGK

The second polypeptide chain of Control DART 1 comprises, in the N-terminal to C-terminal direction, an N-terminus, a VL domain of a monoclonal antibody capable of binding to CD3 (VL$_{CD3}$) (SEQ ID NO:25), an intervening linker peptide (Linker 1; GGGSGGGG (SEQ ID NO:1)), a VH domain of a monoclonal antibody capable of binding to fluorescein (VH$_{Fluor}$) (SEQ ID NO:42), an intervening linker peptide (Linker 2; GGCGGG (SEQ ID NO:3)), a Heterodimer-Promoting (K-coil) Domain (KVAALKE-KVAALKE-KVAALKE-KVAALKE (SEQ ID NO:11) and a C-terminus.

Thus, the second polypeptide chain of Control DART 1 is composed of: SEQ ID NO:25-SEQ ID NO:1-SEQ ID NO:42-SEQ ID NO3-SEQ ID NO:11.

The amino acid sequence of the second polypeptide chain of Control DART 1 is (SEQ ID NO:44):

QAVVTQEPSLTVSPGGIVTLICRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGEVKLDETGGGLVQPGRPMKLSCVASGFTFSDY

WMNWVRQSPEKGLEWVAQIRNKPYNYETYYSDSVKGRFTISRDDSKSSVY

LQMNNLRVEDMGIYYCTGSYYGMDYWGQGTSVTVSSASTKGKVAACKEKV

AALKEKVAALKEKVAALKE

The third polypeptide chain of Control DART 1 comprises, in the N-terminal to C-terminal direction, an N-terminus, a peptide (Linker 3; DKTHTCPPCP (SEQ ID NO:4)), a polypeptide that contains the "hole-bearing" CH2 and CH3 Domains (Fc Domain sequence, SEQ ID NO:16) and a C-terminus.

Thus, the third polypeptide chain of Control DART 1 is composed of: SEQ ID NO:4-SEQ ID NO:16.

The amino acid sequence of the third polypeptide chain of Control DART 1 is SEQ ID NO:39):

DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLSCAVK

GFYPSDIAVEWESNGQPENNYKTTPPVLDSDGSFFLVSKLTVDKSRWQQG

NVFSCSVMHEALHNRYTQKSLSLSPGK

2. Control DART 2 (Fluorescein×CD19)

The first polypeptide chain of Control DART 2 comprises, in the N-terminal to C-terminal direction, an N-terminus, a VL domain of a monoclonal antibody capable of binding to CD19 (VL$_{CD19}$) (SEQ ID NO:17), an intervening linker peptide (Linker 1; GGGSGGGG (SEQ ID NO:1)), a VH domain of a monoclonal antibody capable of binding to fluorescein (VH$_{Fluor}$) (SEQ ID NO:42), an intervening linker peptide (Linker 2; GGCGGG (SEQ ID NO:3)), a Heterodimer-Promoting (E-coil) Domain (EVAALEK-EVAALEK-EVAALEK-EVAALEK (SEQ ID NO:10)), an intervening linker peptide (Spacer-Linker 3; GGGDKTH-TCPPCP (SEQ ID NO:5)), a polypeptide that contains the "knob-bearing" CH2 and CH3 Domains (Fc Domain sequence, SEQ ID NO:15) and a C-terminus.

Thus, the first polypeptide chain of Control DART 2 is composed of: SEQ ID NO:17-SEQ ID NO:1-SEQ ID NO:42-SEQ ID NO:3-SEQ ID NO:10-SEQ ID NO:5-SEQ ID NO:15.

The amino acid sequence of the first polypeptide chain of Control DART 2 is (SEQ ID NO:45):

ENVLTQSPATLSVTPGEKATITCRASQSVSYMHWYQQKPGQAPRLLIYDA

SNRASGVPSRFSGSGSGTDHTLTISSLEAEDAATYYCFQGSVYPFTFGQG

TKLEIKGGGSGGGGEVKLDETGGGLVQPGRPMKLSCVASGFTFSDYWMNW

VRQSPEKGLEWVAQIRNKPYNYETYYSDSVKGRFTISRDDSKSSVYLQMN

NLRVEDMGIYYCTGSYYGMDYWGQGTSVTVSSASTKGEVAACEKEVAALE

KEVAALEKEVAALEKGGGDKTHTCPPCPAPEAAGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSREEMTKNQVSLWCLVKGFYPSDIAVEWESNGQPENNYKTTPPVLDSDG

SFFLYSKLTVDKSRWQQGNVFSCSVMHEALHNHYTQKSLSLSPGK

The second polypeptide chain of Control DART 2 comprises, in the N-terminal to C-terminal direction, an N-terminus, a VL domain of a monoclonal antibody capable of binding to fluorescein (VL$_{Fluor}$) (SEQ ID NO:41), an intervening linker peptide (Linker 1; GGGSGGGG (SEQ ID NO:1)), a VH domain of a monoclonal antibody capable of binding to CD3 (VH$_{CD3}$) (SEQ ID NO:29), an intervening linker peptide (Linker 2; GGCGGG (SEQ ID NO:3)), a Heterodimer-Promoting (K-coil) Domain (KVAALKE-KVAALKE-KVAALKE-KVAALKE (SEQ ID NO:11) and a C-terminus.

Thus, the second polypeptide chain of Control DART 2 is composed of: SEQ ID NO:41-SEQ ID NO:1-SEQ ID NO:29-SEQ ID NO:3-SEQ ID NO:11.

The amino acid sequence of the second polypeptide chain of Control DART 2 is (SEQ ID NO:46):

QAVVTQEPSLTVSPGGTVTLTCRSSTGAVTTSNYANWVQQKPGQAPRGLI

GGTNKRAPWTPARFSGSLLGGKAALTITGAQAEDEADYYCALWYSNLWVF

GGGTKLTVLGGGGSGGGGEVKLDETGGGLVQPGRPMKLSCVASGFTFSDY

WMNWVRQSPEKGLEWVAQIRNKPYNYETYYSDSVKGRFTISRDDSKSSVY

LQMNNLRVEDMGIYYCTGSYYGMDYWGQGTSVTVSSASTKGKVAACKEKV

AALKEKVAALKEKVAALKE

The third polypeptide chain of Control DART 2 comprises, in the N-terminal to C-terminal direction, an N-terminus, a peptide (Linker 3; DKTHTCPPCP (SEQ ID NO:4)), a polypeptide that contains the "hole-bearing" CH2 and CH3 Domains (Fc Domain sequence, SEQ ID NO:16) and a C-terminus.

Thus, the third polypeptide chain of Control DART 2 is composed of: SEQ ID NO:4-SEQ ID NO:16.

The amino acid sequence of the third polypeptide of Control DART 2 is SEQ ID NO:39):

DKTHTCPPCPAPEAAGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLSCAVK

GFYPSDIAVEWESNGQPENNYKTTPPVLDSDGSFFLVSKLTVDKSRWQQG

NVFSCSVMHEALHNRYTQKSLSLSPGK

E. Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of the CD19×CD3 bi-specific monovalent diabodies of the present invention, or a combination of such agents and a pharmaceutically acceptable carrier. Preferably, compositions of the invention comprise a prophylactically or therapeutically effective amount of the CD19×CD3 bi-specific monovalent diabody of the invention and a pharmaceutically acceptable carrier.

The invention also encompasses pharmaceutical compositions comprising a CD19×CD3 bi-specific monovalent diabody of the invention (and particularly, a CD19×CD3 bi-specific monovalent Fc diabody), and a second therapeutic antibody (e.g., tumor specific monoclonal antibody) that is specific for a particular cancer antigen, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with a CD19×CD3 bi-specific monovalent diabody of the present invention (and particularly, a CD19×CD3 bi-specific monovalent Fc diabody) alone or with such pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. A kit can comprise CD19×CD3 bi-specific monovalent diabodies, and more preferably, a CD19×CD3 bi-specific monovalent Fc diabody, of the invention. The kit can further comprise one or more other prophylactic and/or therapeutic agents useful for the treatment of cancer, in one or more containers; and/or the kit can further comprise one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

F. Methods of Administration

The compositions of the present invention may be provided for the treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, such compositions are substantially purified (i.e., substantially free from substances that limit its effect or produce undesired side effects). In a specific embodiment, the subject is an animal, preferably a mammal such as non-primate (e.g., bovine, equine, feline, canine, rodent, etc.) or a primate (e.g., monkey such as, a cynomolgus monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "*Receptor-Mediated In Vitro Gene Transformation By A Soluble DNA Carrier System,*" J. Biol. Chem. 262: 4429-4432), construction of a nucleic acid as part of a retroviral or other vector, etc.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the CD19×CD3 bi-specific monovalent diabodies or CD19×CD3 bi-specific monovalent Fc diabodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the CD19×CD3 bi-specific monovalent diabodies (and particularly, the CD19×CD3 bi-specific monovalent Fc diabody) of the invention are packaged in a hermetically sealed container such as an ampoule or sachette indicating the quantity of the molecule. In one embodiment, the CD19×CD3 bi-specific monovalent diabodies of the invention are supplied as a dry sterilized lyophilized powder or water free concentrate in a hermetically sealed container and can be reconstituted, e.g., with water or saline to the appropriate concentration for administration to a subject. Preferably, the CD19×CD3 bi-specific monovalent diabodies of the invention are supplied as a dry sterile lyophilized powder in a hermetically sealed container at a unit dosage of at least 5 µg, more preferably at least µg, at least 15 µg, at least 25 µg, at least 50 µg, at least 100 µg, or at least 200 µg.

The lyophilized CD19×CD3 bi-specific monovalent diabodies or CD19×CD3 bi-specific monovalent Fc diabodies of the present invention should be stored at between 2 and 8° C. in their original container and the molecules should be administered within 12 hours, preferably within 6 hours, within 5 hours, within 3 hours, or within 1 hour after being reconstituted. In an alternative embodiment, CD19×CD3 bi-specific monovalent diabodies of the invention are supplied in liquid form in a hermetically sealed container indicating the quantity and concentration of the molecule, fusion protein, or conjugated molecule. Preferably, the liquid form of the CD19×CD3 bi-specific monovalent diabodies of the invention are supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For CD19×CD3 bi-specific monovalent diabodies, or CD19×CD3 bi-specific monovalent Fc diabodies, encompassed by the invention, the dosage administered to a patient is preferably determined based upon the body weight (kg) of the recipient subject. The dosage administered is typically from at least about 0.3 ng/kg per day to about 0.9 ng/kg per day, from at least about 1 ng/kg per day to about 3 ng/kg per day, from at least about 3 ng/kg per day to about 9 ng/kg per day, from at least about 10 ng/kg per day to about 30 ng/kg per day, from at least about 30 ng/kg per day to about 90 ng/kg per day, from at least about 100 ng/kg per day to about 300 ng/kg per day, from at least about 200 ng/kg per day to about 600 ng/kg per day, from at least about 300 ng/kg per day to about 900 ng/kg per day, from at least about 400 ng/kg per day to about 800 ng/kg per day, from at least about 500 ng/kg per day to about 1000 ng/kg per day, from at least about 600 ng/kg per day to about 1000 ng/kg per day, from at least about 700 ng/kg per day to about 1000 ng/kg per day, from at least about 800 ng/kg per day to about 1000 ng/kg per day, from at least about 900 ng/kg per day to about 1000 ng/kg per day, or at least about 1,000 ng/kg per day.

In another embodiment, the patient is administered a treatment regimen comprising one or more doses of such prophylactically or therapeutically effective amount of the CD19×CD3 bi-specific monovalent diabodies (and particularly, the CD19×CD3 bi-specific monovalent Fc diabodies) encompassed by the invention, wherein the treatment regimen is administered over 2 days, 3 days, 4 days, 5 days, 6 days or 7 days. In certain embodiments, the treatment regimen comprises intermittently administering doses of the prophylactically or therapeutically effective amount of the CD19×CD3 bi-specific monovalent diabodies encompassed by the invention (for example, administering a dose on day 1, day 2, day 3 and day 4 of a given week and not administering doses of the prophylactically or therapeutically effective amount of the CD19×CD3 bi-specific monovalent diabodies (and particularly, a CD19×CD3 bi-specific monovalent Fc diabodies) encompassed by the invention on day 5, day 6 and day 7 of the same week). Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the CD19×CD3 bi-specific monovalent diabodies (and particularly, the CD19×CD3 bi-specific monovalent Fc diabodies) encompassed by the invention is achieved.

Table 2 provides 5 examples of different dosing regimens described above for a typical course of treatment.

TABLE 2

| Regimen | Day | Diabody Dosage (ng diabody per kg subject weight per day) | | | | |
| --- | --- | --- | --- | --- | --- | --- |
| 1 | 1, 2, 3, 4 | 100 | 100 | 100 | 100 | 100 |
|   | 5, 6, 7 | none | none | none | none | none |
| 2 | 1, 2, 3, 4 | 300 | 500 | 700 | 900 | 1,000 |
|   | 5, 6, 7 | none | none | none | none | none |
| 3 | 1, 2, 3, 4 | 300 | 500 | 700 | 900 | 1,000 |
|   | 5, 6, 7 | none | none | none | none | none |
| 4 | 1, 2, 3, 4 | 300 | 500 | 700 | 900 | 1,000 |
|   | 5, 6, 7 | none | none | none | none | none |

The dosage and frequency of administration of the CD19×CD3 bi-specific monovalent diabodies or CD19×CD3 bi-specific monovalent Fc diabodies of the present invention may be reduced or altered by enhancing uptake and tissue penetration of the CD19×CD3 bi-specific monovalent diabodies by modifications such as, for example, lipidation.

The dosage of the CD19×CD3 bi-specific monovalent diabodies or CD19×CD3 bi-specific monovalent Fc diabodies of the invention administered to a patient may be calculated for use as a single agent therapy. Alternatively, the CD19×CD3 bi-specific monovalent diabodies or CD19× CD3 bi-specific monovalent Fc diabodies of the invention are used in combination with other therapeutic compositions and the dosage administered to a patient are lower than when said molecules are used as a single agent therapy.

The pharmaceutical compositions of the invention may be administered locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

The compositions of the invention can be delivered in a vesicle, in particular a liposome (See Langer (1990) "*New Methods Of Drug Delivery,*" Science 249:1527-1533); Treat et al., in LIPOSOMES IN THE THERAPY OF INFECTIOUS DISEASE AND CANCER, Lopez-Berestein and Fidler (eds.), Liss, New York, pp. 353-365 (1989); Lopez-Berestein, ibid., pp. 3 17-327).

The compositions of the invention can be delivered in a controlled-release or sustained-release system. Any technique known to one of skill in the art can be used to produce sustained-release formulations comprising one or more CD19×CD3 bi-specific monovalent diabodies of the invention. See, e.g., U.S. Pat. No. 4,526,938; PCT publication WO 91/05548; PCT publication WO 96/20698; Ning et al. (1996) "*Intratumoral Radioimmunotheraphy Of A Human Colon Cancer Xenograft Using A Sustained-Release Gel,*" Radiotherapy & Oncology 39:179-189, Song et al. (1995) "*Antibody Mediated Lung Targeting Of Long-Circulating Emulsions,*" PDA Journal of Pharmaceutical Science & Technology 50:372-397; Cleek et al. (1997) "*Biodegradable Polymeric Carriers For A bFGF Antibody For Cardiovascular Application,*" Pro. Int'l. Symp. Control. Rel. Bioact. Mater. 24:853-854; and Lam et al. (1997) "*Microencapsulation Of Recombinant Humanized Monoclonal Antibody For Local Delivery,*" Proc. Int'l. Symp. Control Rel. Bioact. Mater. 24:759-760, each of which is incorporated herein by reference in its entirety. In one embodiment, a pump may be used in a controlled-release system (See Langer, supra; Sefton, (1987) "*Implantable Pumps,*" CRC Crit. Rev. Biomed. Eng. 14:201-240; Buchwald et al. (1980) "*Long-Term, Continuous Intravenous Heparin Administration By An Implantable Infusion Pump In Ambulatory Patients With Recurrent Venous Thrombosis,*" Surgery 88:507-516; and Saudek et al. (1989) "*A Preliminary Trial Of The Programmable Implantable Medication System For Insulin Delivery,*" N. Engl. J. Med. 321:574-579). In another embodiment, polymeric materials can be used to achieve controlled-release of the molecules (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "*Inhibition Of Calcification Of Bioprosthetic Heart Valves By Local Controlled-Release Diphosphonate,*" Science 228: 190-192; During et al. (1989) "*Controlled Release Of Dopamine From A Polymeric Brain Implant: In Vivo Characterization,*" Ann. Neurol. 25:351-356; Howard et al. (1989) "*Intracerebral Drug Delivery In Rats With Lesion-Induced Memory Deficits,*" J. Neurosurg. 7(1):105-112); U.S. Pat. Nos. 5,679,377; 5,916,597; 5,912,015; 5,989,463; 5,128, 326; PCT Publication No. WO 99/15154; and PCT Publication No. WO 99/20253). Examples of polymers used in sustained-release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. A controlled-release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). Polymeric compositions useful as controlled-release implants can be used according to Dunn et al. (See U.S. Pat. No. 5,945,155). This particular method is based upon the therapeutic effect of the in situ controlled-release of the bioactive material from the polymer system. The implantation can generally occur anywhere within the body of the patient in need of therapeutic treatment. A non-polymeric sustained delivery system can be used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled-release systems are discussed in the review by Langer (1990, "*New Methods Of Drug Delivery,*" Science 249:1527-1533). Any technique known to one of skill in the art can be used to produce sustained-release formulations comprising one or more therapeutic agents of the invention. See, e.g., U.S. Pat. No. 4,526,938; International Publication Nos. WO 91/05548 and WO 96/20698; Ning et al. (1996) "*Intratumoral Radioimmunotheraphy Of A Human Colon Cancer Xenograft Using A Sustained-Release Gel,*" Radiotherapy & Oncology 39:179-189, Song et al. (1995) "*Antibody Mediated Lung Targeting Of Long-Circulating Emulsions,*" PDA Journal of Pharmaceutical Science & Technology 50:372-397; Cleek et al. (1997) "*Biodegradable Polymeric Carriers For A bFGF Antibody For Cardiovascular Application,*" Pro. Int'l. Symp. Control. Rel. Bioact. Mater. 24:853-854; and Lam et al. (1997) "*Microencapsulation Of Recombinant Humanized Monoclonal Antibody For Local Delivery,*" Proc. Int'l. Symp. Control Rel. Bioact. Mater. 24:759-760, each of which is incorporated herein by reference in its entirety.

Where the composition of the invention is a nucleic acid encoding a CD19×CD3 bi-specific monovalent diabody of the invention, the nucleic acid can be administered in vivo to promote expression of its encoded CD19×CD3 bi-specific monovalent diabody or CD19×CD3 bi-specific monovalent Fc diabody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al. (1991) "*Antennapedia Homeobox Peptide Regulates Neural Morphogenesis,*" Proc. Natl. Acad. Sci. (U.S.A.) 88:1864-1868), etc. Alternatively, a nucleic acid can be introduced intracellularly and incorporated within host cell DNA for expression by homologous recombination.

Treatment of a subject with a therapeutically or prophylactically effective amount of a CD19×CD3 bi-specific monovalent diabody (and particularly, a CD19×CD3 bi-specific monovalent Fc diabody) of the invention can include a single treatment or, preferably, can include a series of treatments. In a preferred example, a subject is treated with such a diabody one time per week for between about 1 to 10 weeks, preferably between 2 to 8 weeks, more preferably between about 3 to 7 weeks, and even more preferably for about 4, 5, or 6 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

G. Uses of the Compositions of the Invention

The CD19×CD3 bi-specific monovalent diabodies of the present invention (and particularly, the CD19×CD3 bi-specific monovalent Fc diabodies of the present invention) have the ability to treat any disease or condition associated with or characterized by the expression of CD19. Thus, without limitation, such molecules may be employed in the diagnosis or treatment of acute myeloid leukemia (AML), chronic myelogenous leukemia (CML), including blastic crisis of CML and Abelson oncogene associated with CML (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), including Richter's syndrome or Richter's transformation of CLL, hairy cell leukemia (HCL), blastic plasmacytoid dendritic cell neoplasm (BPDCN), non-Hodgkin lymphomas (NHL), including mantel cell leukemia (MCL), and small lymphocytic lymphoma (SLL), Hodgkin's lymphoma, systemic mastocytosis, and Burkitt's lymphoma; Autoimmune Lupus (SLE), allergy, asthma and rheumatoid arthritis. The bi-specific monovalent diabodies of the present invention may additionally be used in the manufacture of medicaments for the treatment of the above-described conditions.

EXAMPLES

Having now generally described the invention, the same will be more readily understood through reference to the following examples, which are provided by way of illustration and are not intended to be limiting of the present invention unless specified.

Example 1

Quantitation of CD19 Cell Surface Expression

To identify suitable target cell lines for evaluating the biological activity of CD19×CD3 bispecific diabodies, CD19 cell surface expression levels were first confirmed using quantitative FACS (QFACS) on a panel of human B-cell lymphoma/leukemia cell lines, including Nalm-6 (acute lymphoblastic leukemia), Raji (Burkitt's lymphoma), Daudi (Burkitt's lymphoma), HBL-2 (mantle cell lymphoma), MEC-1 (chronic lymphocytic leukemia), and Jeko-1 (mantle cell lymphoma), MOLM-13 (acute myeloid leukemia cell line), JIMT1 (breast cancer) and Colo205 (colon cancer). Absolute numbers of CD19 antibody binding sites on the surface were calculated using a QFACS kit. As shown in Table 3, the absolute numbers of CD19 binding sites on the cell lines were in the order of Raji (high) >Nalm-6 (medium)>Daudi (medium)>HBL2 (medium) >MEC-1 (low)>Jeko-1 (low). As expected MOLM-3, JIMT-1 and Colo205 lacked CD19 expression, which is consistent with CD19 being a B-cell specific antigen.

TABLE 3

| Target Cell Line | CD19 Surface Expression (Antibody Binding Sites) |
|---|---|
| Raji | 670,322 |
| Nalm-6 | 442,730 |
| Daudi | 369,860 |
| HBL-2 | 334,725 |
| MEC-1 | 177,025 |
| Jeko-1 | 124,396 |

Example 2

Binding Affinities

In order to quantitate the extent of binding between a CD19×CD3 bi-specific monovalent diabody and human or cynomolgus monkey CD3, BIACORE® (SPR technology for analyzing and characterizing molecular interactions in terms of binding and kinetics) analyses were conducted using the illustrative CD19×CD3 bi-specific monovalent Fc diabody, DART-A. BIACORE® analyses measure the dissociation off-rate, kd. The binding affinity (KD) between an antibody and its target is a function of the kinetic constants for association (on rate, $k_a$) and dissociation (off-rate, kd) according to the formula: KD=[kd]/[ka]. The BIACORE® analysis uses surface plasmon resonance to directly measure these kinetic parameters.

The results of binding of DART-A (0-100 nM) to soluble human and cynomolgus monkey CD3 and CD19, analyzed by BIACORE® SPR technology, are shown in Table 4.

The binding affinity of DART-A is similar for human and cynomolgus monkey CD3 (KD=21.2 nM and 21.9 nM, respectively). However, DART-A has an approximate 10 fold lower affinity for cynomolgus monkey CD19 than for human CD19 (KD=20.3 nM and 2.0 nM, respectively) due to an increased dissociation rate constant (kd) from cynomolgus monkey CD19. The cynomolgus monkey remains a relevant species for toxicology evaluations, although the difference in CD19 binding affinity should be considered.

TABLE 4

| Antigens | ka (± SD) (M-1s-1) | kd (± SD) (s-1) | KD (± SD) (nM) |
|---|---|---|---|
| Human CD3ε/δ | $2.2 \times 10^5$ | $4.5 (\pm 0.1) \times 10^{-3}$ | 21.2 (± 1.7) |
| Cynomolgus CD3ε/δ | $2.0 (\pm 0.1) \times 10^5$ | $4.3 (\pm 0.2) \times 10^{-3}$ | 21.9 (± 1.2) |
| Human CD19-His | $2.8 (\pm 0.3) \times 10^5$ | $5.6 (\pm 0.6) \times 10^{-4}$ | 2.0 (± 0.2) |
| Cynomolgus CD19-His | $2.4 (\pm 0.1) \times 10^5$ | $4.7 (\pm 1.1) \times 10^{-3}$ | 20.3 (± 1.3) |

Example 3

Cell Binding Characteristics

DART-A binding to mouse, rat, rabbit, cynomolgus monkey, and human blood leukocytes (purified from whole blood) was evaluated in vitro by flow cytometry. Leukocytes were stained with DART-A, as well as Control DART 1 and Control DART 2, at concentrations of 25 or 100 nM for approximately 1 hour. Control DART 2 contains the same CD19 binding component as DART-A, while Control DART 1 contains the same CD3 binding component as DART-A. Following incubation, DART proteins bound to leukocytes were detected with an anti-E-coil/K-coil (EK) mAb, which recognizes the EK coil heterodimerization region of the DART proteins. No DART-A binding was observed on mouse, rat, or rabbit blood leukocytes. Likewise, neither Control DART diabody showed any binding to mouse, rat, or rabbit leukocytes. As expected, both concentrations of DART-A tested showed specific binding to both human and cynomolgus monkey blood leukocytes.

Figure 3:
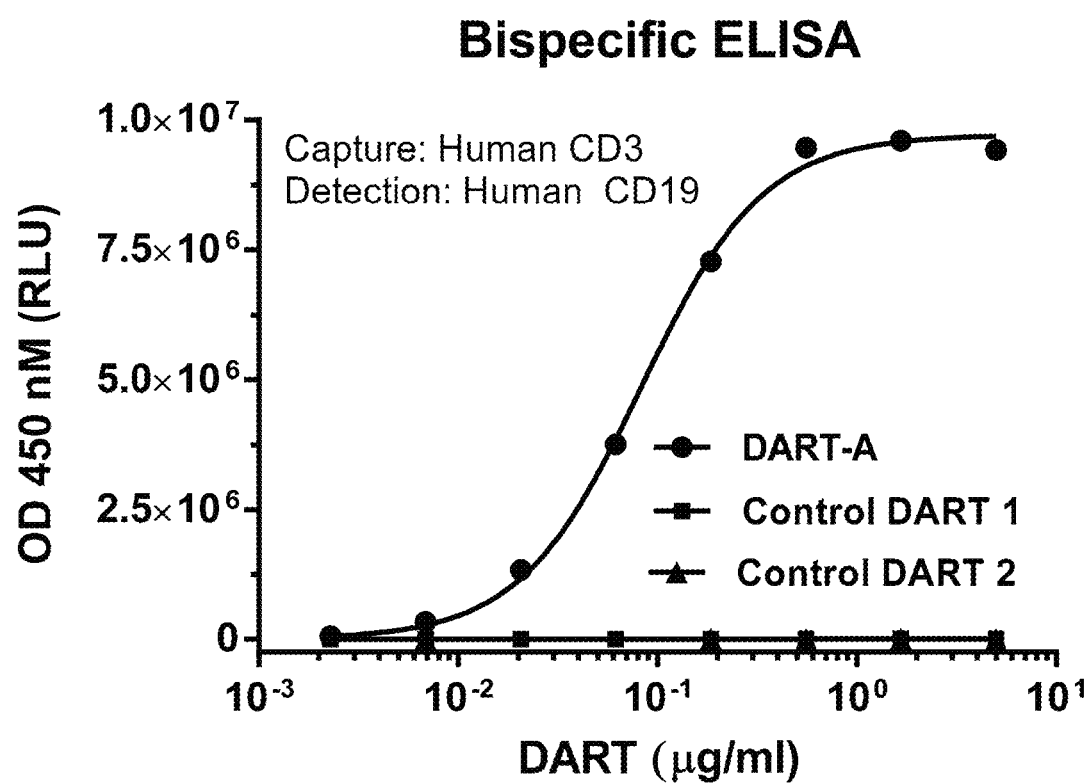
FIG. 3 shows the simultaneous engagement of both CD19 and CD3 by DART-A (•). Neither Control DART 1 (■) nor Control DART 2 (▲) were capable of binding to both targets simultaneously.
Figure 4A:
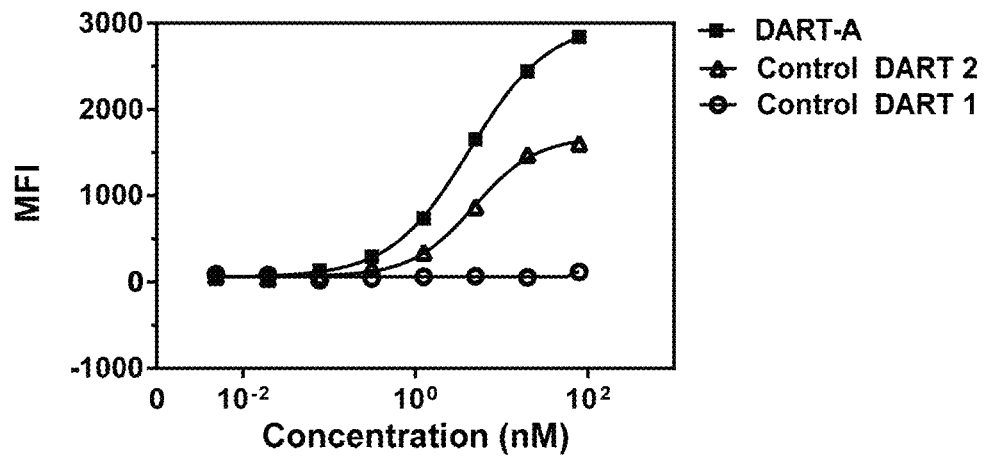
FIGS. 4A-4B show the binding of a CD19×CD3 bi-specific molecule (DART-A) to human (FIG. 4A) and cynomolgus monkey (FIG. 4B) CD20+ B cells.
Figure 4B:
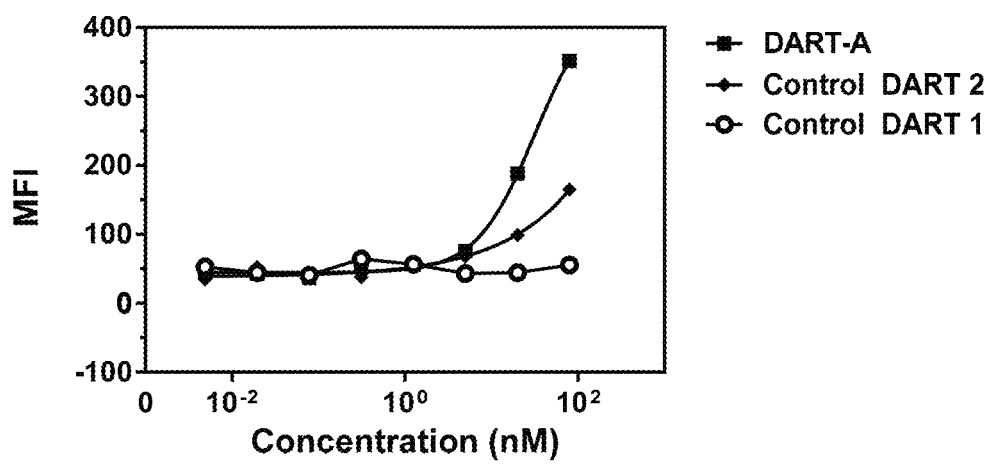
Figure 5A:
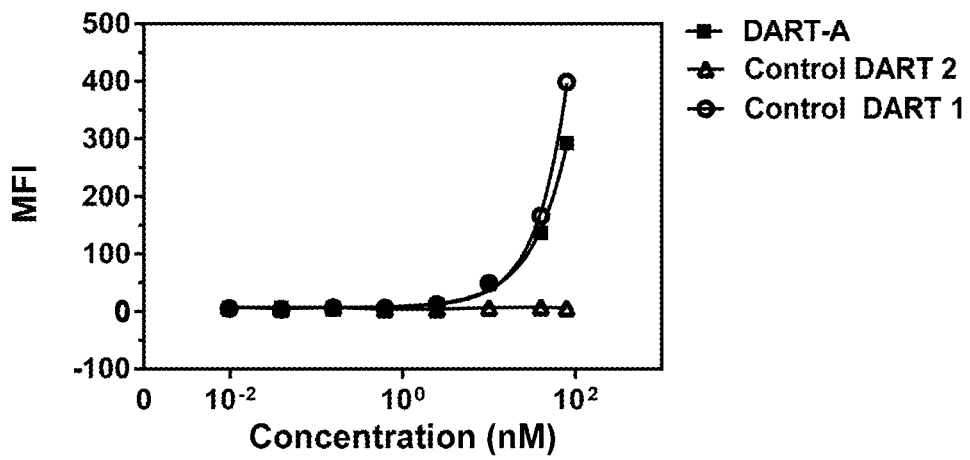
FIGS. 5A-5B show the binding of the CD19×CD3 bi-specific molecule (DART-A) to human (FIG. 5A) and cynomolgus monkey (FIG. 5B) CD4+ and CD8+ T cells.
Figure 5B:
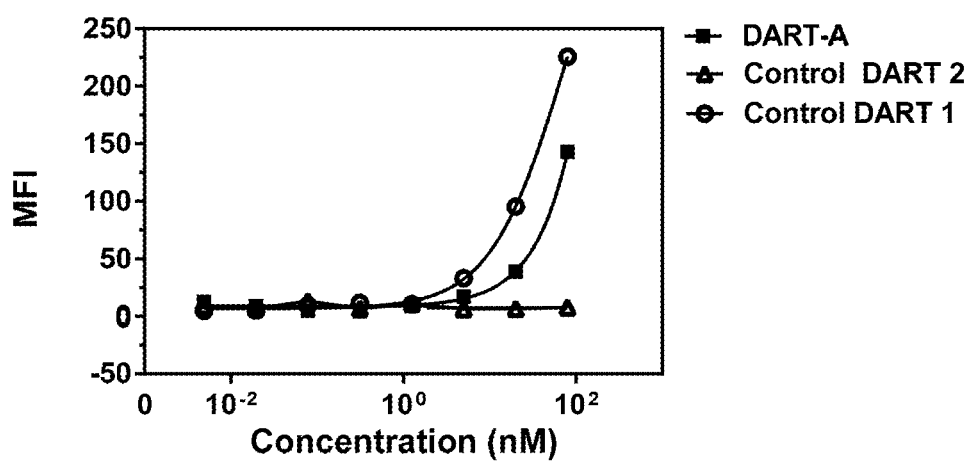

A bifunctional ELISA assay was used to demonstrate simultaneous engagement of both target antigens by DART-A. ELISA plates were coated with soluble human CD3ε/δ heterodimer and incubated at 4 C overnight and then blocked with BSA. Various concentrations of DART-A were added followed by addition of soluble human CD19-biotin. The plates were washed and the immune complex was detected with chemoluminescent substrate conjugated to streptavidin. As shown in FIG. 3, DART-A is capable of simultaneous binding to both CD19 and CD3.

The bi-specific binding of DART-A was further evaluated in both cynomolgus monkey and human blood leukocytes (purified from whole blood) by flow cytometery. Leukocytes were stained with DART-A, Control DART 1 or Control DART 2 at concentrations ranging from 0.005 to 80 nM for approximately 1 hour. Following incubation, binding to leukocytes was detected using a biotinylated anti-E-coil/K-coil (EK) mAb, which recognizes the EK coil heterodimerization region of the DART proteins and streptavidin-PE. Since DART-A binds to CD3, a combination of CD4 and CD8 was used to define the T cell population. Similarly, CD20 was used as a B cell marker instead of CD19. Therefore, in this study, the CD4+ and CD8+ gated events represent the T cell population and CD20+ gated events represent the B cell population. DART-A demonstrated bi-specific binding to both human and cynomolgus monkey B cells and T cells. In contrast, the Control DART diabodies showed only mono-specific binding to B cells (Control DART 2) or T cells (Control DART 1) consistent with their corresponding binding specificity. The DART-A and control DART diabodies binding titration curves for human and cynomolgus monkey B and T cells are provided in FIGS. 4A-4B and FIGS. 5A-5B.

Example 4

DART-A-Mediated Redirected Killing of Target Tumor Cells Using Human T Cells

The ability of DART-A to mediate redirected target cell killing was evaluated on 3 target B lymphoma cell lines, Raji/GF (Burkitt's lymphoma), HBL-2 (mantle cell lymphoma), and Jeko-1 (mantle cell lymphoma), displaying a range of CD19 expression, using purified human primary T cells as effector cells. Raji/GF cells showed the highest levels of CD19 expression, followed by medium levels of CD19 expression in HBL-2 cells, and lower CD19 expression levels in Jeko-1 cells. Target tumor cell killing was measured using a lactate dehydrogenase (LDH) release assay in which the enzymatic activity of LDH released from cells upon cell death is quantitatively measured, or by a luciferase assay in which luciferase relative light unit (RLU) is the read-out to indicate relative viability of Raji/GF target cells, which are engineered to express both the green fluorescent protein (GFP) and luciferase reporter genes.

Figure 6A:
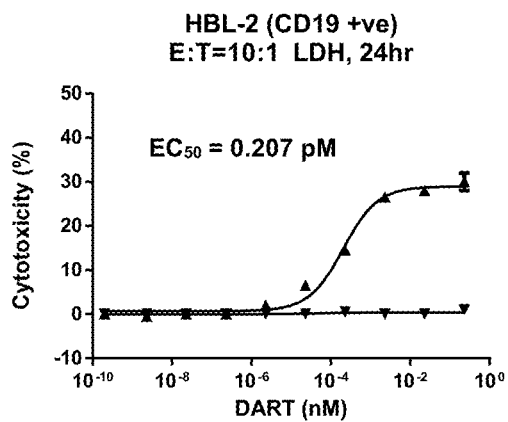
FIGS. 6A-6F show CD19×CD3 bi-specific molecule (DART-A)-mediated redirected killing of target cells relative to that of Control DART 1. Dose-response curves of DART-A-mediated cytotoxicity using primary human T cells as effector cells for target cell lines: HBL-2 (FIG. 6A), Raji/GF (green fluorescent) (FIG. 6B), Jeko-1 (FIG. 6C), Molm-13 (FIG. 6D), and Colo205/Luc (FIG. 6F) with target cell killing measured using the LDH assay.
Figure 6B:
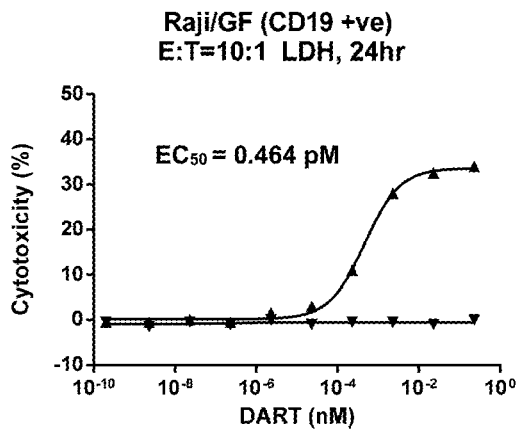
Figure 6C:
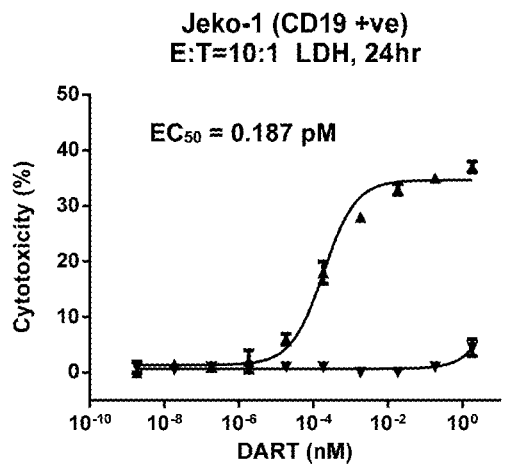
Figure 6D:
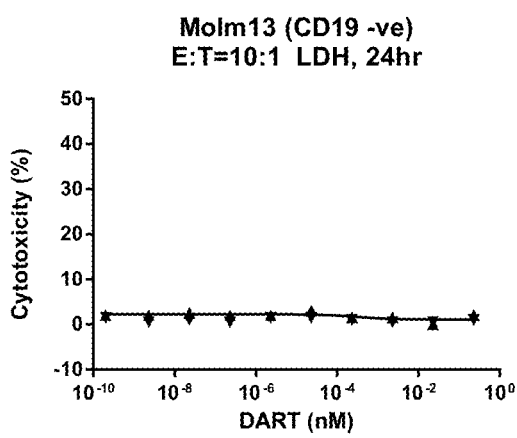
Figure 6E:
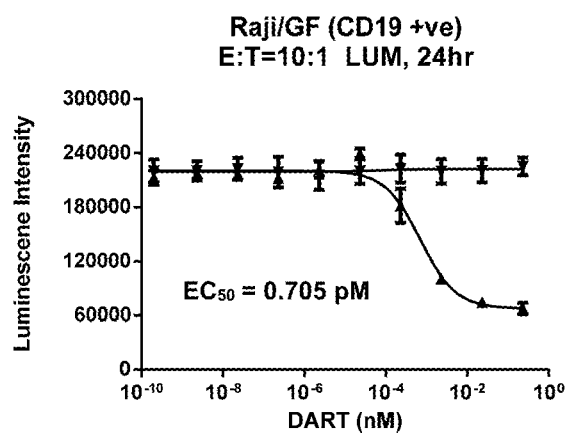
Figure 6F:
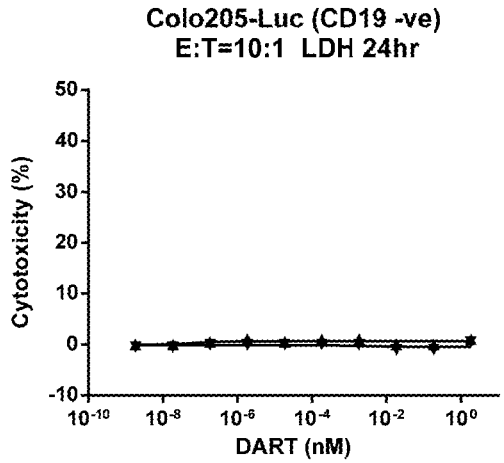
Figure 7A:
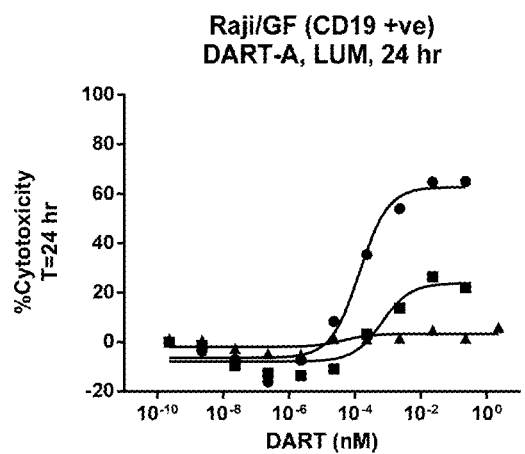
FIGS. 7A-7D show CD19×CD3 bi-specific molecule (DART-A)-mediated redirected killing of target Raji/GF cells at varying E:T cell ratios (10:1 (•), 5:1 (■), and 2.5:1 (▲)). Dose-response curves of DART-A-mediated cytotoxicity (percent cytotoxicity) with primary human T cells as effector cells for CD19+ target Raji/GF cells determined after 24 hours incubation (FIG. 7A) and after 48 hours incubation (FIG. 7B). Dose-response curves of DART-A-mediated cytotoxicity (percent cytotoxicity) with primary human T cells as effector cells for CD19-negative JIMT-1 cells determined after 24 hours incubation (FIG. 7C) and after 48 hours incubation (FIG. 7D) were included as controls. Shown is 1 of 3 representative experiments, each of which used T cells from independent donors.
Figure 7C:
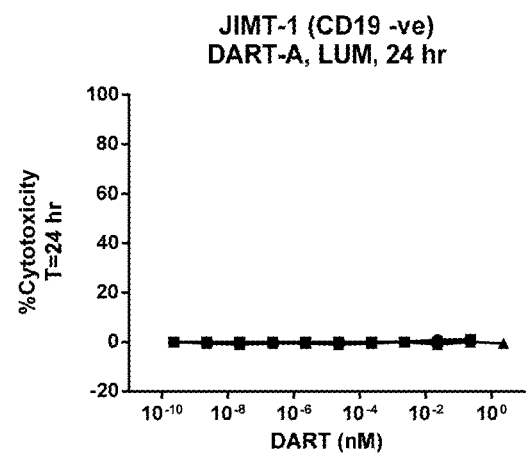
Figure 7B:
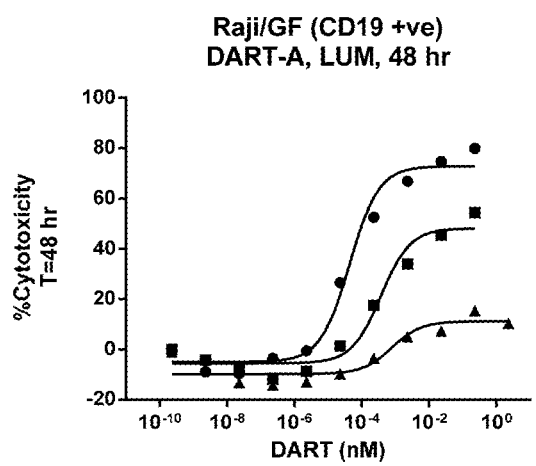
Figure 7D:
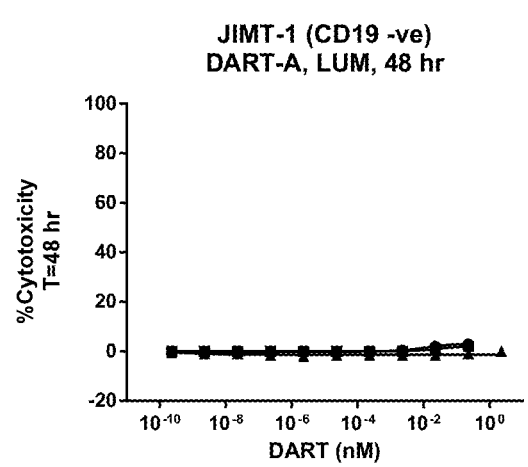
Figure 8A:
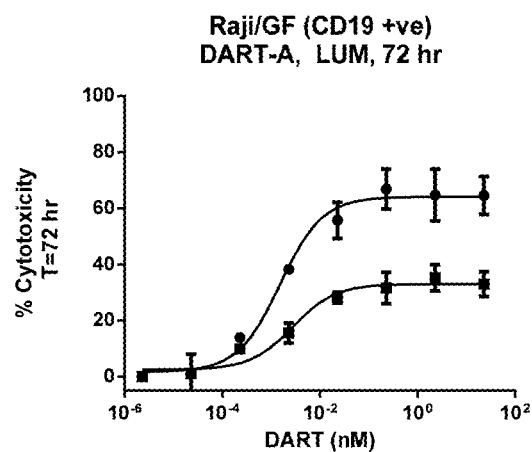
FIGS. 8A-8D show CD19×CD3 bi-specific molecule (DART-A)-mediated redirected killing of target Raji/GF Cells at lower E:T cell ratios of 2.5:1 (•) or 1:1 (■). Dose-response curves of DART-A-mediated cytotoxicity (percent cytotoxicity) with primary human T cells as effector cells for CD19+ target Raji/GF cells determined after 72 hours incubation (FIG. 8A) and after 96 hours incubation (FIG. 8B). Dose-response curves of CD19×CD3 bi-specific DART-A-mediated cytotoxicity (percent cytotoxicity) with primary human T cells as effector cells for CD19-negative JIMT-1 cells determined after 72 hours incubation (FIG. 8C) and after 96 hours incubation (FIG. 8D) were included as controls. Shown is 1 of 3 representative experiments, each of which used T cells from independent donors.
Figure 8C:
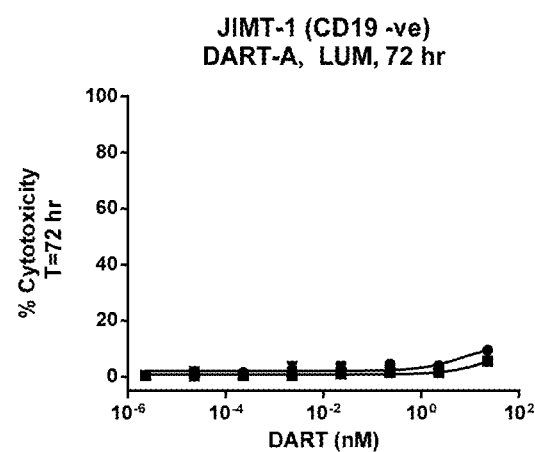
Figure 8B:
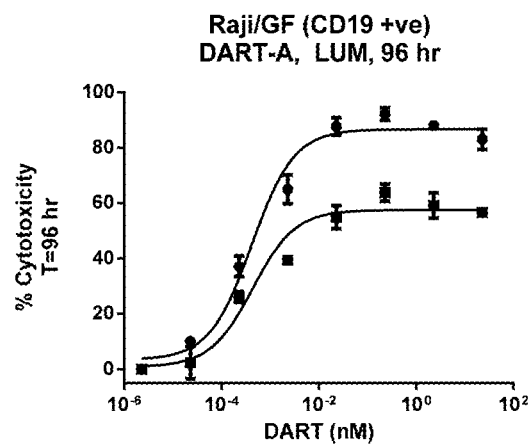
Figure 8D:
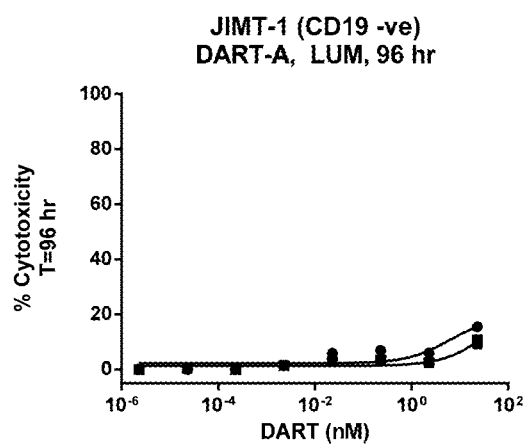

DART-A exhibited potent redirected cell killing in all 3 cell lines when purified T cells from multiple independent human donors were used at an effector to target (E:T) cell ratio of 10:1 (FIGS. 6A-6C). The average effective concentration at 50% of maximal activity (EC50) values were $1.05 \times 10^{-1}$ pM for HBL-2 cells; $3.07 \times 10^{-1}$ pM for Raji/GF cells; and $1.46 \times 10^{-1}$ pM for Jeko-1 cells (Table 5). Control DART 1 did not mediate T cell redirected killing of target cells. Most importantly, no cell killing activity was observed in cell lines (Molm-13 and Colo205) that do not express CD19 (FIGS. 6D-6F).

TABLE 5

Summary of EC50 Values from Representative DART-A-Mediated Redirected Killing of Target Raji/GF Cells at Varying E:T Cell Ratios

| Cytotoxicity | E:T = 10:1 | | E:T = 5:1 | | E:T = 2.5:1 | |
| --- | --- | --- | --- | --- | --- | --- |
| | EC50 (pM) | Emax (%) | EC50 (pM) | Emax (%) | EC50 (pM) | Emax (%) |
| 24 hours | 0.14 | 63 | 0.67 | 24 | N/A | 4 |
| 48 hours | 0.0441 | 73 | 0.38 | 48 | 1.08 | 11 |

To evaluate the activity of DART-A in the presence of a lower number of effector cells, redirected cell killing was tested with lower E:T cell ratios of 5:1, 2.5:1, and 1:1 in Raji/GF cells following incubation with DART-A for 24 to 96 hours. Cytotoxic activity observed at the 5:1 ratio was about half the maximal activity observed at the 10:1 ratio; lower, specific activity was also observed with an E:T cell ratio of 2.5:1 at both the 24 and 48 hour time points (FIGS. 7A-7D and Table 5). Following incubation for 72 or 96 hours, cytotoxicity of Raji/GF cells was significantly increased at the 2.5:1 and 1:1 ratios (see FIGS. 8A-8D and Table 6). It is noteworthy that efficient cell lysis at lower E:T cell ratios increased in Raji/GF cells over time, suggesting serial target cell killing by DART-A-activated T cells. The kinetics suggest that time is the limiting factor for low T cell numbers to efficiently eliminate larger numbers of target cells. In conclusion, data from multiple experiments using human T cells from different donors indicate that DART-A redirected cell killing activity is dependent on both the E:T cell ratio and time, particularly at lower E:T cell ratios.

TABLE 6

Summary of EC50 Values from Representative DART-A-Mediated Redirected Killing of Target Raji/GF Cells at Lower E:T Cell Ratios

| Cytotoxicity | E:T = 2.5:1 | | E:T = 1:1 | |
| --- | --- | --- | --- | --- |
| | EC50 (pM) | Emax (%) | EC50 (pM) | Emax (%) |
| 72 hours | 1.54 | 64 | 2.79 | 33 |
| 96 hours | 0.422 | 87 | 0.440 | 56 |

Example 5

DART-A-Mediated Autologous B Cell Depletion in Human and Cynomolgus Monkey PBMCs Since normal B cells express CD19 and since DART-A was shown to cross-react with cynomolgus monkey CD19 and CD3 (Example 2, FIGS. 4A-4B and FIGS. 5A-5B), DART-A-mediated cytotoxicity was investigated in both human and cynomolgus monkey peripheral blood mononuclear cells (PBMCs). There was dose-dependent CD20+ B cell depletion observed in both human and cynomolgus monkey PBMCs after treatment with DART-A (FIGS. 9A-9B). As expected, no B cell depletion was observed after treatment with Control DART 1.

To further confirm DART-A activity in PBMCs, multiple independent human or cynomolgus monkey PBMC donors with varying T cell (effector) to B cell (target) E:T cell ratios were used to evaluate potency. In summary (Table 7), the EC50 values for human B cell depletion ranged from 1.84 to 6.27 pM; while the EC50 values for cynomolgus monkey B cell depletion were between 106.8 to 859.1 pM. The potency of DART-A for autologous human B cell depletion appeared greater than that for cynomolgus monkey B cell depletion (approximately 100-fold greater by average; range: 19 to 312-fold). However, it is noteworthy that the E:T cell ratio in cynomolgus monkey PBMCs (about 4:1 on average) was lower than that in human PBMCs (about 8:1 on average), which likely contributed to the greater difference in EC50 values given that DART-A redirected killing activity is dependent on the E:T cell ratio. Potential differences in CD19 expression levels between human and cynomolgus monkey B cells may be another variable factor contributing to the apparent difference in potency.

TABLE 7

Summary of EC50 Values for Autologous
B Cell Depletion Following Treatment
of Human or Cynomolgus Monkey PBMCs with DART-A

| | EC50 Values (pM) | | | EC50 Values (pM) | |
|---|---|---|---|---|---|
| | DART-A | Control DART | | DART-A | Control DART |
| Human 5 (E:T = 8:1) | 6.27 | No activity | Cyno 5 (E:T = 3:1) | 166.2 | No activity |
| Human 6 (E:T = 8:1) | 2.75 | No activity | Cyno 6 (E:T = 2:1) | 859.1 | No activity |
| Human 7 (E:T = 5:1) | 5.52 | No activity | Cyno 7 (E:T = 3:1) | 106.8 | No activity |
| Human 8 (E:T = 9:1) | 1.84 | No activity | Cyno 8 (E:T = 7:1) | 239.1 | No activity |
| Mean | 4.20 | Not applicable | Mean | 342.8 | Not applicable |

It is important to note that DART-A mediated efficient cytotoxicity against Raji/GF target cells when cynomolgus monkey PBMCs were used as effector cells with an EC50 of $1.30 \times 10^{-2}$ pM (FIG. 10) similar to that observed when human T cells were used as effector cells (average EC50=$3.07 \times 10^{-1}$ pM), indicating that human and cynomolgus monkey T cells have comparable activity against the same target cell line. These data further support the use of the cynomolgus monkey as a relevant species for the evaluation of DART-A in non-clinical toxicology studies.

Example 6

Evaluation of DART-A-Mediated Cytokine Release Using Human or Cynomolgus Monkey Effector Cells DART-A-mediated depletion of the B cell population in human and cynomolgus monkey PBMCs was associated with cytokine release in both human and cynomolgus monkey PBMCs. As summarized below in Table 8, the EC50 values for cytokine release are equivalent to or higher than for human or cynomolgus monkey autologous B cell depletion, indicating that DART-A is more potent in mediating B cell depletion than inducing cytokine release in vitro. The cytokine release profiles between human and cynomolgus monkeys in vitro have some similarities and differences. IFN-γ and TNF-α were the predominant cytokines released in both species following treatment with DART-A. However, IL-6 was the third most predominant cytokine produced in humans based on Emax values, while IL-2 was produced in substantial amounts only in cynomolgus monkey PBMCs. Comparison of the mean EC50 values for the most sensitive cytokines produced in PBMCs following incubation with DART-A (IFN-γ, TNF-α, and IL-6 in humans) with the mean EC50 values for autologous B cell depletion, revealed there is at least a 6-fold apparent safety margin as reflected in the difference between B cell depletion and cytokine production in humans (Table 9).

TABLE 8

Summary of EC50 Values for Autologous
B Cell Depletion and Cytokine
Production Following Treatment of Human or
Cynomolgus Monkey PBMCs with DART-A

| Human PBMCs | |
|---|---|
| Assay (number of donors tested) | Mean EC50 (pM) |
| Human B Cell Depletion (n = 4) | 4.20 |
| Human Cytokine Release (n = 2) | |
| IFN-γ | 25.21 |
| TNF-α | 31.83 |
| IL-10 | 70.11 |
| IL-6 | 23.55 |
| IL-4 | Not applicable* |
| IL-2 | 56.77 |
| Cynomolgus Monkey PBMCs | |
| Cynomolgus Monkey B Cell Depletion (n = 4) | 342.8 |
| Cynomolgus Monkey Cytokine Release (n = 2) | |
| IFN-γ | 925.24 |
| TNF-α | 262.22 |
| IL-6 | 306.68 |
| IL-5 | 486.22 |
| IL-4 | 1718.63 |
| IL-2 | 2930.19 |

*below limit of detection

TABLE 9

Summary of EC50 Values for Cytotoxicity vs Cytokine Production
Following in vitro Evaluation of DART-A in Human Cells

| CTL Assay[1] | | Human PBMCs[2] | |
|---|---|---|---|
| Assay (number of donors) Cytotoxicity | Mean EC50 (pM) | Assay (number of donors) Autologous B cell Depletion | Mean EC50 (pM) |
| HBL-2 (n = 5) | 0.11 | PBMCs (n = 7) | 4.20 |
| Raji/GF (n = 5) | 0.31 | | |
| Jeko-1 (n = 3) | 0.15 | | |
| Cytokine Release (n = 2) | | Cytokine Release (n = 2) | |
| IFN-γ | 5.51 | IFN-γ | 25.21 |
| TNF-α | 3.71 | TNF-α | 31.83 |
| IL-2 | 6.32 | IL-6 | 23.55 |
| EC50 fold difference (Indicative Safety Margin) | 12-58 | EC50 fold difference (Indicative Safety Margin) | 6-8 |

[1]Activity evaluated using CTL assay with CD19-expressing tumor cells (HBL-2, Raji/GF, or Jeko-1) in the presence of purified human T cells (E:T = 10:1). Cytokine release was evaluated using Raji/GF tumor cells.
[2]Activity evaluated in normal human PBMCs.

Figure 11A:
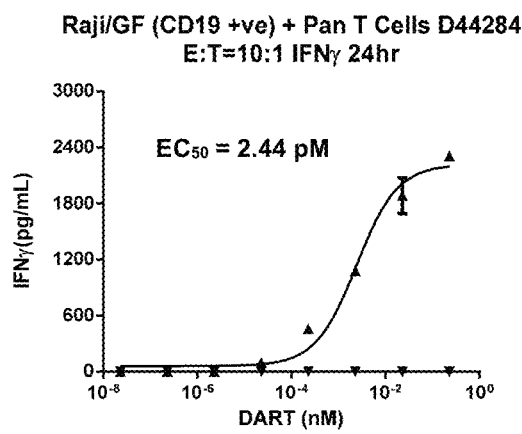
FIGS. 11A-11C show CD19×CD3 bi-specific molecule (DART-A)-mediated cytokine release from human T cells in the presence of target cells. Human T cells were treated with DART-A or Control DART 1 for about 24 hours in the presence of Raji/GF target cells. Culture supernatants were collected and subjected to ELISA-based cytokine measurement. Shown is one representative experiment of 2 using different donors.
Figure 11B:
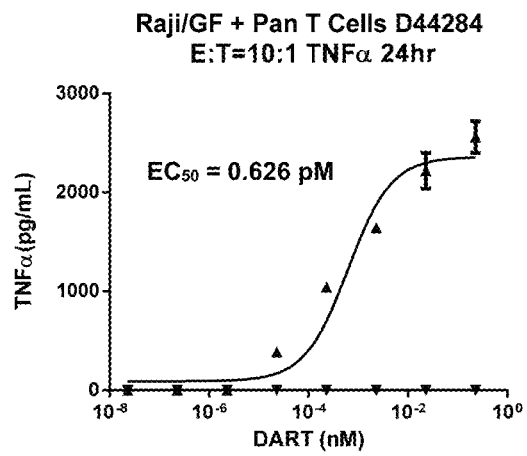
Figure 11C:
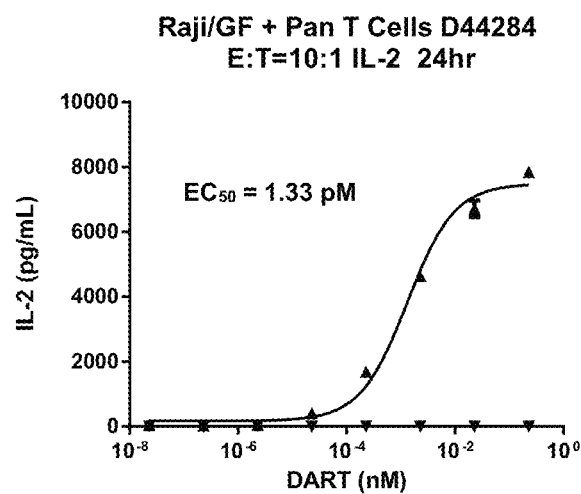
Figure 12A:
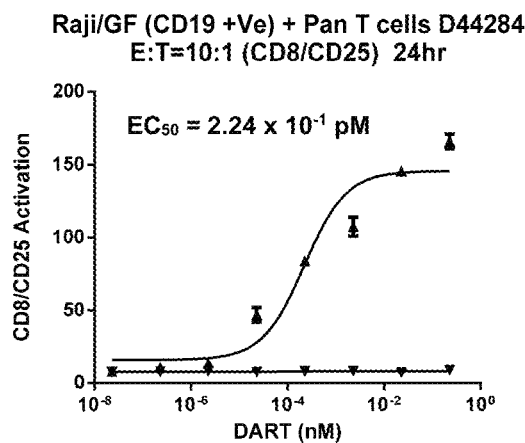
FIGS. 12A-12D show human T cell activation during redirected cell killing by a CD19×CD3 bi-specific molecule (DART-A) relative to that of Control DART 1. Dose-response of DART-A-mediated induction of T cell activation markers CD25 (FIGS. 12A-12B) and CD69 (FIGS. 12C-12D) on CD8+(FIGS. 12A and 12C) and CD4+(FIGS. 12B and 12D) human T cells using Raji/GF target cells. Shown is one representative experiment of 2, each of which used T cells from different donors. DART-A: ▲; Control DART 1: ▼.
Figure 12C:
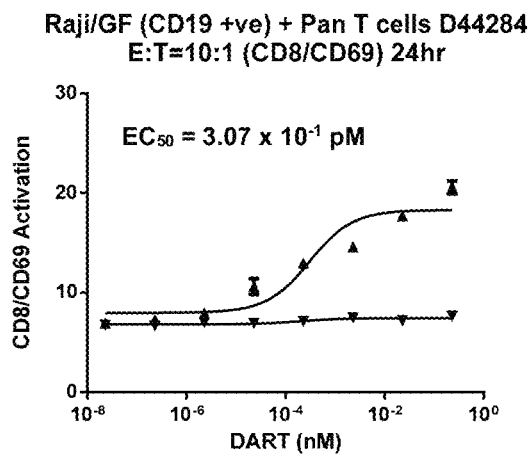
Figure 12B:
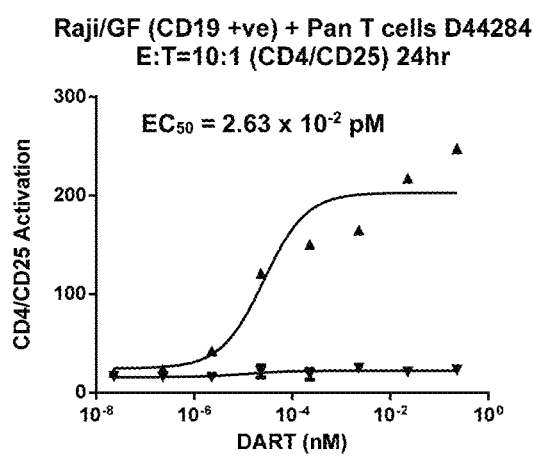
Figure 12D:
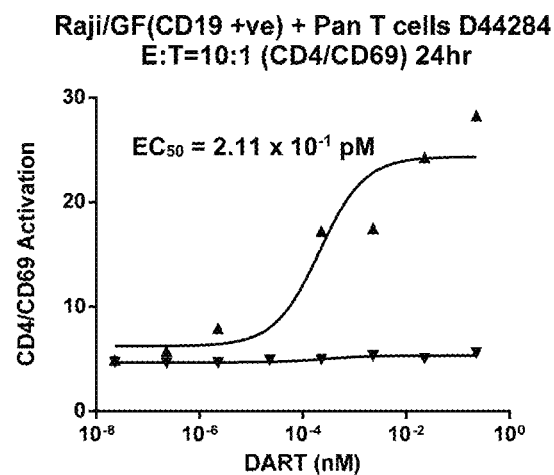
Figure 13A:
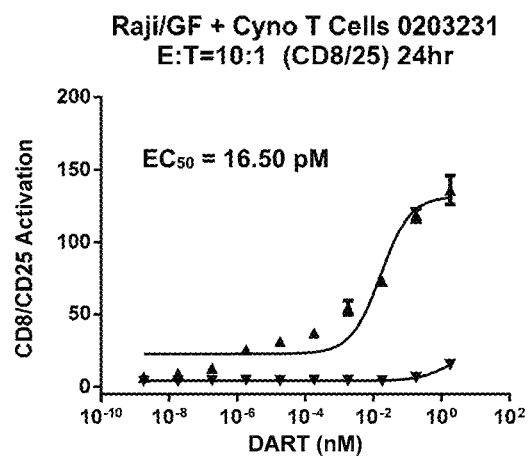
FIGS. 13A-13D show cynomolgus monkey T cell activation during redirected cell killing by a CD19×CD3 bi-specific molecule (DART-A) relative to that of Control DART 1. Dose-response of DART-A-mediated induction of T cell activation markers CD25 (FIGS. 13A and 13B) and CD69 (FIGS. 13C and 13D) on CD8+(FIGS. 13A and 13C) and CD4+(FIGS. 13B and 13D) cynomolgus monkey T cells or PBMCs using Raji/GF target cells. Shown is one representative experiment using T cells. DART-A: ▲; Control DART 1: ▼.
Figure 13C:
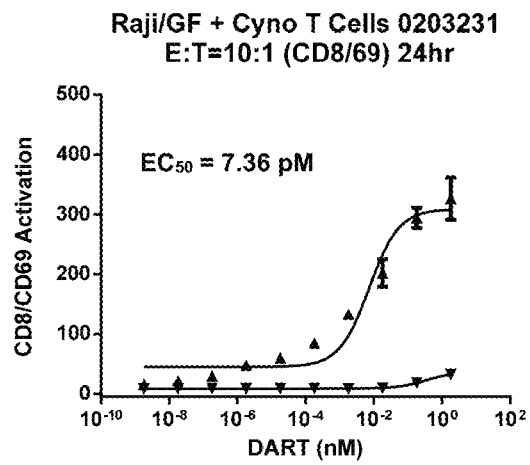
Figure 13B:
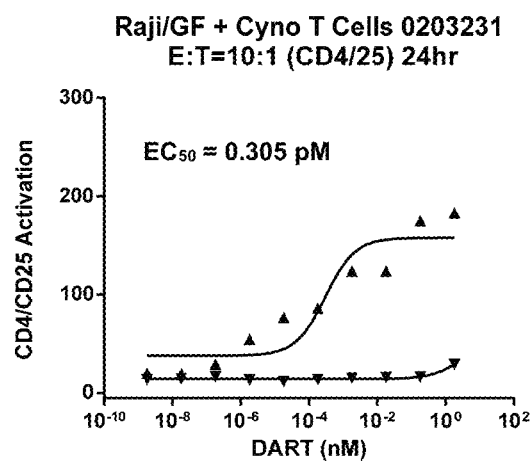
Figure 13D:
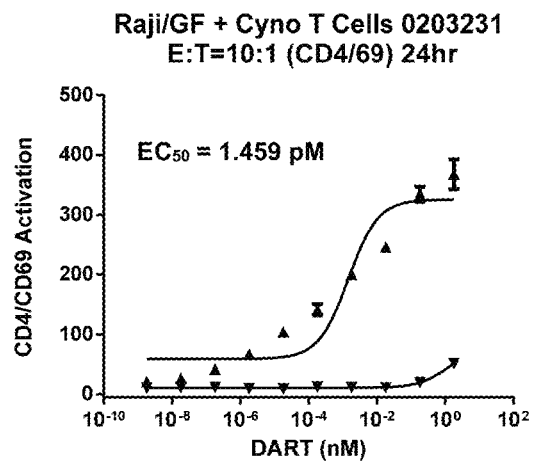
Figure 14A:
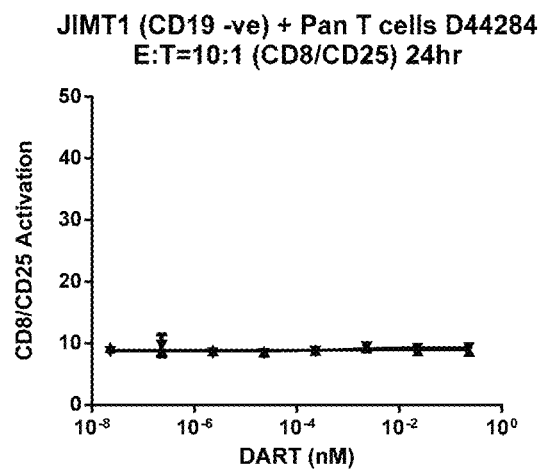
FIG. 14A-14D show that the CD19×CD3 bi-specific molecule (DART-A) and Control DART 1 fail to mediate human T cell activation in the presence of CD19-negative JIMT1 cells. Presented is a dose-response of DART-A-mediated induction of T cell activation markers CD25 (FIGS. 14A and 14B) and CD69 (FIGS. 14C and 14D) on CD8+(FIGS. 14A and 14C) and CD4+(FIGS. 14B and 14D) from the same donor as in FIGS. 12A-12D. DART-A: ▲; Control DART 1: ▼.
Figure 14C:
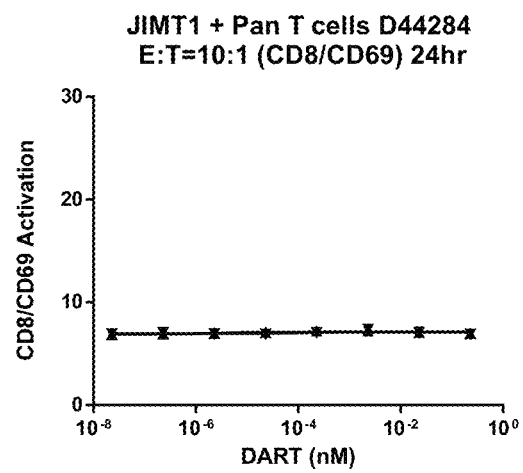
Figure 14B:
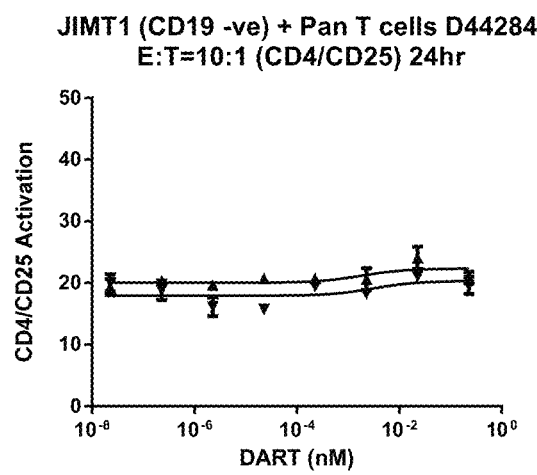
Figure 14D:
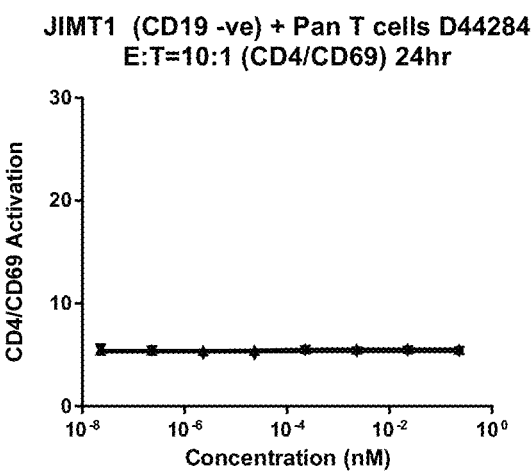

DART-A-mediated cytokine release by T cells in the presence of target cells was also investigated. DART-A dose-dependent cytokine production of TNF-α, IFN-γ, and IL-2 from human T cells was observed with the highest levels (Emax) observed for IL-2 (>7000 pg/mL) after co-incubation with Raji/GF target cells (FIGS. 11A-11C; Table 10). Substantial levels of TNF-α and IFN-γ (~2000-4000 pg/mL) were also produced. As expected, incubation with a Control DART diabody did not result in any detectable cytokine production (FIGS. 11A-11C). Considering the mean EC50 value for the most sensitive cytokine produced by purified human T cells (TNF-α) following incubation with DART-A in the presence of CD19-expressing target cells (Raji/GF) compared with the mean EC50 value for target cell cytoxicity in the least sensitive target cell line (Raji/GF), there is at least a 12-fold apparent safety margin between target cell killing and cytokine production (see Table 9 above).

TABLE 10

EC50 Values for DART-A-Mediated Cytokine Production by Human T Cells in the Presence of Raji/GF Target Cells from Two Independent Donors at E:T = 10:1

| | D47067 | | D44284 | |
|---|---|---|---|---|
| Cytokine | EC50 (pM) | Emax (pg/mL) | EC50 (pM) | Emax (pg/mL) |
| IFN-γ | 8.58 | 3885 | 2.44 | 2219 |
| TNF-α | 6.79 | 3722 | 0.626 | 2361 |
| IL-2 | 11.31 | 8496 | 1.33 | 7492 |

Example 7

Evaluation of DART-A-Mediated Human and Cynomolgus Monkey T Cell Activation

The effect on T cells during DART-A-mediated redirected target cell (Raji/GF cells) lysis was characterized by evaluating expression of the T cell activation markers CD69 and CD25. Both CD25 and CD69 were upregulated in human and cynomolgus monkey CD4+ and CD8+ T cells in a dose-dependent manner (FIGS. 12A-12D and FIGS. 13A-13D), indicating that DART-A-mediated redirected cell killing is associated with a concomitant activation of T cells. No T cell activation was observed in the presence of CD19-negative JIMT-1 cells (FIGS. 14A-14D). These data suggest that T cell activation is dependent upon target cell co-engagement. Further supporting this conclusion, the Control DART 1 did not mediate induction of T cell activation markers (FIGS. 12A-12D and FIGS. 13A-13D).

Example 8

Evaluation of CD19×CD3 Mechanism of Action

Figure 15A:
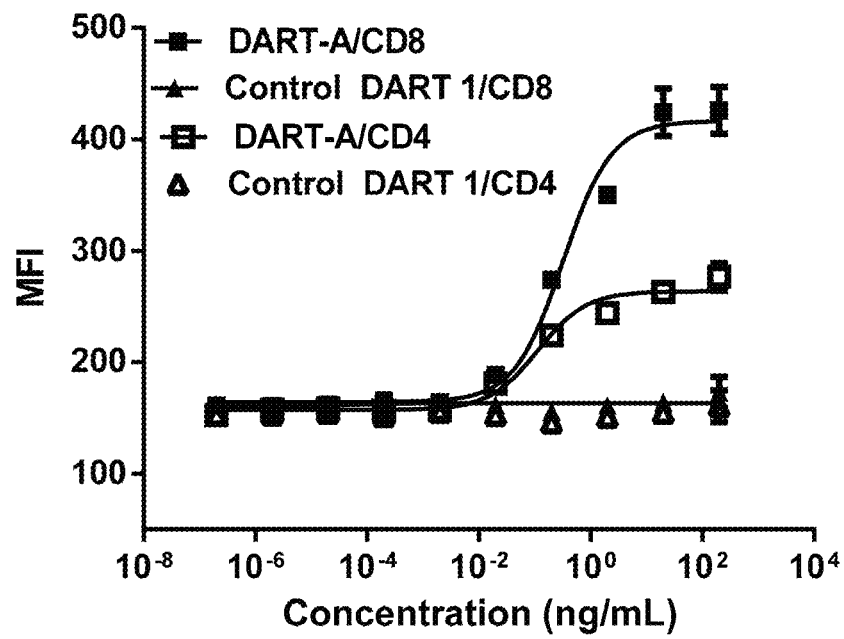
FIGS. 15A-15B show the intracellular levels of granzyme B (FIG. 15A) and perforin (FIG. 15B) staining in CD4+ and CD8+ human T cells after incubation with Raji/GF target cells and DART-A or Control DART 1 at varying concentrations for 24 hours at an E:T ratio of 10:1.
Figure 15B:
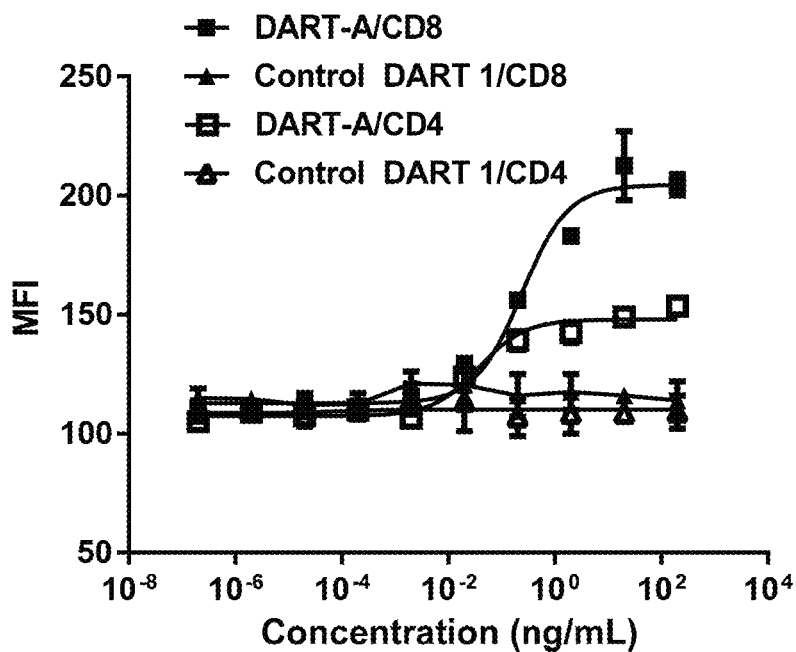

To confirm that the anticipated mechanism for CD19×CD3-mediated redirected cell killing by T cells is mediated by granzyme B and perforin, intracellular levels of granzyme B and perforin were measured in T cells following exposure to DART-A or Control DART 1 in a CTL assay. Dose-dependent upregulation of granzyme B and perforin levels in both CD8+ and CD4+ T cells was observed following 24 hours incubation of human T cells with DART-A in the presence of Raji/GF target cells at an E:T cell ration of 10:1 (FIGS. 15A-15B). In contrast, no upregulation of granzyme B or perforin was observed when human T cells were incubated with Raji/GF target cells and Control DART 1. These data support that DART-A-mediated target cell killing may be mediated through the granzyme B and perforin pathway. Of note, the upregulation of granzyme B (FIG. 15A) and perforin (FIG. 15B) was higher in CD8+ T cells compared with CD4+ T cells, consistent with the expected higher CTL potency of CD8+ T cells.

Figure 16A:
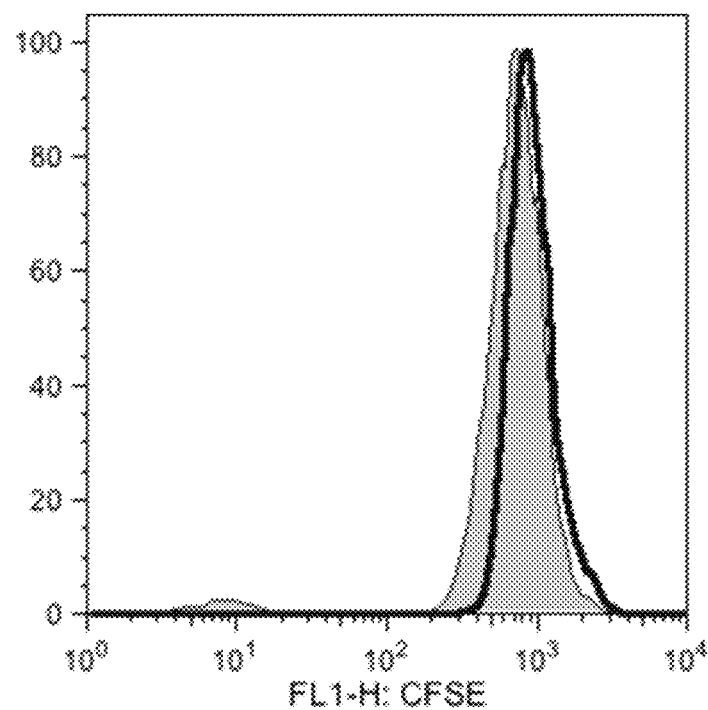
FIGS. 16A and 16B show the proliferation of CFSE-labeled human T cells by FACS analysis after co-culturing with HBL-2 target cells at an E:T ratio of 10:1 in the presence of DART-A or Control DART 1 at 200 ng/mL for 24 hours (FIG. 16A) or 72 hours (FIG. 16B). Staining profiles after co-culture with HBL-2 cells in the presence of DART-A (black lines) or in the presence of Control DART 1 (grey fill) are shown.
Figure 16B:
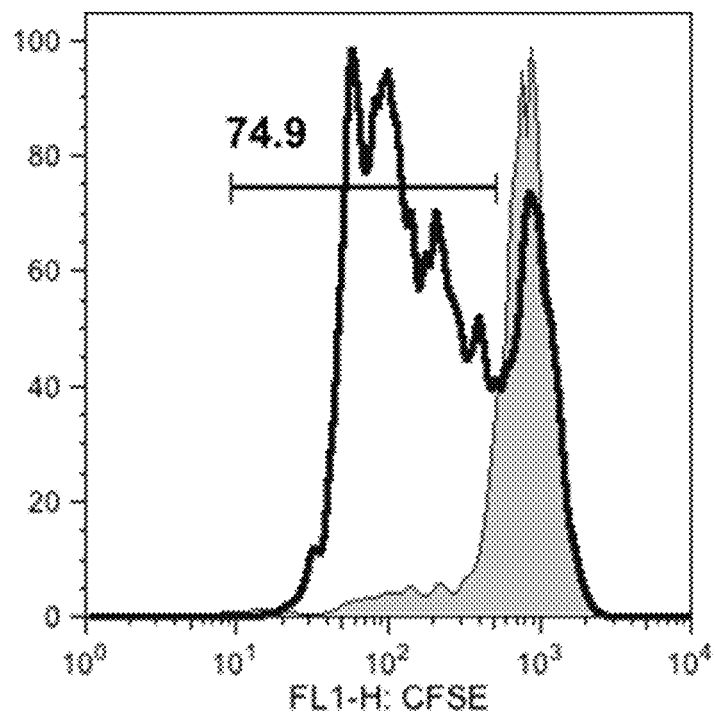

The expansion of T cells during effector:target cell co-engagement by CD9×CD3 was also evaluated, given that proliferation concomitant with T cell activation has been previously reported. CFSE-labeled human T cells were co-cultured with HBL-2 target cells at an E:T cell ratio of 10:1 in the presence of DART-A or Control DART 1 at a concentration of 200 ng/mL. Proliferation of CFSE-labeled T cells was monitored by levels of CFSE dilution over time by FACS analysis (FIGS. 16A-16B). FIG. 16A shows the CFSE-staining profiles in the presence of DART-A or Control DART1 and target cells. The addition of DART-A led to proliferation (CFSE dilution) with about 75% of cells proliferating after 72 hours incubation (FIG. 16B). In contract, no proliferation of CFSE-labeled T cells was observed in the presence of Control DART 1.

Example 9

Efficacy in Co-Mix Xenografts

The inhibition of human B cell lymphoma tumor growth by DART-A was evaluated in female NOD/SCID mice (n=8/group) injected with HBL-2 (human mantle cell lymphoma) or Raji (Burkitt's lymphoma) tumor cells co-mixed with activated human T cells. In both studies, human T cells and tumor cells (HBL-2 or Raji) were combined at a ratio of 1:5 ($1\times10^6$ and $5\times10^6$ cells, respectively) and injected SC into mice on Day 0. Vehicle control (tumor cells alone), DART-A, or Control DART 1 were subsequently administered IV on Days 0, 1, 2, and 3.

Figure 17:
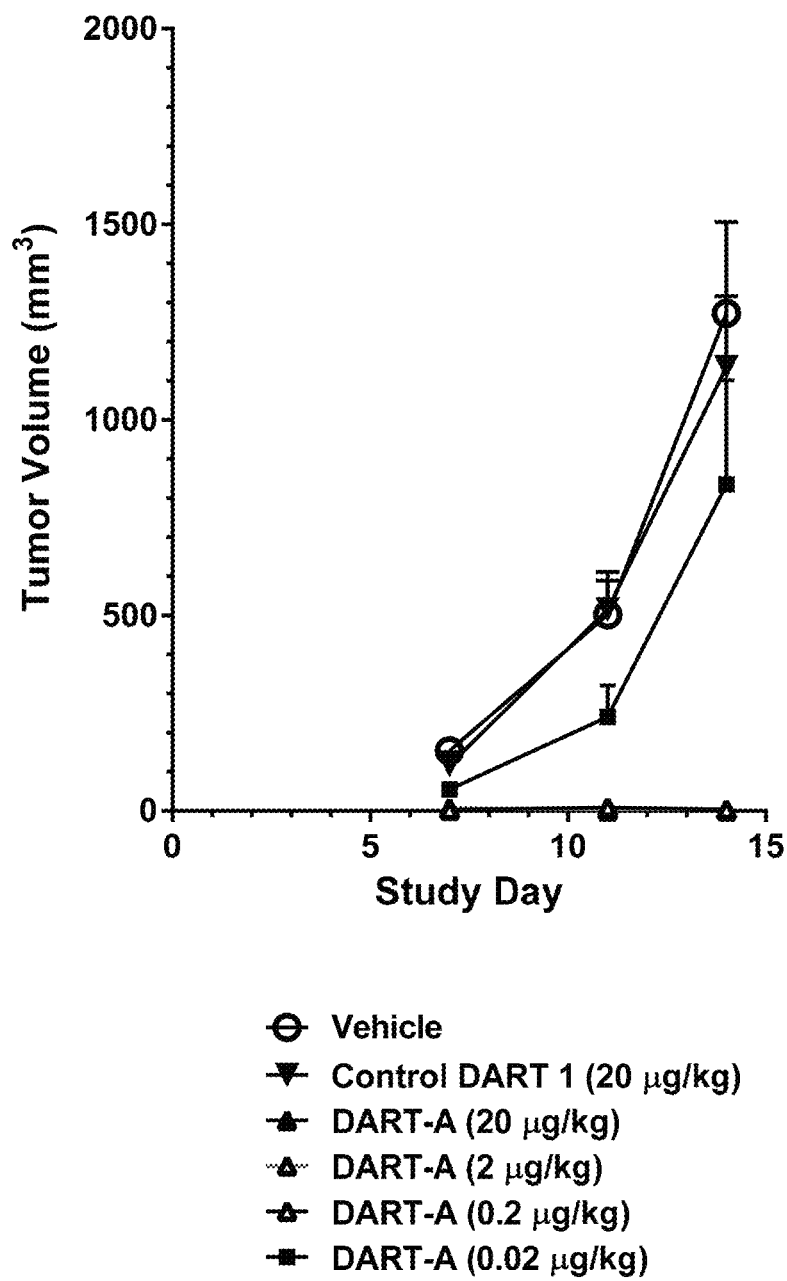
FIG. 17 shows inhibition of tumor growth by the CD19×CD3 bi-specific molecule (DART-A) in mice implanted with HBL-2 tumor cells in the presence of activated human T cells. Female non-obese diabetic/severe combined immunodeficient (NOD/SCID) mice (n=8/group) were implanted subcutaneously (SC) with HBL-2 tumor cells+activated human T cells on Day 0 followed by treatment with vehicle control, Control DART 1, or DART-A on Days 0-3 for a total of 4 doses, administered IV. The human T cells and HBL-2 cells were incubated at a ratio of 1:5 ($1\times10^6$ and $5\times10^6$ cells, respectively). The tumor volume is shown as group mean±SEM.

As shown in FIG. 17, the growth of HBL-2 tumor cells was completely inhibited following IV treatment with DART-A at dose levels ≥0.2 µg/kg. Although treatment with 0.02 µg/kg DART-A appeared to delay the growth of the HBL-2 tumors, the response was not statistically significant. The HBL-2 tumors in the vehicle and control DART groups reached an average tumor volume of approximately 1000 mm³ by Day 13.

Figure 18:
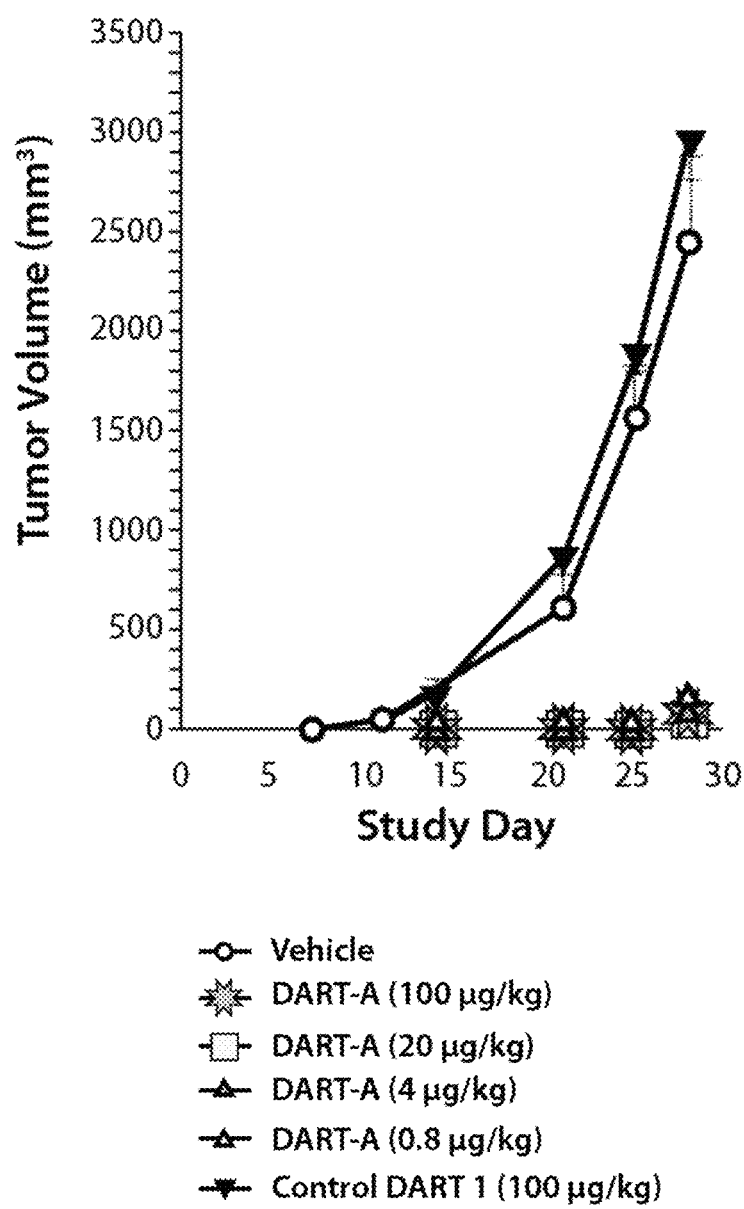
FIG. 18 shows inhibition of tumor growth by the CD19×CD3 bi-specific molecule (DART-A) in mice implanted with Raji tumor cells in the presence of activated human T cells. Female NOD/SCID mice (n=8/group) were implanted SC with Raji tumor cells+activated human T cells on Day 0 followed by treatment with vehicle control, Control DART 1, or DART-A on Days 0-3 for a total of 4 doses administered IV. The human T cells and Raji cells were incubated at a ratio of 1:5 ($1\times10^6$ and $5\times10^6$ cells, respectively). Tumor volume is shown as group mean±SEM.

As shown in FIG. 18, no significant growth of Raji tumor cells was observed through the end of study (Day 28) in mice treated with DART-A at all doses evaluated (0.8 to 100 µg/kg). Treatment with 0.8 µg/kg DART-A resulted in a complete response in 7/8 mice. The Raji tumors in the vehicle and Control DART 1 groups demonstrated tumor growth in vivo with average tumor volumes reaching 2449.4±421.1 mm3 and 2968.2±200.0 mm3, respectively, by the end of the study (Day 28).

Example 10

Efficacy in Established Tumor Models

Figure 19A:
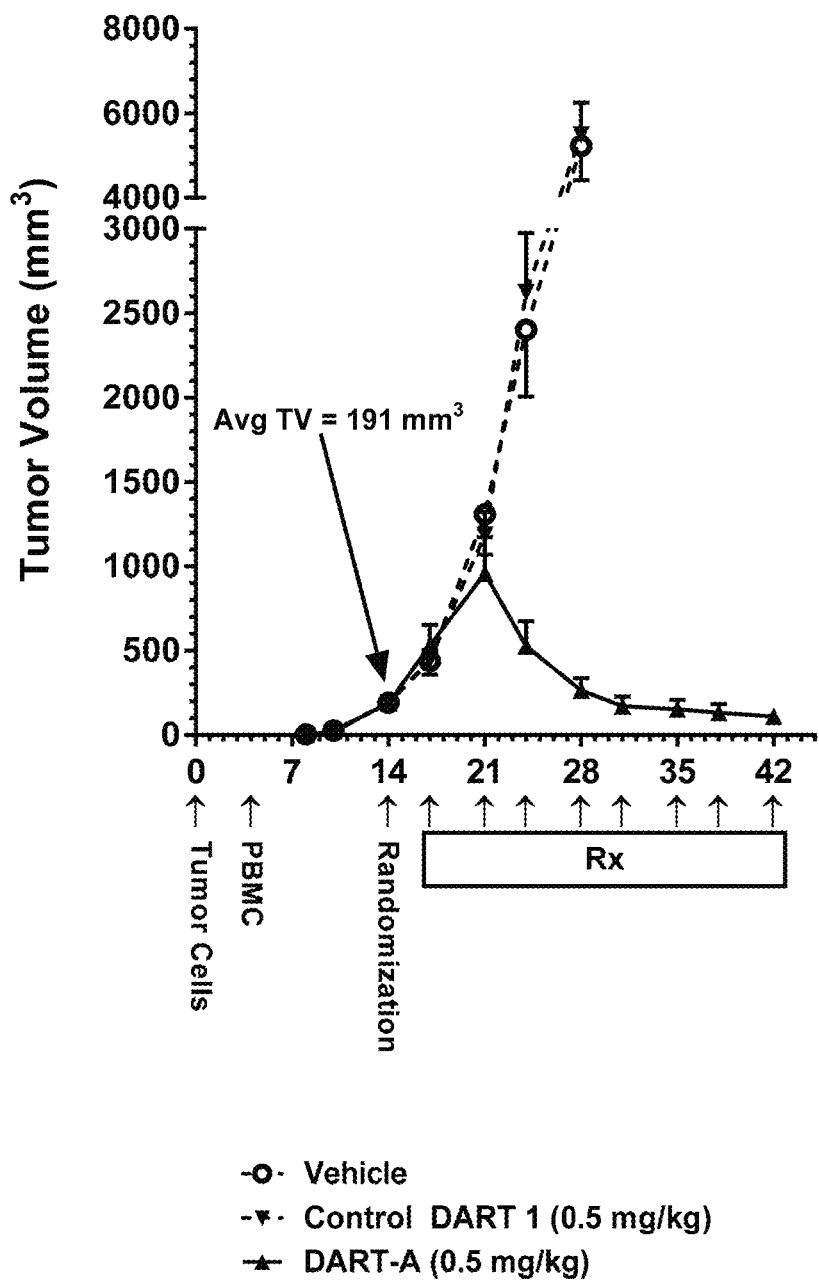
FIG. 19A-19B shows the change in tumor volume over time in mice implanted with HBL-2 tumor cells.

The anti-tumor activity of DART-A was evaluated in an HBL-2 (human mantle cell lymphoma) xenograft model in female NSG B2m−/− mice (n=8/group). Mice were implanted with HBL-2 tumor cells ($5\times10^6$ cells) intradermally (ID) on Day 0 followed by intraperitoneal (IP) injection of PBMCs ($5\times10^7$ cells) on Day 4. Treatment with vehicle, Control DART 1, or DART-A administered IV was initiated on Day 17 when the average tumor volumes for the groups receiving vehicle, Control DART 1, or DART-A were 438.4±80.2, 433.7±63.8, and 531.7±122.5 mm3, respectively. On Day 21 ($2^{nd}$ dose administration), the average tumor volumes had increased to 1306.1±240.4, 1185.6±138.7, and 958.5±216.1 mm³ in the groups treated with vehicle, Control DART 1, and DART-A, respectively. On Day 24 (3$^{rd}$ dose administration), the average tumor volume in the vehicle and Control DART 1 groups had increased to 2401.3±397.4 and 2623.7±351.5 mm3, respectively. In contrast, the group that received DART-A had decreased in volume by 45% to 527.3±148.3 mm³. The tumors in the DART-A treated group continued to decrease in size ultimately reaching a final volume of 111.4±38.9 mm3 on Day 42, an 88.3% decrease from the maximum noted tumor volume (FIG. 19A). In summary, treatment with 0.5 mg/kg of DART-A resulted in the shrinkage of large established HBL-2 mantle cell lymphoma tumors. No relapse was noted up to Day 42 when the study was terminated.

Figure 19B:
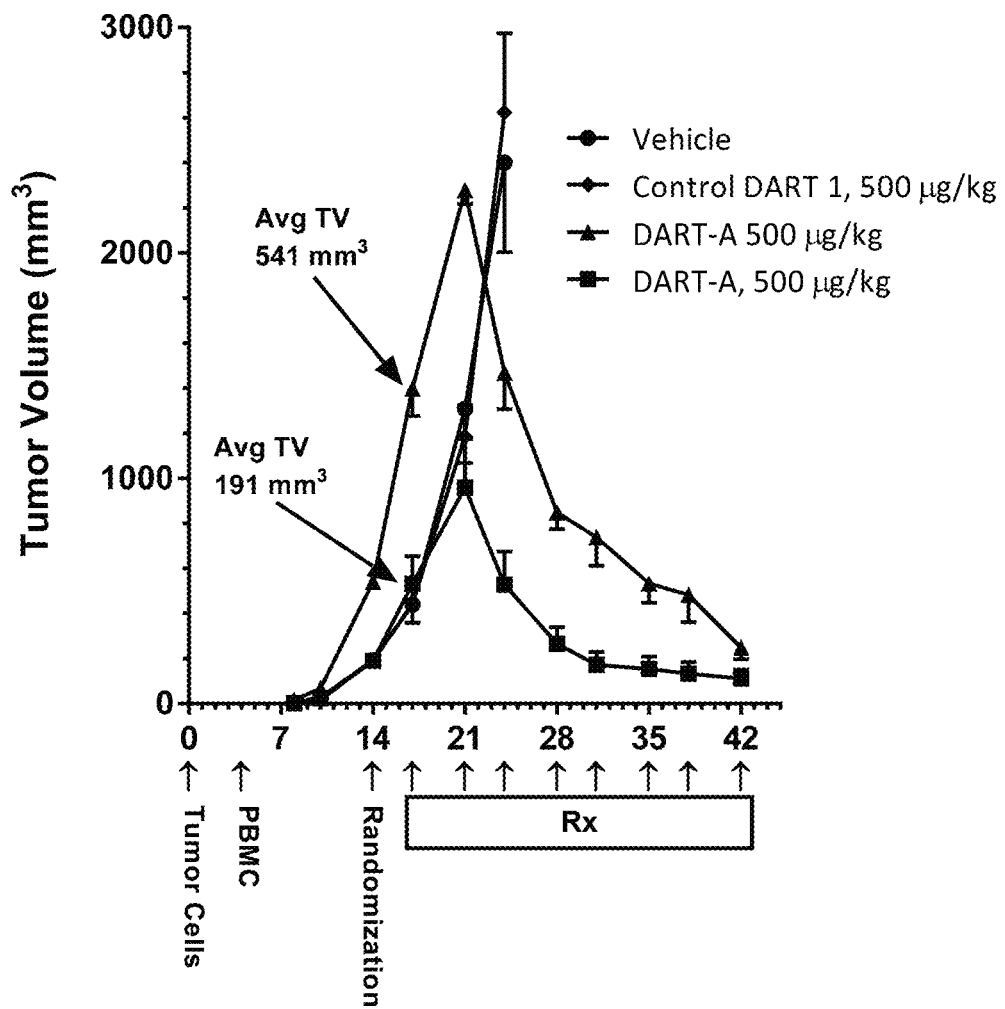

Another group of tumor-bearing mice with an average tumor size of 541 mm³ (n=4 mice) at Study Day 14 were scheduled to be treated with 500 µg/kg DART-A. At the time of the first dose (Study Day 17), the tumors had reached an average volume of 2279±61 mm³ (FIG. 19B). However, prior to the third (Study Day 24) and fourth (Study Day 28) doses, the tumor volumes were 1469±162 and 848±74 mm³, respectively, representing a 36% and 63%, respectively, decrease in tumor volume with respect to the peak volume recorded on Study Day 21 (FIG. 19B). The tumors continued to decrease in size to the extent that on Day 42, the average tumor volume was 248±52 mm³, an 89% decrease in the tumor volume (FIG. 19B).

Example 11

Toxicokinetic Study of DART-A in Cynomolgus Monkeys

A non-GLP (Good Laboratory Practice) toxicology study that was conducted in cynomolgus monkeys to evaluate different doses and regimens of DART-A. Phase A was 1$^{st}$ conducted to evaluate 2-hour IV infusions of intra-animal escalating doses of DART-A each successive week for 4 weeks as summarized in Table 11 (Phase A). Half of the Phase A cynomolgus monkeys in each group (1M/1F) were sacrificed on Day 36 or Day 64. Phase B of the study was subsequently conducted to evaluate 2-hour IV infusions of DART-A administered as fixed doses in each group (Table 11, Phase B). For Groups 3, 4, and 5 the same dose (5, 50, or 500 ng/kg, respectively) was administered each successive week for a total of 3 doses per animal. For Group 6, 500 ng/kg was administered on Study Days 1, 4, 8, 11, and 15 as a 2-hour IV infusion for a total of 5 doses per animal. All Phase B animals were sacrificed on Day 18.

TABLE 11

| Experimental Design (Phase A) | | | | | | | | |
|---|---|---|---|---|---|---|---|---|
| Group No. | Male | Female | Test Material | Dose | Study Dosing Day | Dose Level (ng/kg) | Dose Volume (mL/kg) | Dose Concentration (ng/mL) |
| 1 | 2 | 2 | Vehicle | 1 | 1 | 0 | 0.3 | 0 |
| | | | DART-A | 2 | 8 | 500 | 0.3 | 1700 |
| | | | | 3 | 15 | 5000 | 0.3 | 16,700 |
| | | | | 4 | 22 | 50,000 | 0.3 | 166,700 |
| | | | | 5 | 29 | 50,000 | 0.3 | 166,700 |
| 2 | 2 | 2 | DART-A | 1 | 1 | 0 | 0.3 | 0 |
| | | | | 2 | 8 | 2000 | 0.3 | 7000 |
| | | | | 3 | 15 | 10,000 | 0.3 | 33,300 |
| | | | | 4 | 22 | 100,000 | 0.3 | 333,300 |
| | | | | 5 | 29 | 100,000 | 0.3 | 333,300 |
| Experimental Design (Phase B) | | | | | | | | |
| Group No. | Male | Female | Test Material | Dose | Study Dosing Day | Actual Dose Level * (ng/kg) | Dose Volume (mL/kg) | Actual Dose Concentration (ng/mL) |
| 3 | 1 | 1 | DART-A | 1 | 1 | 5 | 0.3 | 15.0 |
| | | | | 2 | 8 | 5 | 0.3 | 15.0 |
| | | | | 3 | 15 | 5 | 0.3 | 15.0 |
| 4 | 1 | 1 | DART-A | 1 | 1 | 50 | 0.3 | 150.0 |
| | | | | 2 | 8 | 50 | 0.3 | 150.0 |
| | | | | 3 | 15 | 50 | 0.3 | 150.0 |
| 5 | 1 | 1 | DART-A | 1 | 1 | 500 | 0.3 | 1500.0 |
| | | | | 2 | 8 | 500 | 0.3 | 1500.0 |
| | | | | 3 | 15 | 500 | 0.3 | 1500.0 |
| 6 | 1 | 1 | DART-A | 1 | 1 | 500 | 0.3 | 1500.0 |
| | | | | 2 | 4 | 500 | 0.3 | 1500.0 |
| | | | | 3 | 8 | 500 | 0.3 | 1500.0 |
| | | | | 4 | 11 | 500 | 0.3 | 1500.0 |
| | | | | 5 | 15 | 500 | 0.3 | 1500.0 |

* Actual dose level administered based on analysis of the dosing formulation concentrations is shown. It is noted that the actual doses were 10-fold less than the protocol-specified dose levels for Phase B.

1. A Toxicokinetic Study of DART-A in Cynomolgus Monkeys (Phase A)

A non-GLP, pilot, exploratory, dose-escalation study of DART-A was performed in cynomolgus monkeys. In Phase A of the study, two groups of cynomolgus monkeys (n=4/group; 2M/2F) were administered intra-escalating doses of vehicle (Day 1) or DART-A as 2-hour IV infusions on Days 1, 8, 15, 22, and 29. Cynomolgus monkeys in Group 1 received vehicle control→500→5000→50,000→50,000 ng/kg DART-A. Cynomolgus monkeys in Group 2 received vehicle control→2000→10,000→100,000→100,000 ng/kg DART-A. Half of the Phase A cynomolgus monkeys in each group (1M/1F) were sacrificed on Day 36 or Day 64.

There was no DART-A-related mortality during Phase A of the study, and there were no DART-A-related macroscopic or organ weight changes. However, there were DART-A-related effects at dose levels ≥500 ng/kg as detailed below. These effects were consistent with the pharmacology of the test article and were not considered toxicologically significant.

In Phase A on Day 36, DART-A-related microscopic findings were limited to the lymph nodes (inguinal, mandibular, and mesenteric), spleen, and gut-associated lymphoid tissue (GALT) for all Group 1 and 2 animals with no recovery of microscopic findings by Day 64. On Day 36, microscopic findings in the lymph nodes and spleen were similar and consisted of a moderate to marked decrease in the number and size of lymphoid follicular germinal centers identified; in the GALT there was a minimal decrease in the number and size of lymphoid follicular germinal centers. By Day 64, test article-related findings were still present in the lymph nodes, spleen, and GALT; in the lymph nodes and spleen, microscopic findings consisted of mild to marked decreased numbers and size of lymphoid follicular germinal centers and in the GALT there was a minimal decrease in the number and size of lymphoid follicular germinal centers.

Evaluation of bone marrow (sternum), lymph nodes (inguinal, mandibular, and mesenteric), and spleen by immunohistochemistry (IHC) revealed greatly reduced numbers of CD20-positive cells in Phase A animals on Day 36 with only partial recovery of CD20 staining by Day 64. On Day 36, there was, in general, no CD20-positive staining noted in the bone marrow or lymph nodes of Phase A animals with the exception of one animal from Group 1 in which very rare, mild to moderate, CD20-positive staining was present in the germinal centers and lymphocyte corona, respectively, of the inguinal lymph node only. In the spleen, CD20-positive cells were identified in the red pulp only of 3 animals (1 animal from Group 1; 2 animals from Group 2) with the frequency of CD20-positive cells being very rare to rare and minimal or mild to moderate intensity.

In recovery animals (Day 64), very rare to occasional, moderately stained CD20-positive cells were noted in the bone marrow of Group 1 animals only. In the lymph nodes (inguinal, mandibular, and mesenteric), CD20-positive staining was only identified in one animal from Group 1; the frequency of CD20-positive cells was generally greatly reduced in all lymph nodes, while the staining intensity of positive cells was moderate to marked. CD20-positive cells were identified in the spleen of all Group 1 and 2 animals. In Group 1 animals, CD20-positive cells were identified in the lymphoid follicles, periarteriolar lymphoid sheaths (PALS), and red pulp in one animal and in the PALS and red pulp in another animal. In Group 2 animals, very rare to rare CD20-positive cells were identified in the red pulp only with mild staining intensity.

Evaluation of FACS-based B cell depletion, cytokines, and ADA in the Phase A portion of this study is summarized below.

a. FACS Evaluation for B, T, NK Cells, and Monocytes

Whole blood samples were collected for flow cytometric evaluation of a variety of lymphocyte subsets and monocyte cell populations. Phase A animals were assessed at Week −1; prior to dosing on Days 1, 8, 15, 22, and 29; 24 hours post-start of infusion (SOI) on Days 2, 9, 16, 23, and 30; 72 hours post-SOI on Days 4, 11, 18, 25, and 32; Day 35; and on Days 43, 50, 57, and 63 (only applied to the half of the Phase A cynomolgus monkeys from each group with recovery sacrifice on Day 64).

Figure 20A:
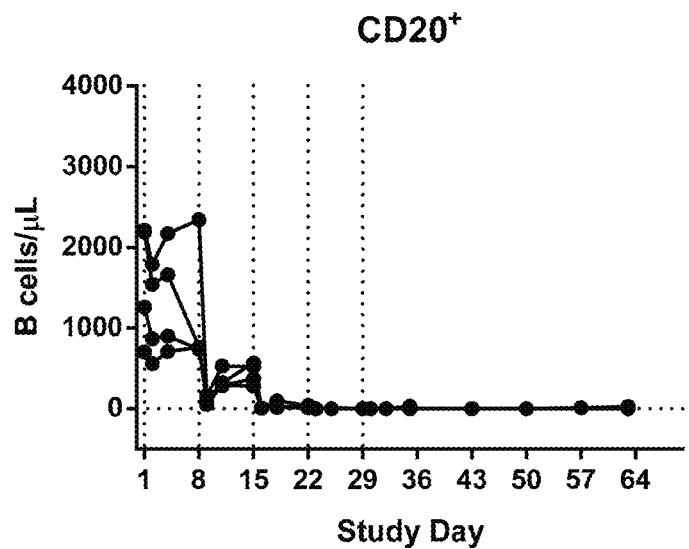
FIGS. 20A-20B show circulating B cell levels over time in cynomolgus monkeys following IV administration of up to 4 cycles of weekly escalating doses of the CD19×CD3 bi-specific DART-A. Cynomolgus monkeys in Group 1 (n=4) were treated with vehicle→0.5→5→50→50 μg/kg DART-A administered IV on Days 1, 8, 15, 22, and 29 (indicated by dotted vertical lines) (FIG. 20A). Cynomolgus monkeys in Group 2 (n=4) were treated with vehicle→2→10→100→100 μg/kg DART-A administered IV on Days 1, 8, 15, 22, and 29 (indicated by dotted vertical lines) (FIG. 20B). Data for each cynomolgus monkey are shown.
Figure 20B:
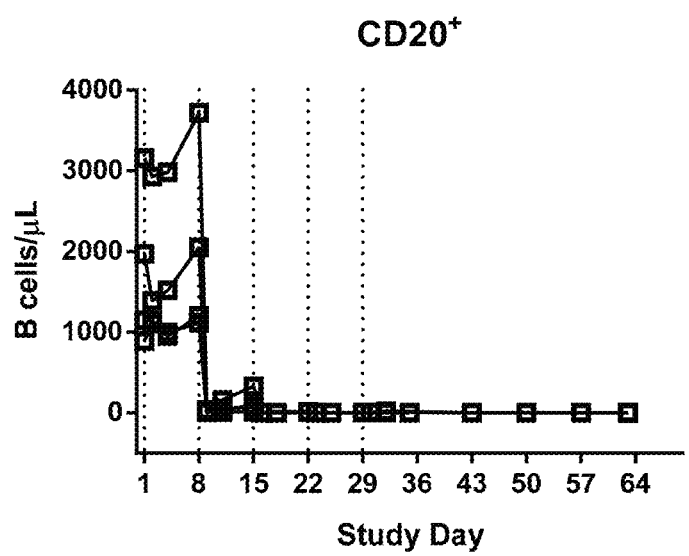
Figure 21A:
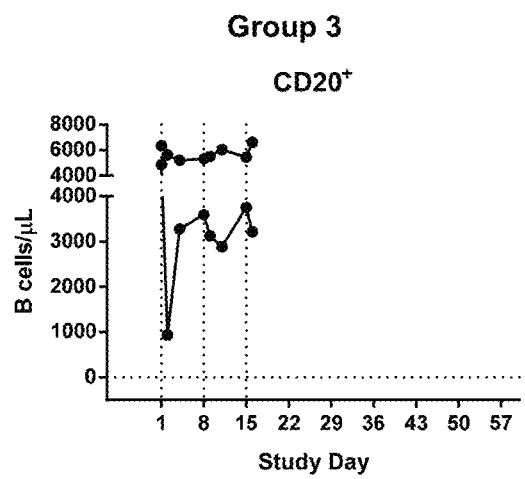
FIGS. 21A-21D shows circulating B cell levels over time in cynomolgus monkeys following IV administration of up to 3 cycles of weekly fixed doses or up to 5 cycles of every 3-day fixed doses of DART-A. Cynomolgus monkeys in Groups 3-5 (n=2 per group) were treated with CD19×CD3 bi-specific DART-A. Group 3 (FIG. 21A) received 5 ng/kg DART-A; Group 4 (FIG. 21B) received 50 ng/kg DART-A; and Group 5 (FIG. 21C) received 500 ng/kg DART-A. DART-A was administered IV on Days 1, 8, and 15 (indicated by dotted vertical lines). Cynomolgus monkeys in Group 6 (n=2) (FIG. 21D) were treated with 500 ng/kg DART-A administered IV on Days 1, 4, 8, 11, and 15 (indicated by dotted vertical lines). Data for each cynomolgus monkey are shown.
Figure 21B:
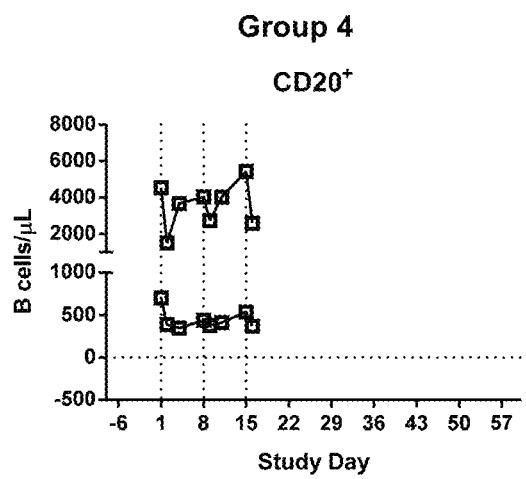
Figure 21C:
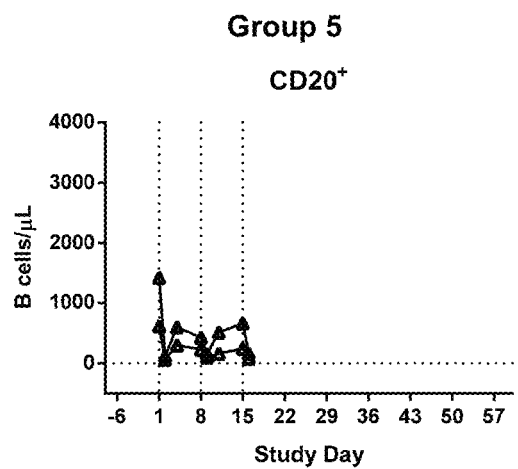
Figure 21D:
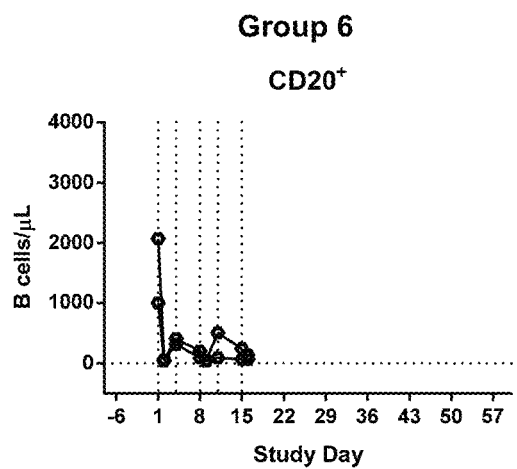

Dose-dependent reductions in the absolute counts of B lymphocytes (CD20+) were present beginning at Day 9 (24 hours post-SOI) for both groups (Groups 1 and 2). The B lymphocyte populations for the 500 ng/kg/dose animals (Group 1) trended toward pre-study levels on Days 11 and 15, whereas the values for the 2000 ng/kg/dose animals (Group 2) remained reduced. The B lymphocytes were virtually depleted at Day 16 (24 hours post-SOI) following the second DART-A dose administration for both dose groups and remained depleted for all subsequent time points (FIGS. 20A-20B). The B lymphocyte depletion was an anticipated pharmacologic effect of DART-A.

Other immune cell populations, including monocytes, natural killer (NK) cells, and T cells, were also evaluated by flow cytometry.

Transient, dose-dependent reductions in the number of CD14+ monocytes were present beginning on Day 9, 24 hours post-SOI, for the majority of animals dosed at 2000 ng/kg (Group 2). Reductions in the number of CD14+ monocytes were also present at Day 16 and Day 23, 24 hours post-SOI, for the majority of animals dosed at 5000 ng/kg and 50,000 ng/kg, respectively (Group 1) and for all animals dosed at 10,000 ng/kg and 100,000 ng/kg, respectively (Group 2). The CD14+ monocyte populations recovered quickly after the end of each infusion and generally reached or exceeded pre-study baseline values by the next pre-dose time point before reducing again 24 hours after subsequent doses. At the end of the dosing phase, the CD14+ monocytes fluctuated with values that trended toward pre-study levels and maintained values that were at or above pre-study baseline levels.

Transient, dose-dependent reductions were also observed for the total T lymphocytes, CD4+T lymphocytes, CD8+T lymphocytes, T regulatory lymphocytes (CD4+/CD25+/FoxP3+), CD159a+NK cells, CD16+NK cells, and CD16+/CD159a+NK cells, with the greatest reductions observed for the 2000 ng/kg/dose animals (Group 2) at Day 9 (24 hours post-SOI) and following the 5000 ng/kg/dose in Group 1 animals on Day 16 (24 hours post-SOI). The T lymphocyte and NK cell subsets recovered quickly after the end of each infusion and generally reached or exceeded pre-study baseline levels before the next dose on Days 15 and 22 before reducing again 24 hours following each dose. No further reductions were present for Group 1 or 2 at Day 30 (24 hours post-SOI) following the doses administered on Day 29.

The CD4+ and CD8+T lymphocyte populations were also assessed for up-regulation of the activation markers PD-1, TIM-3, CD25, and CD69 to determine the activation status of the cells after DART-A dose administration. Variable increases in the frequencies of PD-1+, CD69+, and CD25+ in CD4+T lymphocytes and of PD-1+ and CD69+ in CD8+T lymphocytes were present after dosing, indicating an increase in the frequencies of activated CD4+ and CD8+T lymphocytes in the whole blood after dosing. The frequency of CD69+, PD-1+, and CD25+(to a lesser degree, occurring in some but not all animals) in CD4+T lymphocytes and PD-1+ and CD69+ in CD8+T lymphocytes increased following the 500 ng/kg (Group 1) and 2000 ng/kg (Group 2) doses beginning on Day 9 (24 hours post-SOI). These values generally remained above baseline levels and were highly variable for all subsequent time points. The relative percentages of CD25+/CD69+, TIM-3+, and PD-1+/TIM3+ lymphocyte populations were generally <1% of the total CD4+ and CD8+T lymphocyte populations, making any DART-A- related changes difficult to assess. Collectively, these data suggest that DART-A administration resulted in an upward trend in PD-1 and CD69 expression on both CD4+ and CD8+T lymphocytes together with a more modest increase in CD25+ in CD4+T lymphocytes in some, but not all, animals.

b. Cytokine Evaluation

Serum IL-2, IL-4, IL-5, IL-6, IL-10, TNF-α, and IFN-γ levels were determined (EMD Millipore assay) pre-dose and at 4 and 24 hours following the start of each infusion. Transient, DART-A dose-correlated increases in IL-10 levels (up to 1918 pg/mL) were observed 4 hours following the start of infusion when cynomolgus monkeys were administered escalating doses ranging from 500 to 50,000 ng/kg in Group 1 and from 2000 to 100,000 ng/kg in Group 2 by IV infusion over a 2-hour period for the first 3 doses; levels generally returned to baseline within 24 hours of the start of infusion. There was generally no IL-10 detected 4 hours following the start of the last DART-A infusion in either group (50,000 ng/kg in Group 1 or 100,000 ng/kg in Group 2) with one exception (Animal 2502). Animal 2502 experienced a transient IL-10 increase to 332 pg/mL following the last dose (100,000 ng/kg on Day 29), but this increase was lower in magnitude than the IL-10 increase following the first 100 µg/kg dose on Day 22 (570 pg/mL). One cynomolgus monkey (Animal 1001) at the 50,000 ng/kg dose level, who experienced the highest IL 10 levels (1918 pg/mL on Day 22), also experienced concurrent transient increases in IL-2 (32 pg/mL), IL 5 (45 pg/mL), and IL-6 (357 pg/mL). Transient increases in IL-6 levels were observed in the majority of cynomolgus monkeys 4 hours following infusion of DART-A; however, the increases were generally similar to or of a lower magnitude (with the exception of Animal 1001 described above) compared with the levels observed following infusion of vehicle control on Day 1 (up to 190 pg/mL) with no clear dose-response. There were no apparent clinical observations associated with increased cytokine levels.

There were no consistent changes in levels of IL-5, IL-4, IL-2, IFN-γ, or TNF-α following infusion of DART-A. Levels of IL-5 were variable with about half the animals in each group experiencing small and transient increases (~10-20 pg/mL; except Animal 1001 discussed above) following DART-A infusion on Days 15 or 22. Levels of IFN-γ were also variable across the study with small (<~10 pg/mL) and transient increases following infusion in some animals.

2. A Toxicokinetic Study of DART-A in Cynomolgus Monkeys (Phase B)

In Phase B of the study, 4 groups of cynomolgus monkeys (n=2/group; 1M/1F) were administered fixed doses of DART-A as 2-hour IV infusions with 3 doses administered on Days 1, 8, and 15 for Group 3 (5 ng/kg), Group 4 (50 ng/kg), and Group 5 (500 ng/kg); and 5 doses administered on Days 1, 4, 8, 11, and 15 for Group 6 (500 ng/kg). All Phase B animals were euthanized on Day 18.

There was no DART-A-related mortality during Phase B of the study, and there were no DART-A-related macroscopic or organ weight changes.

On Day 18, DART-A-related microscopic findings were limited to the lymph nodes (inguinal, mandibular, and mesenteric) and spleen of Groups 4, 5, and 6 animals and consisted of a minimal to mild decrease in the number and size of lymphoid follicular germinal centers identified with no apparent change in the size and/or cell density of the lymphoid tissue comprising the PALS in the spleen. There were no reported microscopic findings noted in Group 3 (5 ng/kg).

Additional formalin-fixed paraffin-embedded sections of bone marrow (sternum), lymph nodes (inguinal, mandibular, and mesenteric), and spleen were evaluated by IHC for cell populations that express CD20 (Mordenti, J. et al. (1991) "*Interspecies Scaling Of Clearance And Volume Of Distribution Data For Five Therapeutic Proteins*," Pharm. Res. 8(11):1351-1359). There was no appreciable difference in the distribution and/or staining intensity of CD20-positive cells in the bone marrow (sternum), lymph nodes (inguinal, mandibular, and mesenteric), or spleen in Groups 3, 4, 5, or 6. In all tissues, positive staining was associated with the cell membrane. In general, in the bone marrow occasional CD20-positive cells were located throughout the bone marrow stroma and staining intensity of positive cells was moderate to marked. In the lymph nodes, CD20-positive cells were primarily associated with the germinal centers and lymphocyte corona of follicles with fewer CD20-positive cells located within the paracortex, medullary cords, and medullary and subcapsular sinuses. Staining intensity in the germinal centers, lymphocyte corona, medullary cords, and medullary and subcapsular sinuses was moderate to marked. Staining intensity in the paracortex was of mild to marked. In the spleen, CD20-positive cells were primarily associated with the germinal centers, follicular mantle, and marginal zone of lymphoid follicles with fewer CD20-positive cells within PALS and red pulp and staining was of moderate to marked intensity.

Evaluation of FACS-based B cell depletion, cytokines, and ADA in the Phase B portion of this study is summarized below.

a. FACS Evaluation for B Cells, T Cells, NK Cells, and Monocytes

Whole blood samples were collected for flow cytometric evaluation of a variety of lymphocyte subsets and monocyte cell populations. Phase B animals were assessed at Week −1; prior to dosing on Days 1, 4, (Group 6 only) 8, 11 (Group 6 only), and 15; 24 hours post-SOI on Days 2, 9, and 16; and at 72 hours post-SOI on Days 4 and Day 11 (Group 3-5 only).

Marked dose-dependent reductions in the total number of B lymphocytes (CD20+) were present 24 hours after the start of infusion for doses administered on Days 1, 8, and 15. The greatest reductions for the 5 ng/kg (Group 3), 50 ng/kg (Group 4), and 500 ng/kg (Groups 5 and 6) treatment groups were present at Day 2 (24 hours post-SOI). The B lymphocyte populations recovered quickly after each infusion in Groups 3 and 4 and presented with fluctuating values near pre-study baseline levels at all other time points. Groups 5 and 6 presented with minimal recovery between doses and maintained generally reduced values at all time points after Day 2 (FIGS. 21A-21D). Sustained B lymphocyte depletion was an anticipated pharmacologic effect of DART-A at higher doses.

Other immune cell populations, including monocytes, NK cells, and T cells, were also evaluated by flow cytometry.

Transient, dose-dependent reductions were present for total CD14+ monocytes beginning on Day 2 (24 hours post-SOI) for most animals in all dose groups (Groups 3-6). Additional changes in CD14+ monocytes were also present for most animals in all dose groups on Days 9 and 16 and values were highly variable.

Transient, dose-dependent reductions in the number of total T lymphocytes, T regulatory lymphocytes (CD4+/CD25+/FoxP3+), CD4+T lymphocytes, CD8+T lymphocytes, and NK cell subsets were present, with the greatest reductions for all groups (Group 3-6) generally present on Day 2 (24 hours post-SOI). The T lymphocyte subsets recovered quickly after each infusion and all doses generally reached or exceeded pre-study levels before the next infusion in all groups. Additional reductions for the CD4+, CD8+, and T regulatory lymphocytes were also present at Days 9 and 16 (24 hours post-SOI) for the 50 ng/kg (Group 4), 500 ng/kg (Group 5), and multi-dosed 500 ng/kg (Group 6) dosed animals; however, the reductions present at these time points were of a lower magnitude compared with those present at Day 2 following the first DART-A dose. The NK cell subsets generally trended toward recovery after the first day of infusion and presented with variable values across all remaining time points.

The CD4+ and CD8+T lymphocyte populations were assessed for up-regulation of the activation markers PD-1, TIM-3, CD25, and CD69 to determine the activation status of the cells after DART-A dose administration. The relative percentages of CD25+/CD69+(for CD4+T lymphocytes only), TIM-3+, and PD-1+/TIM3+ in the CD4+ and CD8+T lymphocyte populations were generally <1% of the total CD4+ and CD8+T lymphocyte populations, making any DART-A-related changes difficult to assess. Increases in the frequencies of PD-1+ and CD69+ in CD4+ and CD8+T lymphocytes were present across multiple time points for the 500 ng/kg/dose animals in Groups 5 and 6 beginning on Day 2 (24 hours post-SOI). Additionally, more modest increases in the frequency of CD25+ in CD4+ and CD8+T lymphocytes were present for the 500 ng/kg/dose animals (Groups 5 and 6) beginning on Day 2 (24 hours post-SOI), as well as increases in the relative percentages of CD25+/CD69+ in CD8+T lymphocytes for the multi-dose 500 ng/kg/dose animals (Group 6). Increases of a magnitude comparable to those present on Day 2 were also generally present on Days 9 and 16 (24 hours post-SOI) following subsequent doses. Collectively, these data indicate that DART-A administration resulted in an upward trend in PD-1, CD69, and CD25 expression on CD4+ and CD8+T lymphocytes.

b. Cytokine Evaluation

Serum IL-2, IL-4, IL-5, IL-6, IL-10, TNF-α, and IFN-γ levels were determined (EMD Millipore assay) prior to dosing on Days −7, 8, and 15; and at 4 and 24 hours post-start of infusions on Days 1, 8, and 15. Transient and dose-correlated increases in IL-10 levels (up to 173 pg/mL) were observed 4 hours following the start of the 1st DART-A infusion when cynomolgus monkeys were administered DART-A doses of 5, 50, or 500 ng/kg (Groups 3-6); levels generally returned to baseline within 24 hours of the start of infusion. Increases in IL-10 appeared to be more pronounced in all groups following the $1^{st}$ dose of DART-A compared with IL-10 increases following the $2^{nd}$ and $3^{rd}$ doses (<22 pg/mL in all animals with the exception of Animal 5001 described below), suggesting either "desensitization" of cytokine release and/or rapid reduction/elimination of the target cell population responsible for T cell activation following the $1^{st}$ dose. Transient increases in IL-6 levels (up to 162 pg/mL) were variably observed in some animals across all dose groups 4 hours following the start of each DART-A infusion with levels generally returning to at or near baseline levels within 24 hours. However, based on the data generated from vehicle administration in Phase A in which increases in IL-6 levels up to 190 pg/mL were observed, the levels of IL-6 fluctuation in Phase B (≤162 pg/mL) may not necessarily reflect drug-related responses. There were no consistent changes observed in levels of IL 5, IL-4, IL-2, IFN γ, or TNF-α throughout the study.

One cynomolgus monkey (Animal 5001) experienced elevated levels of IFN-γ, TNF-α, IL-2, IL-4, IL 5, and IL-10 on Day 8 prior to the 2nd DART-A infusion. Cytokine levels further increased (IL-4, IL-5, IL-6, IL-10, IFN-γ, and TNF-α) or remained stable (IL-2) at 4 hours following the 2nd infusion on Day 8. Cytokine levels began to decline by 24 hours following the 2nd dose with variable increases in some cytokines following the 3rd DART-A infusion on Day 15. Although all cytokine levels declined from their peak values, cytokine levels remained elevated above baseline levels at the last time point evaluated (Day 16) in this cynomolgus monkey. There were no apparent clinical observations associated with increased cytokine levels.

Example 12

Ig-Like Half-Life in Human FcRn Transgenic Mice

Figure 22:
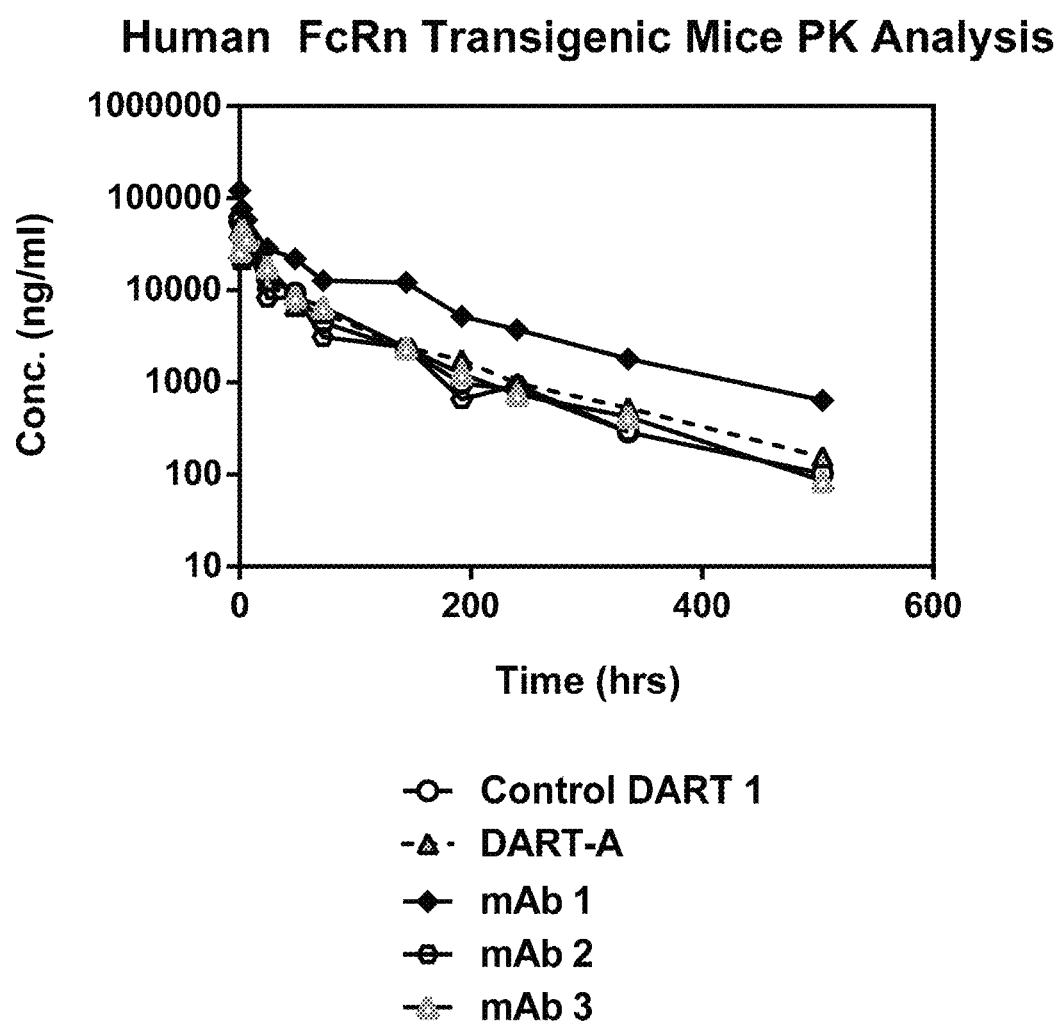
FIG. 22 shows DART-A human FcRn transgenic mice pharmacokinetic (PK) analysis. mAb 1, mAb 2 and mAb 3 are irrelevant humanized IgG1 antibodies employed as a control to permit determination of typical antibody half-life in the transgenic animals.

A human FcRn transgenic mouse pharmacokinetic (PK) study was performed using the human FcRn transgenic mouse strain B6.Cg-Fcgrt$^{tm1Dcr}$ (CAG-FCGRT)276Dcr/DcrJ mouse (Stock Number 004919), available from the Jackson Laboratories, Bar Harbor, Me., US, to evaluate DART-A and Control DART 1 (FIG. 22). The terminal half-life was 85.6 and 92.1 hours, respectively. Three human mAbs were also evaluated in same test system for comparison and had terminal half-lives ranging from 58.7 to 102.7 hours.

Example 13

Efficacy in Disseminated Raji Cell Leukemia/Lymphoma Models in Human PBMC-Reconstituted Mice Disseminated tumor models were established using luciferase-transduced Raji lymphoma cells (Raji.luc) in female NSG B2m−/− mice reconstituted with human PBMCs in which the mice were treated with vehicle, Control DART 1 or DART-A either one day post-tumor cell injection (the "early treatment" or leukemia paradigm) or after at least two weeks of growth in vivo (the "established tumor" or lymphoma model).

Early Treatment Model

Following human PBMC reconstitution on Study Day −14, Raji.luc lymphoma cells were injected on Study Day 0 and treatment was initiated the following day (Study Day 1). Vehicle control, 0.5 mg/kg Control DART 1 or 0.5 mg/kg DART-A were injected IV once every 3-4 days for a total of 12 doses (i.e., Study Days 1, 4, 6, 8, 11, 13, 15, 18, 20, 22, 25, and 27). Mice were followed for survival through Study Day 54 or Study Day 56.

Figure 23:
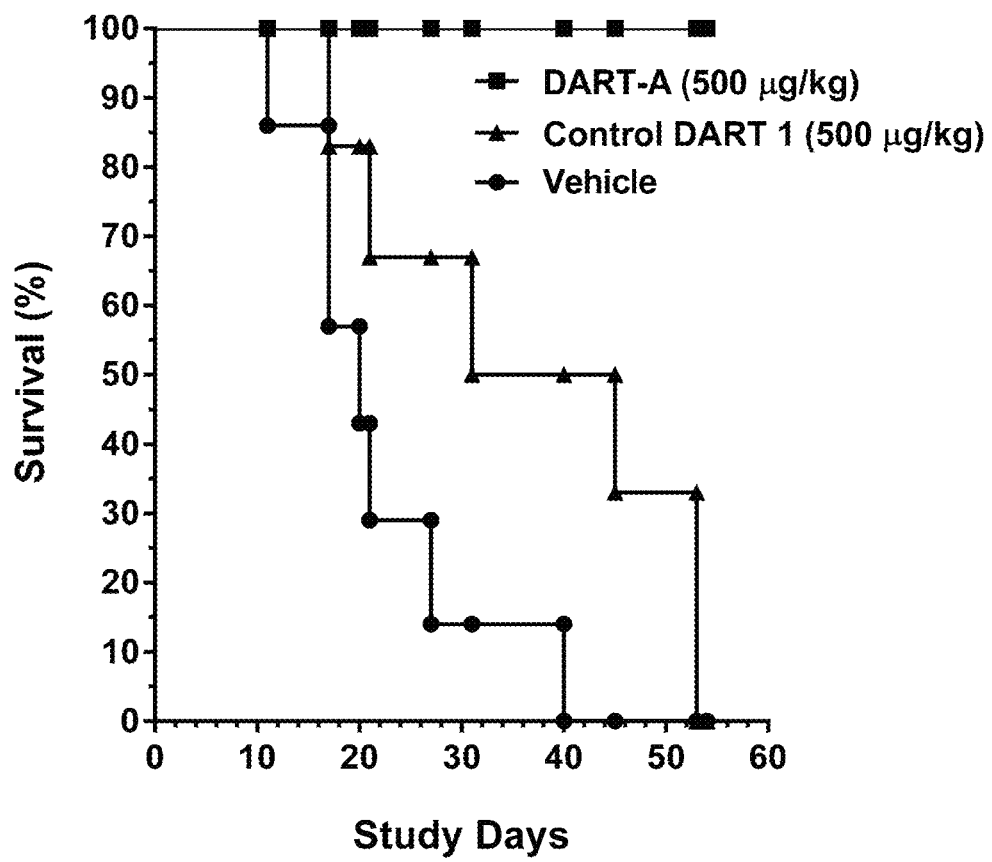
FIG. 23 shows the survival curves in a disseminated Raji-luc cell leukemia model in human PBMC-reconstituted mice following treatment with 500 μg/kg DART-A (■), 500 μg/kg Control DART 1 (▲) or vehicle control (•).

In the groups receiving vehicle or Control DART 1, diffuse disseminated tumor cell profiles rapidly coalesced and expanded in the majority of mice by Weeks 2 and 3. Animal deaths in these two control groups were noted as early as two weeks post-tumor cell implant. All mice in the vehicle or Control DART 1 groups died or were humanely sacrificed (i.e., if the animals became moribund or lost more than 15% of their body weight) by Study Days 40 or 53, respectively. The survival curves are depicted in FIG. 23. In contrast, the group treated with DART-A showed no tumor cell growth at any time point and no animal deaths were observed through the end of the study. The survival curve is depicted in FIG. 23.

Figure 24:
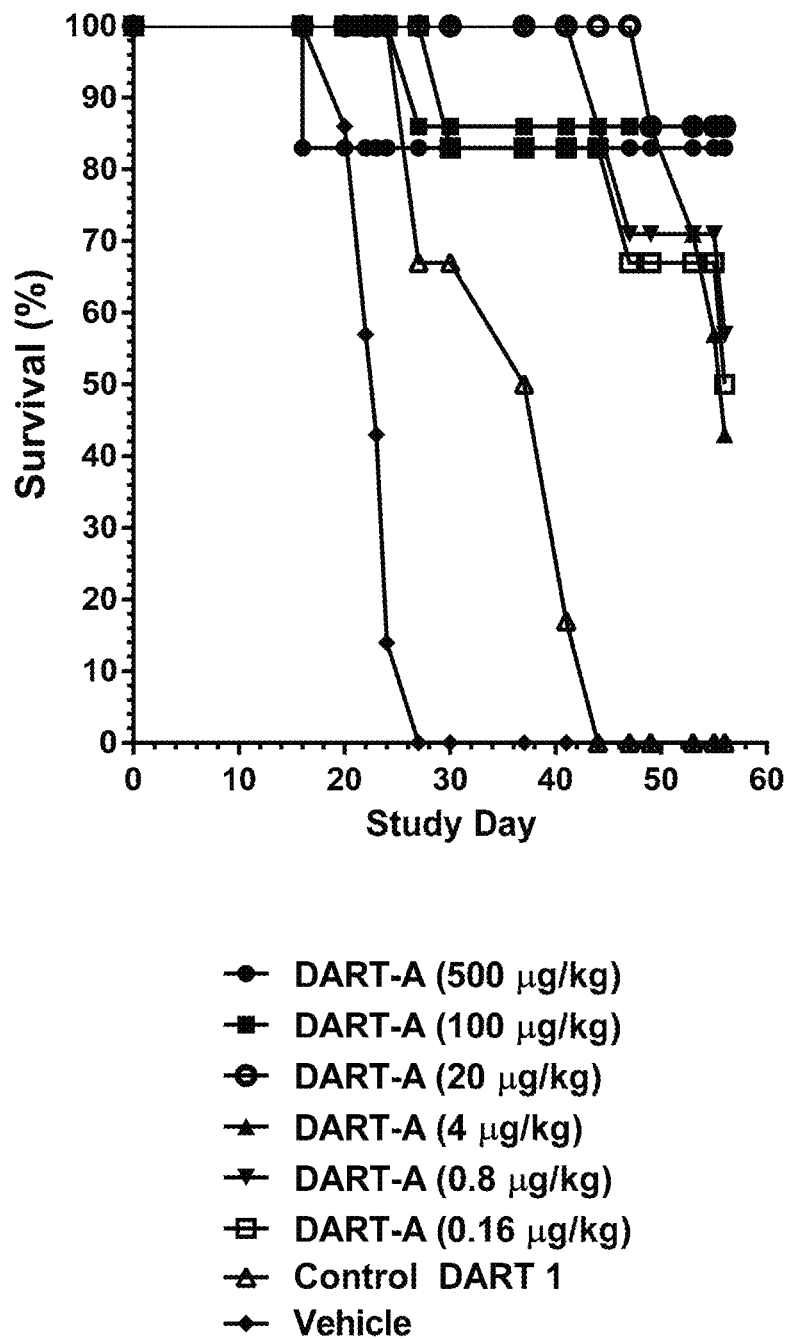
FIG. 24 shows the survival curves in a disseminated Raji-luc cell leukemia model in human PBMC-reconstituted mice following treatment with 500 μg/kg (•), 100 μg/kg (■), 20 μg/kg (○), 4 μg/kg (▲), 0.8 μg/kg (▼) or 0.16 μg/kg (□) DART-A, 500 mg/kg (Δ) Control DART 1 or vehicle control (♦).

A dose-range finding study was conducted in a follow-up experiment under the same experimental conditions described above, except 0.16 µg/kg, 0.8 µg/kg, 4 µg/kg, 20 µg/kg, 0.1 mg/kg or 0.5 mg/kg DART-A were injected IV once every 3-4 days for a total of 12 doses (i.e., Study Days 1, 4, 6, 8, 11, 13, 15, 18, 20, 22, 25, and 27). Vehicle and Control DART 1 were administered as described above on the same Study Days. A rapid progression of Raji.luc tumor growth was observed in mice treated with vehicle or Control DART 1. DART-A demonstrated efficacy at all doses tested with the majority of mice being alive (>8%) and tumor free at the end of the study (Day 56) at doses as low as 20 µg/kg (FIG. 24).

Established Tumor Model

The ability of CD19×CD3 to control Raji.luc cell tumor burden when treatment was delayed, was tested in a separate set of experiments. In the established tumore model, human-PBMC-reconstituted mice were inoculated IV with Raji.luc cells of Study Day 0 (approximately one week after PBMC injection) and allowed to grow for 14 days prior to treatment initiation.

Figure 25:
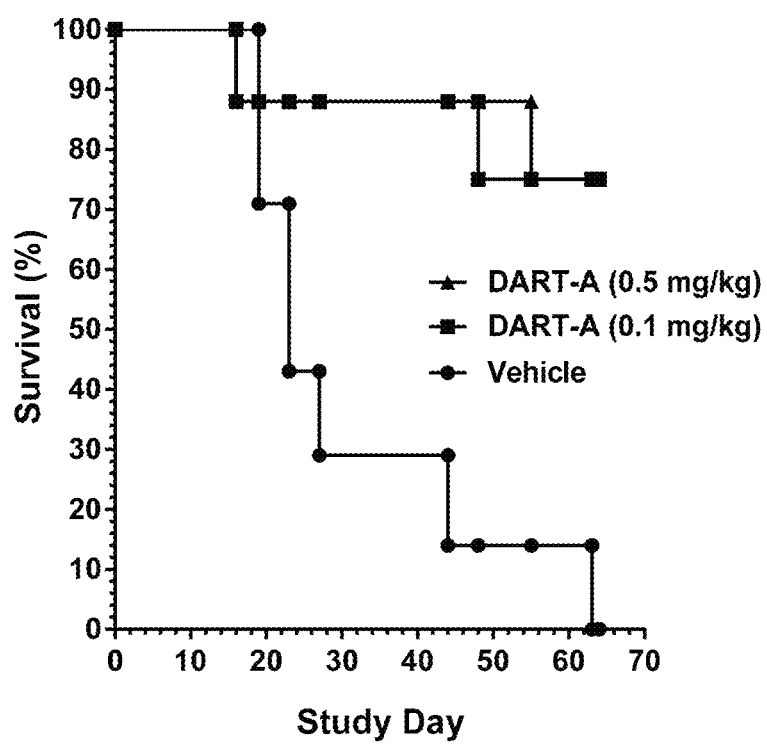
FIG. 25 shows the survival curves in a Raji.luc cell lymphoma model in human PBMC-reconstituted mice following treatment with 0.5 mg/kg DART-A (▲), 0.1 mg/kg DART-A (■) or vehicle control (•).

Mice were randomized on Study Day 12 into 3 groups based on tumor burden and subsequently treated with vehicle, 0.1 mg/kg DART-A or 0.5 mg/kg DART-A starting on Study Day 14 (2 weeks after Raji.luc cell inoculation) for a total of 10 doses (i.e., Study Days 14, 15, 16, 19, 21, 23, 30, 33, 35 and 37). In the vehicle control group, the initial foci markedly increased in size by the end of the first week of treatment and 5/7 mice died within 2 weeks of treatment initiation (FIG. 25). In contrast, the tumor burden in the majority of animals in both DART-A treatment groups was dramatically reduced or cleared during the first week of treatment. Only one animal in each DART-A treatment group, each with a relatively high tumor burden present at randomization, died during the first week of treatment (FIG. 25). By Study Day 50, only 2 mice in the 0.1 mg/kg DART-A treatment group had peripheral tumors remaining.

A dose-range finding study in the delayed treatment model was conducted under the general experimental conditions described above. In this experiment, human PBMC-reconstituted mice were inoculated IV with Raji.luc cells on Study Day 0 (5 days after PBMC injection) and allowed to grow to Study Day 14 prior to randomization. Treatment was initiated on Study Day 15 with vehicle, 0.1 mg/kg Control DART 1 or 0.16 µg/kg, 0.8 µg/kg, 4 µg/kg, 20 µg/kg, 0.1 mg/kg or 0.5 mg/kg DART-A for a total of 9 doses (i.e., Study Days 15, 17, 21, 23, 25, 28, 30, 32 and 35).

Figure 26:
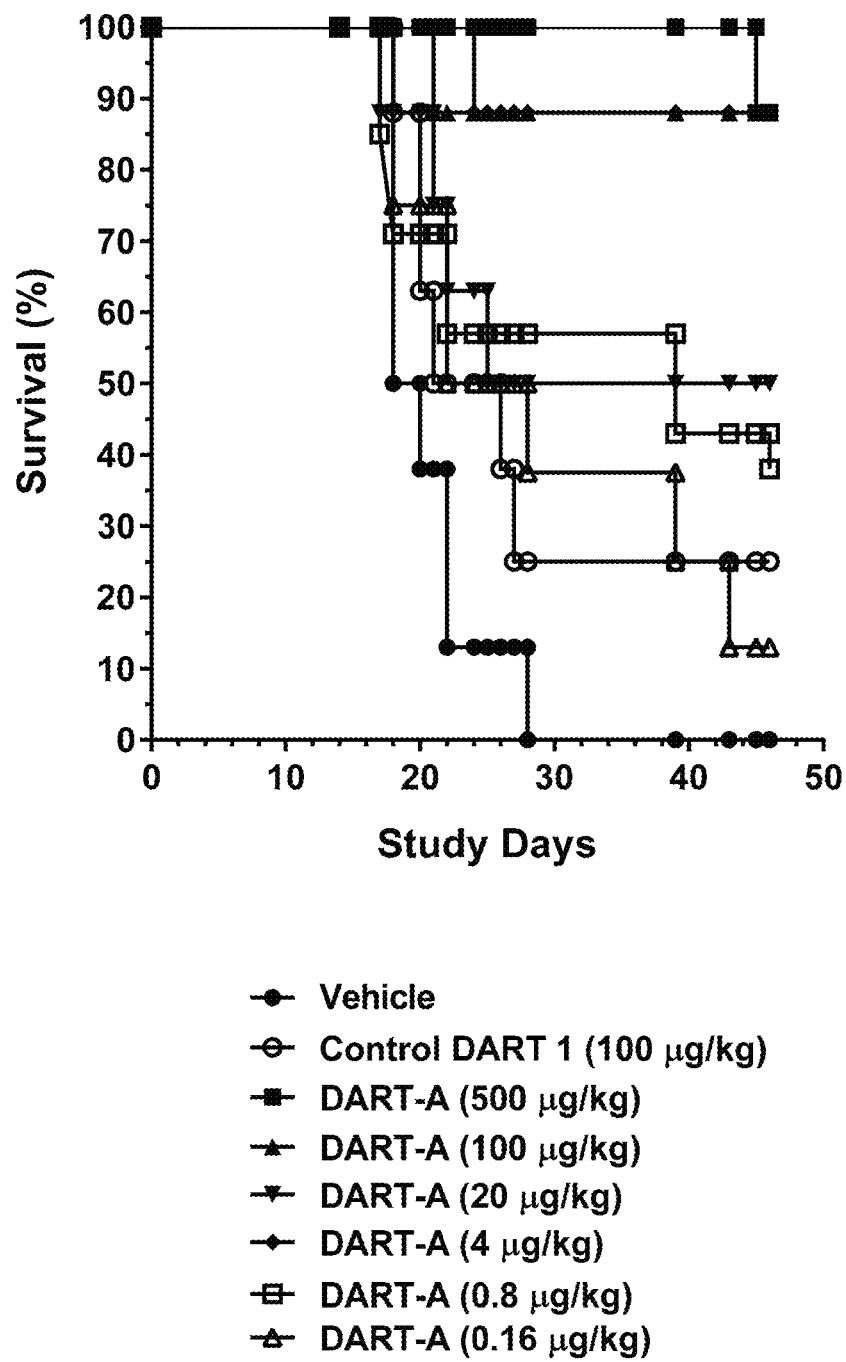
FIG. 26 shows the survival curves in a Raji.luc cell lymphoma model in human PBMC-reconstituted mice following treatment with 500 μg/kg (■), 100 μg/kg (▲), 20 μg/kg (▼), 4 μg/kg (♦), 0.8 μg/kg (□) or 0.16 μg/kg (Δ) DART-A, 0.1 mg/kg Control DART 1 (○) or vehicle control (•).

In the vehicle control group, the tumor burden increased progressively and all mice died or were sacrificed by the end of the second week of treatment (FIG. 26). Mice treated with 0.1 mg/kg Control DART 1 showed a slight delay of tumor progression compared with vehicle-treated mice (FIG. 26). In contract, the tumor burden in the animals treated with DART-A showed a generally dose-dependent reduction over time (FIG. 26).

Example 14

Pharmacokinetics of DART-A in Cynomolgus Monkeys

The cynomolgus monkey was selected as an appropriate pharmacological model for DART-A analysis based on the equivalent distribution of both target antigens in this species compared to humans based on immunohistochemistry with the precursor mAbs.

The study conducted in accordance with the present invention included 5 treatment groups, consisting of 10 cynomolgus monkeys per group (5 males, 5 females). Groups were treated by IV infusion over 2 hours with vehicle control for the first infusion on Day 1, followed by treatment with vehicle control (Group 1) or DART-A (Groups 2-5) once weekly for four weeks. While Group 1 animals continued receiving vehicle control for all 4 subsequent infusions, animals of Groups 2-5 received DART-A at 0.2 µg/kg, 2 µg/kg, 5 µg/kg or 10 µg/kg for all subsequent infusions on Days 8, 15, 22 and 29 (Table 12). Three males and 3 females were euthanized and necropsied on Day 37, while the remaining recovery group monkeys (2 males and 2 females) were euthanized and necropsied on Day 121 after a 12-week recover period.

TABLE 12

| Study Infusion No. | DART-A Infusion No. (Groups 2-5 only) | Study Day | DART-A (µg/kg) Administered as a 2-hour IV Infusion | | | | |
|---|---|---|---|---|---|---|---|
| | | | Group 1 | Group 2 | Group 3 | Group 4 | Group 5 |
| 1 | NA | 1 | 0 | 0 | 0 | 0 | 0 |
| 2 | 1 | 8 | 0 | 0.2 | 2 | 5 | 10 |
| 3 | 2 | 15 | 0 | 0.2 | 2 | 5 | 10 |
| 4 | 3 | 22 | 0 | 0.2 | 2 | 5 | 10 |
| 5 | 4 | 29 | 0 | 0.2 | 2 | 5 | 10 |

Figure 27:
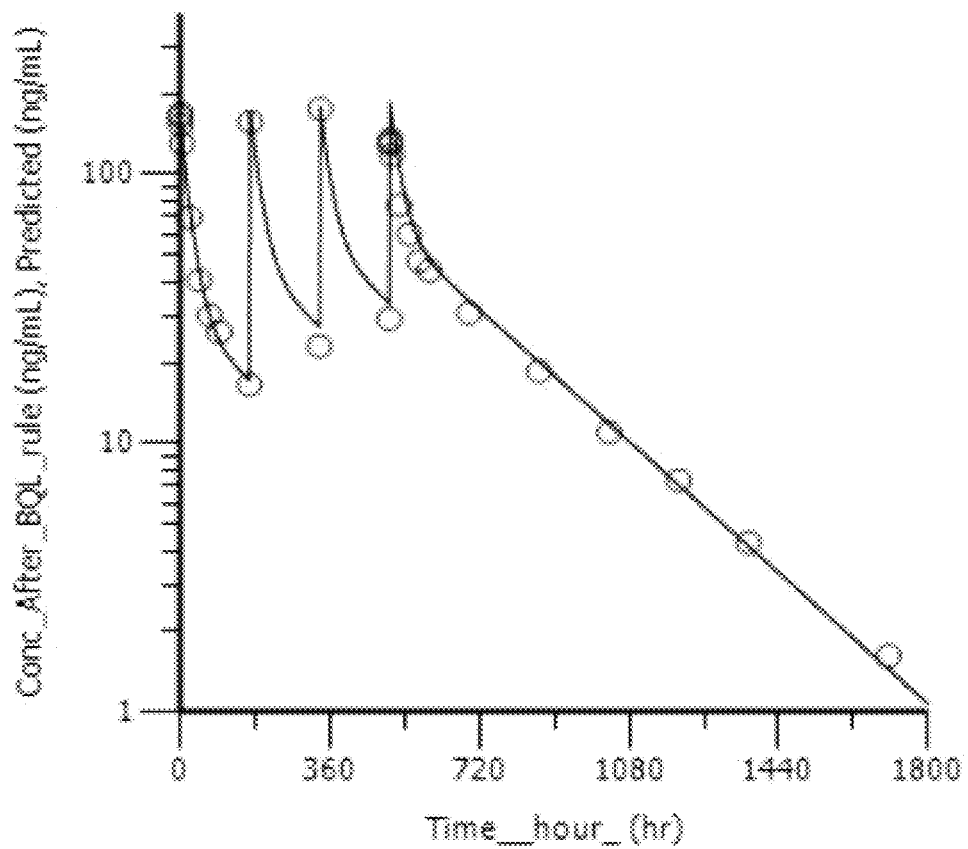
FIG. 27 shows the serum concentration-time profile of DART-A in a cynomolgus monkey dosed with 10 μg/kg DART-A.

Concentration analysis of DART-A in serum collected at various time points was conducted with ELISA. DART-A serum concentration-time profile for a representative animal from Group 5 is shown on FIG. 27. PK parameters (two-compartment model) were estimated following the 0.2, 2, 5 and 10 µg/kg doses (Table 13). In general, dose-proportional increases in maximum serum concentrations ($C_{max}$) and $AUC_{inf}$ were observed across the dose range evaluated. Although differences existed for several pairwise dose comparisons of primary PK parameters, overall, there were no consistent trends in changes in clearance (CL), intercompartmental clearance ($CLD_2$) and volumes of distribution ($V_1$ and $V_2$) for DART-A across the evaluable doses suggesting linear PK. The CL values across the animals of Groups 2-5 are lower than the glomerular filtration rate (GFR) for cynomolgus monkeys (~125 mL/h/kg), which indicates that virtually no elimination occurs by renal filtration, as would be expected for a protein of this molecular weight (109.3 kDa). Mean initial volumes of distribution ($V_1$) for animals of Groups 2, 3, 4, and 5, is similar to or slightly higher than the plasma volume in cynomolgus monkeys (~45 mL/kg), suggesting little depletion of DART-A in the central compartment by binding to target cells. The mean beta-phase half-lives and MRT showed an increasing trend with increasing dose with the mean beta half-life (t1/2,β) was 161 hours (6.7 days) and mean residence time (MRT) was 191 hours (8 days). Of note only three animals from the GLP study (n=1 in 2 µg/kg dose group; n=2 in 5 µg/kg dose group) had aberrant PK profiles following the 2nd and subsequent DART-A infusions (n=2) or following the fourth DART-A infusion (n=1) and were subsequently confirmed positive for ADA. Thus, serum concentration data following the affected infusion cycles were excluded from PK modeling for these 3 animals.

TABLE 13

Two-Compartment Analysis of PK Parameters of DART-A in Cynomolgus Monkeys

| Attribute | 0.2 µg/kg/d (mean ± SD) | 2 µg/kg/d (mean ± SD) | 5 µg/kg/d (mean ± SD) | 10 µg/kg/d (mean ± SD) |
|---|---|---|---|---|
| $C_{max}$ (ng/mL) | 3.18 ± 0.46 | 31.9 ± 3.0 | 82.9 ± 5.6 | 166.6 ± 11.0 |
| $AUC_{inf}$ (h*ng/mL) | 155 ± 37 | 2258 ± 634 | 6714 ± 1846 | 13756 ± 2534 |
| CL (mL/h/kg) | 0.95 ± 0.17 | 0.80 ± 0.22 | 0.73 ± 0.24 | 0.70 ± 0.13 |
| $CLD_2$ (mL/h/kg) | 0.87 ± 0.15 | 1.65 ± 0.36 | 1.70 ± 0.74 | 1.40 ± 0.40 |

TABLE 13-continued

Two-Compartment Analysis of PK Parameters of
DART-A in Cynomolgus Monkeys

| Attribute | 0.2 μg/kg/d (mean ± SD) | 2 μg/kg/d (mean ± SD) | 5 μg/kg/d (mean ± SD) | 10 μg/kg/d (mean ± SD) |
|---|---|---|---|---|
| $V_1$ (mL/kg) | 43.4 ± 5.8 | 50.9 ± 5.1 | 52.3 ± 3.5 | 54.5 ± 4.5 |
| $V_2$ (mL/kg) | 65.3 ± 17.5 | 77.9 ± 17.9 | 93.4 ± 33.3 | 105.3 ± 33.0 |
| $V_{ss}$ (mL/kg) | 108.7 ± 16.6 | 128.8 ± 17.2 | 145.8 ± 34.6 | 159.8 ± 36.0 |
| $t_{1/2}$ (h) | 14.0 ± 1.5 | 11.0 ± 2.2 | 12.3 ± 3.8 | 15.0 ± 4.4 |
| $t_{1/2,\,\beta}$ (h) | 119.1 ± 27.6 | 143.4 ± 43.4 | 184.9 ± 72.0 | 205.6 ± 66.9 |
| MRT (h) | 116.3 ± 20.3 | 173.0 ± 54.5 | 221.2 ± 86.5 | 235.9 ± 72.0 |

Cytokine Release in DART-A-Treated Cynomolgus Monkeys

Serum samples to evaluate cytokine levels were collected prior to infusion and at 2 and 22 hours following the end of infusion on Days 1, 8, 15, 22 and 29. Cytokines evaluated were TNF-α, IFN-γ, IL-2, IL-4, IL-5, IL-6 and IL-10.

An increase in the levels of IL-6, IL-10, IFN-γ and TNF-α was observed following the first DART-A infusion (DAY 8), with respect to the greatest increase in cytokine levels occurring 2 hours following the end of infusion. A DART-A dose-dependent increase was observed for IL-10 and IFN-γ at dose levels >2 μg/kg, while an increase in IL-6 was observed at dose levels ≥5 μg/kg. Changes in TNF-α levels were small and were observed only at the highest dose level (10 μg/kg). Changes in cytokine levels were transient and returned to at or near baseline within 24 hours of the start of the infusion, and there were no clinical observations associated with these increased cytokine levels. Subsequent infusions of DART-A on Days 15, 22 and 29 resulted in smaller cytokine level increases, generally comparable to those observed following control article infusion. Mean levels of IL-2, IL-4 and IL-5 showed variable and isolated changes in individual animals, but remained <20 pg/mL across all groups throughout the duration of the study and were not considered toxicologically significant.

Cytokine levels in animals receiving 0.2 μg/kg DART-A were comparable to the variations observed following control article infusion (Group 1).

DART-A-Mediated Depletion of Circulating B-Cells in Cynomolgus Monkeys

The circulating absolute levels of B cells, T cells, including T cell subsets (CD4 vs CD8) and activation markers (CD25, CD69, PD-1 and TIM-3), and NK cells, were measured throughout the study as a pharmacodynamic endpoint. Samples were collected prior to infusion and at 2, 22 and 70 hours following the end of infusion on Days 1, 8, 22 and 29, prior to terminal necropsy on Day 37, and then weekly or biweekly during the recovery period on Days 36, 43, 50, 57, 64, 78, 92, 106 and 119.

Figure 28:
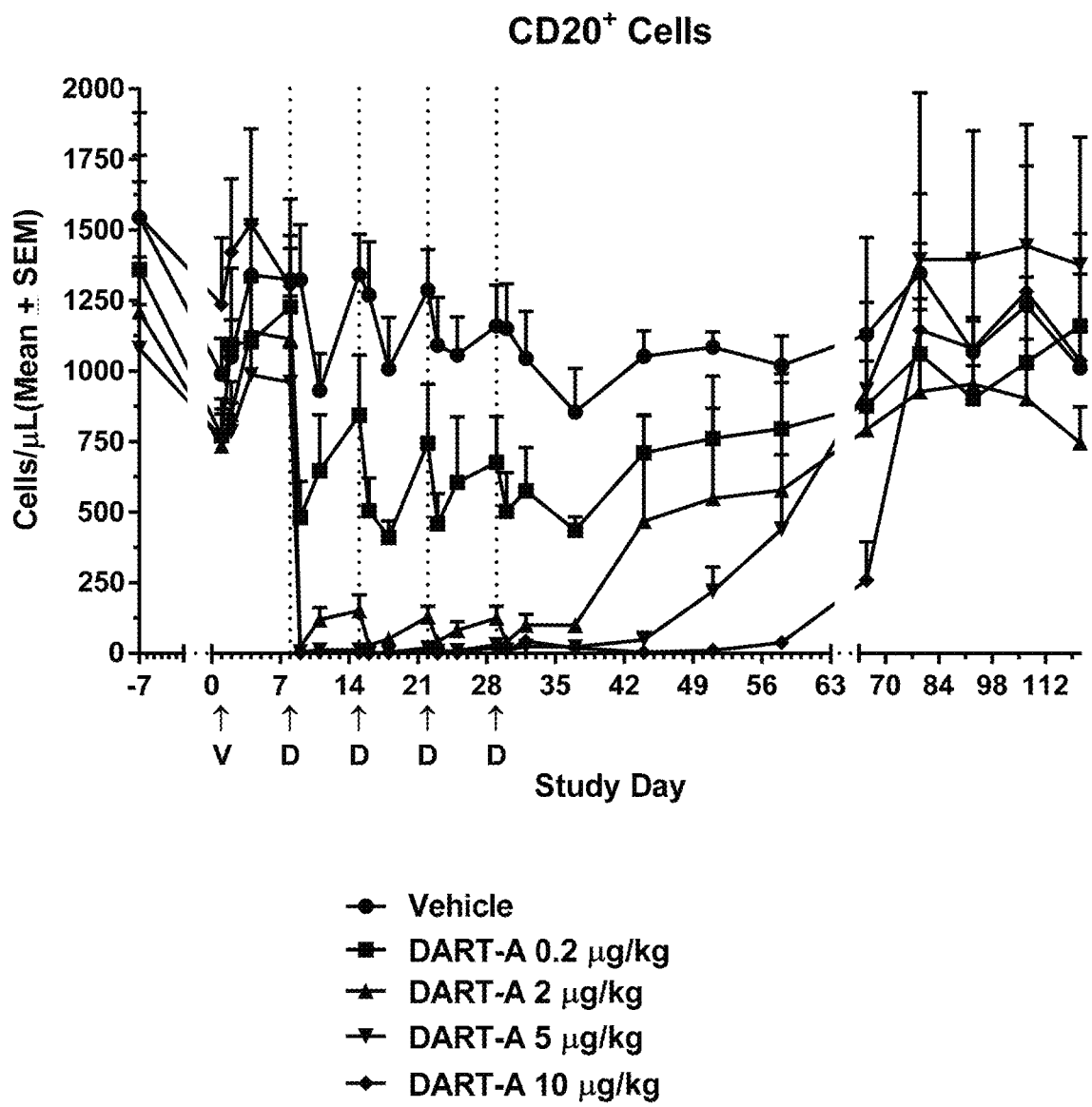
FIG. 28 shows the mean±SEM number of CD45+/CD20+ cells/L as determined by flow cytometry for a Study Day and Group. The dashed vertical lines on Days 8, 15, 22 and 29 indicate each dose (D) of DART-A by 2-hour IV infusion for animals of Groups 2-5; while animals of Group 1 continued to receive vehicle control. The x-axis indicating Study Day is split into 3 segments covering Day −7 to −1, Day 0 to 63 and Day 64-121.
Figure 29A:
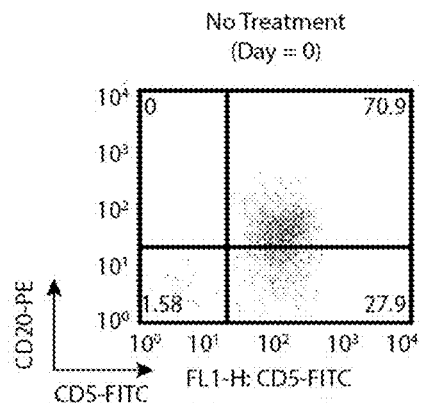
FIGS. 29A-29I show representative FACS analysis of malignant B cells (CD20+/CD5+) (FIGS. 29A-29C), T cells (CD4+ or CD8+) (FIGS. 29D-29E) and T cell activation (CD25 in CD4+(FIGS. 29F-29G) or CD8+(FIGS. 29H-29I) T cells) in CLL PBMCs (E:T=1:23) following No treatment (FIG. 29A), DART-A (FIGS. 29C, 29E, 29G and 29I) or Control DART 1 (FIGS. 29B, 29D, 29F and 29H) treatment for 6 days.
Figure 29B:
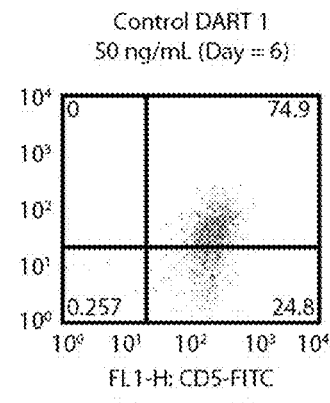
Figure 29C:
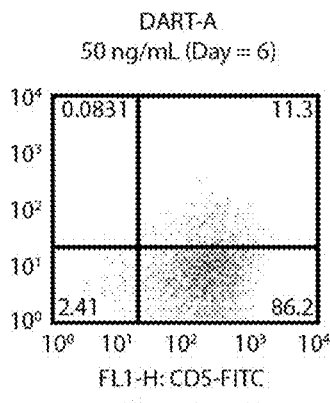
Figure 29D:
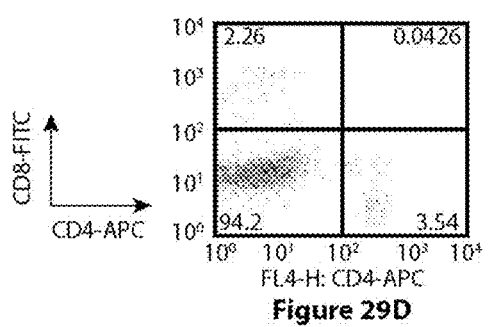
Figure 29E:
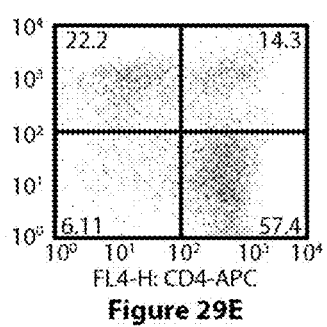
Figure 29F:
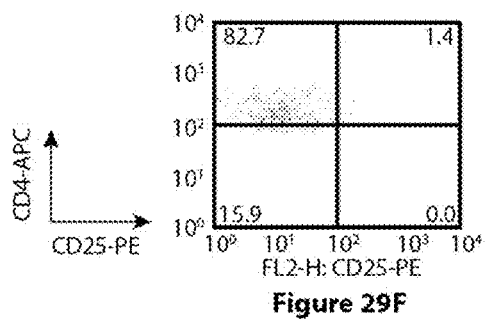
Figure 29G:
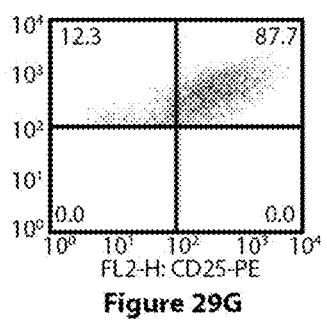
Figure 29H:
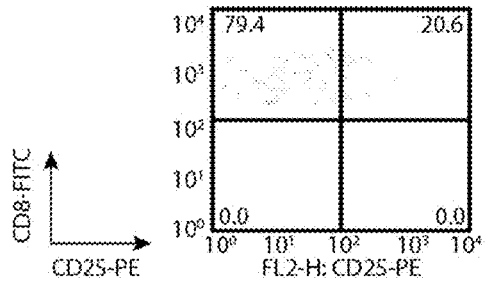
Figure 29I:
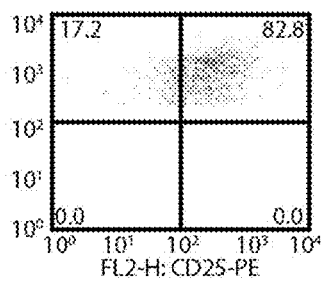

FIG. 28 shows that DART-A treatment resulted in a dose-dependent depletion of CD20+ B cells, the intended target population. Complete or near complete depletion of CD20+ cells was observed by 24 hours following the start of the first infusion of DART-A at dose levels ≥2 μg/kg. The depletion of CD20+ B cells was durable throughout the treatment period and was sustained for 3-5 weeks after final dose. There was a dose-dependent return to pre-dose levels of CD20+ B cells during the last several weeks of the 12-week recovery period.

Example 15

Autologous Depletion of Malignant B Cells in CLL Primary Patient Samples

To evaluate DART-A-mediated cytolytic activity in CLL primary patient samples, patient PBMCs were incubated with DART-A or Control DART 1. Due to the limited patient sample availability, only 2 concentrations (50 ng/mL and 200 ng/mL) were tested. The percentages of CLL malignant B cells (CD19+/CD5+ or CD20+/CD5+) and T cells (CD19−/CD5+ or CD4+ and CD8+) were measured by flow cytometry prior to treatment and following treatment for 3 and 6 days. DART-A at the concentrations tested partially blocks staining of anti-CD19 antibody, therefore, it was not appropriate to use CD19+/CD5+ to gate malignant B cells after treatment with DART-A. Thus, malignant B cell depletion was determined by gating on CD20+/CD5+ cells following DART-A treatment.

The E:T ratio determined from CLL malignant B cell and T cell frequencies was generally ≤1:10. In the representative CLL donor experiment shown, the E:T cell ratio was approximately 1:23 prior to treatment based on CD19−/CD5+ T cells comprising only 4% of the total PBMCs and about 90% of PBMCs identified as CD19+/CD5+ malignant B cells. FIGS. 29A-29I and Table 14 show the effects of DART-A treatment compared with CLL patient sample. Incubation of DART-A with CLL PBMCs resulted in a time-dependent depletion of malignant B cells at both DART-A concentrations evaluated, accompanied by a concomitant increase in T cells (CD4 and CD8) observed on Day 6. In addition, the T cell activation marker CD25 was upregulated following DART-A treatment for 6 days, indicating the DART-A induces T cell activation in the process of redirected killing of malignant B cells In contrast, no B cell killing or upregulation of CD25 was observed with Control DART 1 through Day 6.

Of note, DART-A mediated the same level of killing at both concentrations evaluated, but the level of killing increased over time with approximately 40% and 85% of malignant B cells being killed on Day 3 and Day 6, respectively, suggesting that time is the critical factor for the efficient elimination of target cells under low T cell to target ratios when sufficient DART-A is present.

TABLE 14

Percentages of Malignant B Cells (CD20+/CD5+), T cells (CD4, CD8+) and
Activated T Cells (CD25+/CD4+ and CD25+/CD8+) in CLL PBMCs (E:T = 1:23)
after DART-A or Control DART 1 Treatment for 3 and 6 Days

| | Percentages (%) | | | | |
|---|---|---|---|---|---|
| Time Point | CD20+/CD5+ | CD4+ | CD8+ | CD25+/CD4+ | CD25+/CD8+ |
| Day 0 | | | | | |
| Pretreatment | 70.7 | n.d.[1] | | CD4+ and CD8+ T cell subsets were not measured on Day 0. CD19−/CD5+ was used to define the T cell population on Day 0 (4%) as described above. | |

TABLE 14-continued

Percentages of Malignant B Cells (CD20+/CD5+), T cells (CD4, CD8+) and
Activated T Cells (CD25+/CD4+ and CD25+/CD8+) in CLL PBMCs (E:T = 1:23)
after DART-A or Control DART 1 Treatment for 3 and 6 Days

| Time Point | Percentages (%) | | | | |
|---|---|---|---|---|---|
| | CD20+/CD5+ | CD4+ | CD8+ | CD25+/CD4+ | CD25+/CD8+ |
| Day 3 | | | | | |
| DART-A (50 ng/mL) | 40.5 | 1.01 | 1.78 | Overall T cell percentages were too low (<5%) to evaluate T cell activation marker CD25 on Day 0 or Day 3. | |
| Control DART 1 (50 ng/mL) | 73.5 | 3.08 | 1.81 | | |
| DART-A (200 ng/mL) | 42.3 | 1.61 | 1.68 | | |
| Control DART 1 (200 ng/mL) | 72.9 | 3.23 | 1.62 | | |
| Day 6 | | | | | |
| DART-A (50 ng/mL) | 11.3 | 57.4 | 22.2 | 87.7 | 82.8 |
| Control DART 1 (50 ng/mL) | 74.9 | 3.54 | 2.26 | 1.4 | 20.6 |
| DART-A (200 ng/mL) | 12.3 | 65.2 | 20.9 | 91.6 | 90.7 |
| Control DART 1 (200 ng/mL) | 73.4 | 2.79 | 1.82 | 1.4 | 14.3 |

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating a hematologic malignancy associated with the expression of CD19 in a subject in need thereof, said method comprising administering to said subject a CD19×CD3 bi-specific Fc diabody that specifically binds to CD19 and to CD3, wherein the diabody comprises a first, a second and a third polypeptide chain, wherein said polypeptide chains form a covalently bonded complex, and wherein:

I. said first polypeptide chain comprises, in the N-terminal to C-terminal direction:
  A. a Domain IA, comprising:
    (1) a sub-Domain (IA1), which comprises a VL Domain that binds to either CD19 ($VL_{CD19}$) or CD3 ($VL_{CD3}$); and
    (2) a sub-Domain (IA2), which comprises a VH Domain that binds to either CD19 ($VH_{CD19}$) or CD3 ($VH_{CD3}$);
    wherein said sub-Domains IA1 and IA2 are separated from one another by a polypeptide linker, and are either:
      (a) $VL_{CD19}$ and $VH_{CD3}$; or
      (b) $VL_{CD3}$ and $VH_{CD19}$;
  B. a Domain IB that comprises a charged helical domain, wherein said Domain IB is separated from said Domain IA by a polypeptide linker;
  C. a Domain IC, comprising a CH2-CH3 Domain of an antibody; and II. said second polypeptide chain comprises, in the N-terminal to C-terminal direction:
  A. a Domain IIA, comprising:
    (1) a sub-Domain (IIA1), which comprises a VL Domain that binds to either CD19 ($VL_{CD19}$) or CD3 ($VL_{CD3}$); and
    (2) a sub-Domain (IIA2), which comprises a VH Domain that binds to either CD19 ($VH_{CD19}$) or CD3 ($VH_{CD3}$);
    wherein said sub-Domains IIA1 and IIA2 are separated from one another by a polypeptide linker, and are either:
      (a) $VL_{CD19}$ and $VH_{CD3}$, if said sub-Domains IA1 and IA2 are $VL_{CD3}$ and $VH_{CD19}$; or
      (b) $VL_{CD3}$ and $VH_{CD19}$, if said sub-Domains IA1 and IA2 are $VL_{CD19}$ and $VH_{CD3}$;
  B. a Domain IIB, that comprises a charged helical domain, wherein said Domain IIB is separated from said Domain IIA by a polypeptide linker, and wherein said charged helical domain of said Domain IB and said charged helical domain of said Domain IIB have opposite charges; and III. said third polypeptide chain comprises, in the N-terminal to C-terminal direction a Domain IIIC that comprises a CH2-CH3 Domain of an antibody;

wherein:
(1) said $VL_{CD19}$ comprises the amino acid sequence of SEQ ID NO:17 and said $VH_{CD19}$ comprises the amino acid sequence of SEQ ID NO:21; and
(2) said $VL_{CD3}$ comprises the amino acid sequence of SEQ ID NO:25 and said $VH_{CD3}$ comprises the amino acid sequence of SEQ ID NO:29; and
(3) said $VL_{CD19}$ and said $VH_{CD19}$ domains form a monovalent CD19 binding domain; and
(4) said $VL_{CD3}$ and $VH_{CD3}$ domains form a monovalent CD3 binding domain; and
(5) (A) said charged helical domain of said Domain IB comprises the amino acid sequence of SEQ ID NO:10, and said charged helical domain of said Domain IIB comprises the amino acid sequence of SEQ ID NO:11; or
(B) said charged helical domain of said Domain IB comprises the amino acid sequence of SEQ ID NO:11, and said charged helical domain of said Domain IIB comprises the amino acid sequence of SEQ ID NO:10; or
(C) said charged helical domain of said Domain IB comprises the amino acid sequence of SEQ ID NO:12, and said charged helical domain of said Domain JIB comprises the amino acid sequence of SEQ ID NO:13; or
(D) said charged helical domain of said Domain IB comprises the amino acid sequence of SEQ ID NO:13, and said charged helical domain of said Domain JIB comprises the amino acid sequence of SEQ ID NO:12; and
(6) said CH2-CH3 Domains of said first and third polypeptide chains form an Fc domain that binds to an Fc receptor, thereby forming said CD19×CD3 bi-specific Fc diabody.

2. The method of claim 1, wherein:
(A) said Domains IB and JIB each comprise a cysteine residue that covalently bonds said first polypeptide chain to said second polypeptide chain via a disulfide bond; and
(B) said Domains IC and IIIC each comprise a cysteine residue that covalently bonds said first polypeptide chain to said third polypeptide chain via a disulfide bond.

3. The method of claim 1, wherein said CH2-CH3 Domain of said Domain IC comprises the amino acid sequence of SEQ ID NO:15 and said CH2-CH3 Domain of said Domain IIIC comprises the amino acid sequence of SEQ ID NO:16.

4. The method of claim 1, wherein:
(A) said charged helical domain of said Domain IB comprises the amino acid sequence of SEQ ID NO:10, and said charged helical domain of said Domain IIB comprises the amino acid sequence of SEQ ID NO:11; or
(B) said charged helical domain of said Domain IB comprises the amino acid sequence of SEQ ID NO:12, and said charged helical domain of said Domain IIB comprises the amino acid sequence of SEQ ID NO:13.

5. The method of claim 1, wherein:
(A) said first polypeptide chain comprises the amino acid sequence of SEQ ID NO:35;
(B) said second polypeptide chain comprises the amino acid sequence of SEQ ID NO:37; and
(C) said third polypeptide chain comprises the amino acid sequence of SEQ ID NO:39.

6. The method of claim 1, wherein said monovalent CD19 binding domain cross-reacts with both human and primate CD19, and said monovalent CD3 binding domain cross-reacts with both human and primate CD3.

7. The method of claim 1, wherein said hematologic malignancy is selected from the group consisting of: acute myeloid leukemia (AML), chronic myelogenous leukemia (CML), blastic crisis of CML, Abelson oncogene associated with CIVIL (Bcr-ABL translocation), myelodysplastic syndrome (MDS), acute B lymphoblastic leukemia (B-ALL), diffuse large B cell lymphoma (DLBCL), follicular lymphoma, chronic lymphocytic leukemia (CLL), Richter's syndrome, Richter's transformation of CLL, hairy cell leukemia (HCL), blastic plasmacytoid dendritic cell neoplasm (BPDCN), non-Hodgkin lymphomas (NHL), mantel cell leukemia (MCL), small lymphocytic lymphoma (SLL), Hodgkin's lymphoma, systemic mastocytosis, and Burkitt's lymphoma.

8. A polynucleotide encoding a polypeptide comprising the amino acid sequence of SEQ ID NO:35 or SEQ ID NO:37.

9. An expression vector comprising the polynucleotide of claim 8.

10. A host cell comprising:
   (a) polynucleotide encoding a polypeptide comprising the amino acid sequence of SEQ ID NO:35;
   (b) a polynucleotide encoding a polypeptide comprising the amino acid sequence of SEQ ID NO:37; and
   (c) a polynucleotide encoding a polypeptide comprising the amino acid sequence of SEQ ID NO:39.

* * * * *